US009944675B2

(12) United States Patent
Fiacco et al.

(10) Patent No.: US 9,944,675 B2
(45) Date of Patent: Apr. 17, 2018

(54) METHODS FOR PREPARING HIGH THROUGHPUT PEPTIDOMIMETICS, ORALLY BIOAVAILABLE DRUGS AND COMPOSITIONS CONTAINING SAME

(75) Inventors: Stephen V. Fiacco, South Pasadena, CA (US); Terry T. Takahashi, Pasadena, CA (US); Richard W. Roberts, South Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 399 days.

(21) Appl. No.: 14/342,347

(22) PCT Filed: Aug. 31, 2012

(86) PCT No.: PCT/US2012/053526
§ 371 (c)(1),
(2), (4) Date: Oct. 28, 2014

(87) PCT Pub. No.: WO2013/033636
PCT Pub. Date: Mar. 7, 2013

(65) Prior Publication Data
US 2015/0050211 A1    Feb. 19, 2015

Related U.S. Application Data

(60) Provisional application No. 61/530,327, filed on Sep. 1, 2011, provisional application No. 61/530,352, filed on Sep. 1, 2011, provisional application No. 61/530,372, filed on Sep. 1, 2011.

(51) Int. Cl.
| | |
|---|---|
| *C07K 7/06* | (2006.01) |
| *G01N 33/574* | (2006.01) |
| *A61K 38/28* | (2006.01) |
| *A61K 49/00* | (2006.01) |
| *A61K 51/08* | (2006.01) |
| *C12N 5/09* | (2010.01) |
| *C12Q 1/68* | (2018.01) |
| *G01N 33/50* | (2006.01) |
| *G01N 33/68* | (2006.01) |
| *C12N 15/67* | (2006.01) |
| *A61K 47/60* | (2017.01) |
| *A61K 47/55* | (2017.01) |

(52) U.S. Cl.
CPC ............... *C07K 7/06* (2013.01); *A61K 38/28* (2013.01); *A61K 47/551* (2017.08); *A61K 47/60* (2017.08); *A61K 49/0056* (2013.01); *A61K 51/088* (2013.01); *C12N 5/0693* (2013.01); *C12N 15/67* (2013.01); *C12Q 1/6811* (2013.01); *G01N 33/5011* (2013.01); *G01N 33/57415* (2013.01); *G01N 33/6803* (2013.01); *C12N 2501/998* (2013.01); *G01N 2500/04* (2013.01); *G01N 2500/10* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 5,922,545 | A | 7/1999 | Mattheakis et al. |
| 2008/0081768 | A1 | 4/2008 | Watt et al. |
| 2009/0215032 | A1 | 8/2009 | White et al. |
| 2010/0099103 | A1 | 4/2010 | Hsieh et al. |

FOREIGN PATENT DOCUMENTS

| | | |
|---|---|---|
| EP | 2 141 175 | 1/2010 |
| EP | 2 615 455 | 7/2013 |
| EP | 2 647 720 | 10/2013 |
| WO | WO-99/05302 A1 | 2/1999 |
| WO | WO-01/57070 A1 | 8/2001 |
| WO | WO-03/089454 | 10/2003 |
| WO | WO-2004/110964 | 12/2004 |
| WO | WO 2006/003183 * | 1/2006 |
| WO | WO-2006/138562 A2 | 12/2006 |
| WO | WO-2008/117833 A1 | 10/2008 |
| WO | WO-2015/175747 A1 | 11/2015 |
| WO | WO-2015/175748 A1 | 11/2015 |

OTHER PUBLICATIONS

Millward et al. ACS chemical biology 2.9 (2007): 625-634.*
Goto Y et al. (2008), "Reprogramming the Translation Initiation for the Synthesis of Physiologically Stable Cyclic Peptides", ACS Chem. Biol. 2008, vol. 3, No. 2, pp. 120-129.
Hayashi G et al. (2010), "Ribosomal synthesis of nonstandard cyclic peptides and its application to drug discovery", Biochemistry, vol. 82, No. 6, pp. 505-514.

(Continued)

*Primary Examiner* — Christina Bradley
(74) *Attorney, Agent, or Firm* — Foley & Lardner LLP; Antoinette F. Konski; Natasha Iyer

(57) ABSTRACT

Provided herein are methods to generate and screen peptides that exhibit drug like stabilities in vitro and in vivo. By selecting for enzyme resistance, Applicants are able to derive peptides that are not only stable to a broad spectrum of proteases, but also stable to other drug processing enzymes such as cytochrome P450s. This approach provides a general method to the rapid development of highly stable peptides for therapeutic development and diagnosis. The peptides are further modified for oral bioavailability. The methods can be applied to similar peptides for the making of therapeutic compositions.

15 Claims, 24 Drawing Sheets

(56) References Cited

OTHER PUBLICATIONS

Calceti et al. (2004), "Development and in vivo evaluation of an oral insulin-PEG delivery system", Eur J Pharm Sci 2004, 22(4):315-323.
Covic et al. (2002), "Pepducin-based intervention of thrombin-receptor signaling and systemic platelet activation", Nat Med 2002, 8(10):1161-1165.
Endres et al. (2006), "Quantitative imaging of cell-permeable magnetic resonance contrast agents using x-ray fluorescence", Mol Imaging 2006, 5(4):485-497.
Extended European Search Report and Search Opinion for European Patent Application No. 12828021.1, dated Jun. 2, 2015, 13 pages.
Fabry et al., "Design and synthesis of a nove 1 biotinylated photoreactive insulin for receptor analysis," Biological Chemistry Hoppe-Seyler, 373(3):143-150 (1992).
Fiacco et al. (2008), "N-Methyl Scanning Mutagenesis Generates Protease-Resistant G Protein Ligands with Improved Affinity and Selectivity", CHembiochem. Sep. 22, 2008, 9(14): 2200-2203.
Forster A C et al. (2003), "Programming peptidomimetic syntheses by translating genetic codes designed de novo", Proceedings of the National Academy of Sciences, vol. 100, No. 11, May 27, 2003, pp. 6353-6357.
Frankel et al. (2003), "Encodamers: Unnatural Peptide Oligomers Encoded in RNA", Chemistry & Biology, vol. 10, 1043-1050.
Gilmore et al. "Incorporation of Noncoded Amino Acids by In Vitro Protein Biosynthesis", In Implementation and Redesign of Catalytic Function in Biopolymers; Springer Berlin / Heidelberg (1999) 202:77-99.
Goubaeva et al. (2003), "Stimulation of Cellular Signaling and G Protein Subunit Dissociation by G Protein 3B23B3 Subunit-binding Peptides", The Journal of Biological Chemistry, vol. 278, No. 22, pp. 19634-19641.
Hendrickson Tamara L et al. (2004), "Incorporation of non-natural amino acids into proteins", Annual Review of Biochemistry, vol. 73, Mar. 26, 2004, pp. 147-176.
International Search Report and Written Opinion for PCT International Patent Application No. PCT/US2012/053526, dated Feb. 14, 2013.
Ja et al. (2004), "In Vitro Selection of State-Specific Peptide Modulators of G Protein Signaling Using mRNA Display", Biochemistry 2004, 43, 9265-9275.
Ja et al. (2006), "Turning G proteins on and off using peptide ligands", ACS Chem Biol. Oct. 24, 2006, 1(9): 570-574.
Kawakami et al. (2008), "Messenger RNA-Programmed Incorporation of Multiple N-Methyl-Amino Acids into Linear and Cyclic Peptides", Chemistry and Biology, Current Biology, London, GB, vol. 15, No. 1, Jan. 25, 2008, pp. 32-42.
Kwon et al. (2007), "Quantitative comparison of the relative cell permeability of cyclic and linear peptides", Chem Biol. 2007, 14(6):671-677.
Liu C C et al (2009), "Evolution of Proteins with Genetically Encoded Chemical Warheads", Journal of the American Chemical Society, vol. 131, Jul. 22, 2009, pp. 9616-9617.
Miller et al. (1994), "Proteolytic Studies of Homologous Peptide and N Substituted Glycine Peptide and Peptide Oligomers", Bioorganic & Medicinal Chemistry Letters, vol. 4, No. 22, pp. 2657-2662.
Millward et al., "Design of cyclic peptides that bind protein surfaces with antibody-like affinity," ACS Chemical Biology 2(9):625-634 (2007).
Morimoto J et al. (2012), "Discovery of Macrocyclic Peptides Armed with a Mechanism-Based Warhead: Isoform-Selective Inhibition of Human Deacetylase SIRT2", Angewandte Chemie International Edition, vol. 51, No. 14, Feb. 28, 2012, pp. 3423-3427.
Nakajima et al. (2008), "Development of HER2-antagonistic peptides as novel anti-breast cancer drugs by in silico methods", Breast Cancer 2008, 15(1):65-72.
Nguyen et al. (1998), "Exploiting the basis of proline recognition by SH3 and WW domains: design of N-substituted inhibitors", Science Dec. 11, 1998, 282(5396):2088-2092.
Park et al. (2000), "Rationally designed anti-HER2/neu peptide mimetic disables P185HER2/neu tyrosine kinases in vitro and in vivo", Nat Biotechnol. Feb. 2000, 18(2):194-198.
Rezai et al. (2006), "Testing the conformational hypothesis of passive membrane permeability using synthetic cyclic peptide diastereomers", J Am Chem Soc Mar. 1, 2006, 128(8): 2510-2511.
Roberts R W et al. (1997), "RNA-peptide fusions for the in vitro selection of peptides and proteins", Proceedings of the National Academy of Sciences, vol. 94, No. 23, Jan. 1, 1997, pp. 12297-12302.
Seebeck F P et al. (2006), "Ribosomal synthesis of dehydroalanine-containing peptides", Journal of the American Chemical Society, vol. 128, No. 22, Jun. 1, 2006, pp. 7150-7151.
Stoop et al. (2003), "Engineering of a macromolecular scaffold to develop specific protease inhibitors", Nature Biotechnology, vol. 21, No. 9, 1063-1068.
Tuesca et al. (2009), "Synthesis, characterization and in vivo efficacy of PEGylated insulin for oral delivery with complexation hydrogels", Pharm Res 2009, 26(3):727-739.
Wadia et al. (2004), "Transducible TAT-HA fusogenic peptide enhances escape of TAT-fusion proteins after lipid raft macropinocytosis", Nat Med 2004, 10, 310-315.
Walensky et al. (2004), "Activation of Apoptosis in Vivo by a Hydrocarbon-Stapled BH3", Science Sep. 3, 2004, 305(5689): 1466-1470.
Yamagishi Y et al. (2011), "Natural Product-Like Macrocyclic-Methyl-Peptide Inhibitors against a Ubiquitin Ligase Uncovered from a Ribosome-Expressed De Novo Library", Chemistry and Biology, Current Biology, London, GB, vol. 18, No. 12, Sep. 20, 2011, pp. 1562-1570.
Extended European Search Report dated Aug. 25, 2017, from application No. 17156757.1.
Moretto, et al. "N-methylation of N(alpha)-acylated, fully C(alpha)-methylated, linear, folded peptides: synthetic and conformational aspects", Biopolymers 2006, vol. 84, No. 6, 2006, pp. 553-565.
Schoch, et al. "Conformational characteristics of alternating stereo-co-oligopeptides of D- and L-norleucine: influence of an N-methyl group", Int J Peptide Protein Res, vol. 44, Jan. 1, 1994, pp. 10-18.
Subtelny et al. "Ribosomal Synthesis of N-Methyl Peptides", Journal of the American Chemical Society, vol. 130, No. 19, May 1, 2008 (May 1, 2008), pp. 6131-6136.
U.S. Office Action dated Aug. 22, 2017, from U.S. Appl. No. 15/009,721.

* cited by examiner

SUPR Peptide    Scanning
                           Unnatural
MFYAYEYAQWSK    Protease
                            Resistant a   Herceptin based library
    *Diversity = 16.8 million*

| M | X | G | D | G | F | Y | A | X | K |
|---|---|---|---|---|---|---|---|---|---|
|ATG|NNS|GGC|GAT|GGT|TTC|TAT|GCC|NNS|AAA|
|   |V  |V  |V  |V  |V  |V  |V  |D  |   |
|   |TAG|TAG|TAG|TAG|TAG|TAG|TAG|   |   |
|   |Y  |Y  |Y  |Y  |   |   |E  |   |   |
|   |TAC|TAT|TAT|TAC|   |   |GAG|   |   |
|   |D  |E  |D  |L  |   |   |D  |   |   |
|   |GAC|GAG|GAT|TTG|   |   |GAC|   |   |
|   |C  |   |C  |   |   |   |A  |   |   |
|   |TGC|   |TGT|   |   |   |GCG|   |   |
|   |E  |   |E  |   |   |   |S  |   |   |
|   |GAG|   |GAG|   |   |   |TCC|   |   |
|   |W  |   |W  |   |   |   |S  |   |   |
|   |TGG|   |TGG|   |   |   |TCG|   |   |
|   |G  |   |G  |   |   |   |Y  |   |   |
|   |GGG|   |GGG|   |   |   |TAC|   |   | b   Pertuzumab based library
    *Diversity = 4.2 million*

| M | X | P | H | A | H | F | X | K |
|---|---|---|---|---|---|---|---|---|
|ATG|NNS|CCT|CAT|GCT|CAC|TTT|NNS|AAA|
|   |A  |V  |V  |V  |V  |V  |H  |   |
|   |   |TAG|TAG|TAG|TAG|TAG|   |   |
|   |   |Y  |Y  |D  |Y  |L  |   |   |
|   |   |TAT|TAT|GAT|TAC|TTG|   |   |
|   |   |S  |H  |Y  |Q  |Y  |   |   |
|   |   |TCT|CAT|TAT|CAG|TAT|   |   |
|   |   |H  |   |S  |   |   |   |   |
|   |   |CAT|   |TCT|   |   |   |   |
|   |   |P  |   |A  |   |   |   |   |
|   |   |CCT|   |GCT|   |   |   |   |
|   |   |Q  |   |E  |   |   |   |   |
|   |   |CAG|   |GAG|   |   |   |   |
|   |   |S  |   |S  |   |   |   |   |
|   |   |TCG|   |TCG|   |   |   |   |

FIGURE 9 a  Peptide 1
   FAM-DQLYWWEYL-(CH$_2$CH$_2$NH)-R
   Peptide 2
   FAM-DQLYWWEYL-(CH$_2$CH$_2$NH)-R'
   Peptide 3
   R-K(FAM)KLSSIESDV
   Peptide 4
   R'-K(FAM)KLSSIESDV
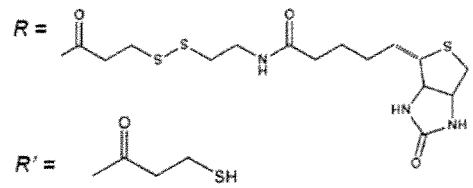
 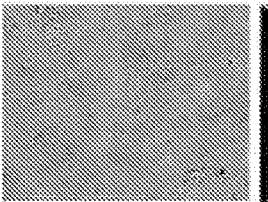   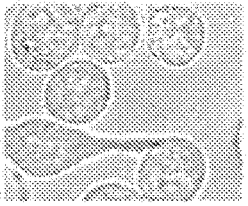
 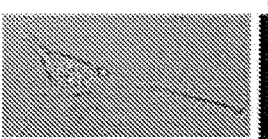  
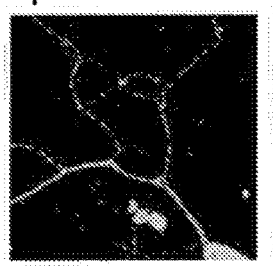 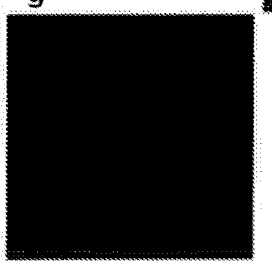
FIGURES 17A to 17G

METHODS FOR PREPARING HIGH THROUGHPUT PEPTIDOMIMETICS, ORALLY BIOAVAILABLE DRUGS AND COMPOSITIONS CONTAINING SAME

CROSS-REFERENCE TO RELATED APPLICATIONS

This application claims the benefit under 35 U.S.C. § 119(e) of U.S. Provisional Application Nos. 61/530,327, 61/530,352 and 61/530,372, each filed Sep. 1, 2011, the contents each of which are incorporated herein by reference into the present disclosure.

STATEMENT AS TO FEDERALLY SPONSORED RESEARCH OR DEVELOPMENT

This invention was made with government support under the National Institutes of Health Grant No. R01 GM 60416. Accordingly, the U.S. Government has certain rights to the invention.

SEQUENCE LISTING

The instant application contains a Sequence Listing which has been submitted electronically in ASCII format and is hereby incorporated by reference in its entirety. Said ASCII copy, created on Apr. 17, 2017, is named 064189-5111_SL.txt and is 40,559 bytes in size.

BACKGROUND

Improved understanding of cellular function as well as disease pathology provides many possible targets for developing new therapeutic and diagnostic reagents. A general problem with turning this cellular knowledge into treatments is that many potential targets are functionally undruggable. Hopkins et al. (2002) Nat. Rev. Drug Discov. 1:727. Therefore, it is not possible to develop small molecules that can modulate many of the protein-protein interactions that control cellular function.

Monoclonal antibodies provide an important route to target protein surfaces and represent both a large and growing portion of approved therapeutics. Nelson et al. (2009) Nat. Biotech. 27:331. However, antibodies are expensive to produce and dose, difficult to administer and control quality, can produce neutralizing immune responses, and cannot be used to target intracellular proteins. Cho et al. (1996) Trends in Biotech. 14:153. The fact that such cumbersome molecules dominate therapeutic protein-binding reagents demonstrates both the importance of these reagents and our desperation at finding viable replacements.

Peptides provide an attractive alternative route to developing this type of ligand. Non-ribosomal proteins such as cyclosporine are peptidic compounds that incorporate amino acids beyond the 20 common residues coded for by DNA. These molecules are capable of modulating intracellular protein-protein interactions (PPI), and exhibit oral bioavailability. However, there have been a limited number of therapeutic molecules derived by searching natural products. Ho, S. et al. (1996) Clin. Immunol. And Immunopathol. 80:S40; Baumann et al. (1994) Protein Sci. 3:750; and De La Cruz et al. (1996) Biochem. 35:14054.

Selection methods such as mRNA display and phage display have been shown to be capable to generating peptidic ligands able to bind to and modulate PPI for a very large variety of protein interactions. Ja et al. (2004) Biochemistry 43:9265; Ja et al. (2006) ACS Chem. Biol. 1:570; and Millward et al. (2007) ACS Chem. Biol. 2:625. However, these peptides suffer from poor bioavailability due in large part to proteolysis.

A more traditional approach to peptide medication and drug development requires the generation of a lead molecule followed by extensive medicinal experimentation. Present current strategies include helix stapling, peptoid synthesis, beta-peptide generation, and N-methyl incorporation. Fiacco, S. V. and Roberts, R. W. (2008) ChemBio Chem 9:2200; Walensky et al. (2004) Science 305:1466; Miller et al. (1994) Bioorganic & Medicinal Chem. Letters 4:2657; and Nguyen, J. T. et al. (1998) Science 282:2088. However these techniques are very labor intensive, often taking years, with no guarantee of success. Many times the resulting product will exhibit a loss in function, specificity, or both.

Previous attempts to stabilize and enhance protease stability of a peptide include chemically scanning each of the 9 positions with an N-methyl analog. Four (4) of the 9 positions enhanced protease resistance indicating that a single N-methyl provided a window of protection around the scissile bond. The resulting protease resistance was dramatic, ranging from 70 fold to over 1000 fold at the site of cleavage. Unfortunately only one of the 9 substitutions retained the same binding specificity as the parent molecule; 4 of the sequences lost function while 4 had altered specificity now binding the related protein Gα12 instead of the original target, gαi1. Interestingly combining the two best Gα12 binding modifications resulted in a total loss of function (Fiacco et al. (2008), supra).

Another approach involved making covalent cyclic mRNA display libraries that had the unnatural amino acid N-methyl phenylalanine (NMF). That work showed that cyclic peptides could have antibody like affinity and that cyclization improved stability. However, the increase in protease resistance was modest (2.6 fold) and the resulting molecules lacked the unnatural amino acid (Millward et al. (2007) supra; Frankel et al. (2003) Chemistry & Biology 10:1043 and Gilmore et al., In *Implementation and Redesign of Catalytic Function in Biopolymers*; Springer Berlin/Heidelberg (1999) 202:77). Additionally Phe is a large residue and may be compatible in only a few of the positions.

Thus, a need exists to devise a scheme that retains the binding function of a natural peptide while dramatically improving its stability both in vitro and in vivo, that can be applied to any target of interest, thereby overcoming the limitation of the helix stapling methods described by Walensky et al. (2004), supra., which can only be applied to some helical structures.

A need also exists for new approaches to target unmet medical needs. Diabetes is an example. Diabetes can be divided into two categories. Type 1 diabetes is characterized by individuals with the inability to create insulin. This form of diabetes is a progressive disease characterized by significant loss in pancreatic β-cell mass leading to impaired insulin secretion. Impaired insulin secretion results in hyperglycemia which can lead to serious health problems such as ketoacidolysis if left untreated. Iyer, H., et al. (2010) Diabetes, Obesity and Metabolism 12:179. Type 2 is characterized by the inability to properly utilize insulin. Long term misregulation of blood sugar leads to an increased risk of heart failure, kidney disease, strokes, and limb amputation. Ford, E. S. Journal of Diabetes Ford, E. S. (Jul. 8, 2011). In the United States, more than 90% of individuals with diabetes have type 2 diabetes. WebMd 2011, available at the web address: diabetes.webmd.com/guide/type. Currently, diabetes is the seventh leading cause of death in the United States. Center for Disease Control 2011, available at the web address: www.cdc.gov/diabetes/pubs/estimates11.html.

According to the World Health Organization as of 2011, approximately 220 million people, or 3.2% of the world population, have diabetes. This number is expected to increase to 4.4% of the overall world population by 2030. Goldberg, M., et al. (2003) Nat Rev Drug Discov. 2:289. Diabetes becomes more prevalent with age, effecting 18.3% (8.6 million) of Americans over 60 years old (Center for Disease Control 2011, available at the web address: www.cdc.gov/diabetes/pubs/estimates 11.html).

There is a significant precedent for the development of peptides that are capable of binding protein surfaces with high affinity and specificity for the purpose of controlling protein-protein interactions in vitro. Ja, W. et al. (2006) ACS Chem. Biol. 1:570; Karatan, E. et al. (2004) Chemistry & Biology 11:835; Fuh, G. et al. (2000) J. Biol. Chem. 275:21486; and Stoop, A. A. and Craik, C. S. (2003) Nat Biotech 21:1063. However, their development into orally bioavailable therapeutics or therapeutics able to reach intracellular targets remains a tremendous challenge. This is due in part to the intrinsic difficulties these types of ligands face in crossing lipid bilayers. Morris, M. C. et al. (23001) Nat Biotech 19:1173; Goldberg, M. and Gomez-Orellana, I. (2003) Nat Rev Drug Discov. 2:289. There are examples pharmacologically relevant peptidic ligands that are thought to passively diffuse across cell membranes such as cyclosporine, amanitin, and phalloidin. Ho, S. et al. (1996) Clinical Immunology and Immunopathology 80:S40; Baumann, K. et al. (1994) Protein Sci. 3:750.; and De La Cruz, E. M. and Pollard, T. D. (1996) Biochemistry 35:14054.

Current biological treatments for diabetics typically center around the injection of various insulin products. Sales of insulin and insulin analogs resulted in over $15 billion in revenue in 2010. Currently, there is no FDA approved oral formulation for insulin. Developing an oral route to insulin administration would be a tremendous benefit to those affected by the diabetes, not only because of convenience, but also due to potential health benefits of this route of administration. After secretion from the pancreas, insulin travels to the liver before dispersion to the rest of the body. Orally absorbed drugs follow this same route; however drugs administered by injection do not. It is postulated that an oral treatment would alleviate adverse side effects of insulin administration such as weight gain and hypoglycemia. Funnell, M. M. (2006) Clinical Diabetes 24:154.

Effective treatment of diabetes also is hindered by low patient compliance. Today, insulin is administered by self-injection. An orally bioavailable drug would enhance patient compliance. However, orally administered drugs, such as peptidic ligands, are hindered by the facts that peptidic ligands must reach their targets to be effective diagnostically or therapeutically. Additionally, intracellular proteins must cross the plasma membrane and bioavailable peptides must traverse the intestinal mucosa to reach their targets. This invention addresses the limitations of the current state of the art.

SUMMARY

In one aspect, Applicants provide a method for selecting one or more nucleic acids from a library of nucleic acids that encode one or more stable and bioavailable peptide(s), comprising, or alternatively consisting essentially of, or yet further consisting of, selecting from a nucleic acid library one or more nucleic acids encoding stable and bioavailable peptide(s), wherein one or more members of the nucleic acid library contain one or more unnatural amino acids and/or codon lacking natural cognate tRNAs.

In another aspect, this invention provides a method for selecting one or more peptides that possess secondary structure. This method comprises, or alternatively consisting essentially of, or yet further consist of, the steps of generating a library of peptides and selecting individual sequences from the library by treating the library with one or more proteases, thereby selected for one or more peptides with secondary structure. In one aspect, the nucleic acid is an RNA and/or the library is an RNA library. In a further aspect, the method further comprises supplementing the library with one or more tRNA comprising an amino acid to suppress the stop codon. The members of the mRNA library are linear and/or cyclic.

In another aspect, a method is provided for preparing one or more nucleic acids that encode peptide(s), comprising the steps of mutating a library of peptides selected for a pre-determined specificity to incorporate amino acids that impart stability; incorporating one or more stop codons; supplementing tRNA charged with the desired amino acid to suppress the stop codon; cyclizing one or more of the individual sequences of the nucleic library; selecting individual sequences of the library for protease resistance, thereby selecting for one or more nucleic acids that encode one or more peptide(s). In one aspect, the nucleic acid library is a DNA library or a RNA library. In one aspect, the method further comprises translating the one or more nucleic acids to a peptide. In a further aspect, the method further comprises conjugating the peptide to a biotin molecule or biotin analog through a linkage. Non-limiting examples of biotin molecules or biotin analogs are one or more of a reducible biotin molecule; a biotin on the side chain of lysine of the peptide; a biotin linked to the peptide through an amide linkage or an ester linkage, a biotin linked to the peptide through a thioester linkage or an ester linkage. In a further aspect of the method, the nucleic acid is isolated. The nucleic acid is optionally translated into the encoded peptide or protein and further isolated. The isolated molecules are further provided by this invention.

Peptides generally have poor stability and bioavailability in vivo. Here, Applicants provide methods to prepare one or more RNA that encode one or more stable and bioavailable peptide(s) by selecting individual sequences from an mRNA library, wherein the library contains nucleic acids encoding peptides selected for pre-determined specificity and stability, thereby selecting for one or more RNA that encode one or more stable and bioavailable peptide(s). In one aspect, the one or more members of the RNA library have one or more stop codons. In another aspect, the methods further comprise supplementing the library with one or more tRNA charged with the desired amino acid(s) to suppress the stop codon. In another aspect, one or more members of the mRNA library is linear or cyclic In one aspect, one or more members of the mRNA library have a single amino acid that confers stability, e.g., an N-methyl amino acid, an AIB, a D-amino acid or a beta (B) amino acid, or one that confers unique functionality on a side chain in such as manner as to derive functional peptides that exhibit drug like stabilities in vitro and in vivo. By selecting for example, protease resistance, e.g., resistance to a caspase, an endopeptidase, an aminopeptidase, trypsin, thrombin, pepsin, chymotrypsin and proteinase K resistance, Applicants are able to derive peptides that are not only stable to a broad spectrum of proteases, but also stable to other drug processing enzymes such as cytochrome P450s. Additionally, simple modifications provide significant increases to in vivo half-life, as well as significant oral bioavailability. This approach provides a general method to the rapid development of highly stable peptides for therapeutic development and diagnosis.

In one aspect, on the DNA level, the library is designed to either code for the wild type amino acid or an amino acid that confers stability on the peptide, e.g., one or more of an N-methyl amino acid, an AIB, a D-amino acid or a beta (B) amino acid, or one that confers unique functionality on a side chain. In doing so, other amino acids are coded for as a byproduct. This provides library diversity. The DNA library optionally also has a codon coding for methionine (Met) at the 5' end, and a codon encoding lysine (Lys) at the 3' end. Typical mRNA display design can be employed from that point on. The lysine also can be used in cyclization. Chemically acylated (charged) tRNA with the N-methyl amino acid is designed to suppress a stop codon within the sequence, e.g., the stop codon UAG. This is supplemented to a typical translation mixture (e.g., rabbit retulocyte lysate).

Extra selective pressure can be applied for stabilized peptides (peptides chemically linked to their encoding mRNA named fusions). Translated products are subject to protease degradation e.g., the immobilized, purified proteases proteinase K, chymotrypsin, aminopeptidase, and trypsin. After proteolysis, proteases can be removed from fusions by filtration.

Additional selection pressure can be applied. For example, selection can be performed against human cells from a cancer patient that overexpressed a protein such as Her-2. In this example, the target is a human protein with post-translational modifications relevant in the disease state. This is a significant technological advance because the method and the peptides selected by its use allows the targeting of proteins that contain post-translational modifications in the disease state and proteins that are difficult to overexpress or purify.

For each of the above methods that require a selection, this invention provide several selection methods. Non-limited methods include selecting against a cell surface protein; selecting against mammalian cell culture or tissue; selecting against a purified protein target; selecting against a purified protein target that is a SUPR target; selecting for an in vivo therapeutic utility such as one or more of: the ability to inhibit the growth or kill a cancer cell, the ability to inhibit or kill a pre-cancerous cell or to bind to a cell expressing a desired target receptor.

In one aspect, the disclosure also provides an isolated RNA library prepared by the methods as described herein or an isolated peptide library prepared by a method described above. In another aspect, the disclosure provides an isolated peptide prepared by a method described herein.

The libraries, peptides and nucleic acis can be combined with a carrier, such as a pharmaceutically acceptable carrier.

This disclosure also provides non-naturally occurring peptides comprising amino acid sequences of the group:
1) MAVYVHYHK, wherein Position 1 is selected from Met, norvaline, alanine, or norleucine; Position 2 is selected from Ala or V, M, S, T, H, K, R, Q, N, L, V, or I; Position 3 is selected from N-Methyl Norvaline, S, T, Q, N, H, P, I, V, L, Y, F, or P; Position 4 is selected from Tyr, V, Y, F, Q, N, S, T, or H; Position 5 is selected from N-Methyl Norvaline, Y, F, S, T, E, D, M, A, or P; Position 6 is selected from His, V, Y, F, Q, or N; Position 7 is selected from His, V, F, Y, V, I, or L; Position 8 is selected from His or any amino acid; and Position 9 is selected from Lys or lysine derivatives, e.g., Orn (SEQ ID NO: 1);

2) MFVQVYYHK, wherein Position 1 is selected from Met, norvaline, norleucine, or alanine; Position 2 is selected from Phe or any amino acid; Position 3 is selected from N-methyl norvaline, Q, N, S, T, H, Y, F, or P; Position 4 is selected from Gln, Y, F, V, P, S, or T; Position 5 is selected from N-methyl norvaline, Y, F, S, T, D, E, A, or M; Position 6 is selected from Tyr, F, or H; Position 7 is selected from Tyr, F, L, I, V, S, T, or V; Position 8 is selected from His, T, or S; Position 9 is selected from Lys or lysine derivatives, e.g., Orn (SEQ ID NO: 2);

3) MLHYVYVRK, wherein Position 1 is selected from Met, norvaline, norleucine, or lanine; Position 2 is selected from Leu, I, or V; Position 3 is selected from His, Y, or F; Position 4 is selected from Tyr or F; Position 5 is selected from N-methyl norvaline, S, T, D, E, A, M, or P; Position 6 is selected from Tyr, H, Q, N, L, I, V, or V; Position 7 is selected from N-methyl norvaline, F, Y, L, I, V, H, or P; Position 8 is selected from Arg or any amino acid; Position 9 is selected from Lys or lysine derivatives, e.g., Orn (SEQ ID NO: 3);

4) MVCVVLYDDK, wherein Position 1 is selected from Met, norvaline, norleucine, or alanine; Position 2 is selected from Val, I, or L; Position 3 is selected from Cys; Position 4 is selected from N-methyl norvaline, Y, F, P, D, E, or M; Position 5 is selected from N-methyl norvaline, Y, F, D, E, W, C, G, or P; Position 6 is selected from Leu, Y, F, V, V, I, P, or C; Position 7 is selected from Tyr, V, E, or D; Position 8 is selected from Asp, S, T, E, Y, F, A, P, or V; Position 9 is selected from Asp, E, G, L, I, or V; Position 10 is selected from Lys or lysine derivatives, e.g., Orn (SEQ ID NO: 4);

5) MEVYEYVSLK, wherein Position 1 is selected from Met, norvaline, norleucine, or alanine; Position 2 is selected from Glu or any amino acid; Position 3 is selected from N-methyl norvaline, P, D, E, F, Y, S, T, Q, or N; Position 4 is selected from Tyr, D, E, F, V, or P; Position 5 is selected from Glu, D, Y, F, P, or V; Position 6 is selected from Tyr, F, L, V, I, P, or V; Position 7 is selected from N-methyl norvaline, F, L, V, I, P, or V; Position 8 is selected from Ser or any other amino acid; Position 9 is selected from Leu or any other amino acid; Position 10 is selected from Lys or lysine derivatives, e.g., Orn (SEQ ID NO: 5);

6) MNEYVLYVLK, wherein Position 1 is selected from Met, norvaline, norleucine, or alanine; Position 2 is selected from Asn or any amino acid; Position 3 is selected from Glu, D, I, V, L, F, Y, P, or V; Position 4 is selected from Tyr, D, E, P, or V; Position 5 is selected from N-methyl norvaline, D, E, F, Y, G, C, or P; Position 6 is selected from Leu, Y, F, P, or V; Position 7 is selected from Tyr, F, V, I, or L; Position 8 is selected from N-methyl norvaline, S, T, Y, F, E, D, A, or P; Position 9 is selected from Leu, K, R, I, L, V, D, E, G, S, or T; Position 10 is selected from Lys or lysine derivatives, e.g., Orn (SEQ ID NO: 6);

and for each of the above, V is an N-methyl amino acid or any modified amino acid that confers stabilization to the peptide.

Also disclosed are peptide conjugates containing the above-noted non-naturally occurring peptides, host cells and compositions containing one or more of these peptides, polynucleotides, conjugates and/or host cells. Also disclosed are polynucleotides encoding the peptides, vectors and host cells containing these, as well as compositions containing any one or more of the peptides, peptide conjugates, host cells, polynucleotides, vectors, alone or in combination with each other. Any of the above-noted can be formulated into a composition comprising a carrier such as a pharmaceutically acceptable carrier. In one aspect, when the peptide targets the Her-2 receptor, a composition containing the peptide is useful to inhibit the growth of a breast cancer cell in vitro or in vivo. In one aspect, the contacting is in vivo and a therapeutically effective amount of the composition is administered. In a further aspect, the patient is a Her-2+ patient.

This disclosure also provides a simple, nontoxic peptidic modification that can be incorporated into peptides and proteins, in one aspect the peptides described herein, to facilitate their delivery across cellular membranes as well as facilitate oral uptake. In one aspect, the peptides comprise N- or C-terminal biotinylation which was discovered to result in enhancements of bioavailability up to two orders of magnitude. The peptides optionally also comprise a disulfide between the biotin and the peptide to enhance delivery to the target. This modification allowed for the efficient delivery of peptide cargo in mammalian cells, as well as a significant increase in oral delivery of a stable peptide, e.g., insulin.

Thus, in one aspect, the disclosure provides a peptide conjugate, comprising, or alternatively consisting essentially of, or yet further consisting of a peptide linked at the N- and/or C-terminal to a biotin molecule or biotin analog through a linker, which includes but is not limited to a disulfide linkage, an ester linkage or a amide linkage. In one aspect, the biotin is a reducible biotin molecule. Additional examples of possible biotin analogs are provided herein.

In a further aspect, the peptide is linked to biotin on the side chain of lysine of the peptide. The linkages provide peptides and proteins suitable for oral deliver and that facility intracellular delivery of the peptide or protein.

This disclosure also provides a method for inhibiting the growth of a breast cancer cell, comprising contacting the cell with an effective amount of a non-naturally occurring peptide, or the conjugate as described herein, or the composition as described herein. These compositions can also be used to treat breast cancer in subject in need thereof. Further provides id a method for detecting a breast cancer cell in a subject comprising administering to the subject one or more of a non-naturally occurring peptide as described herein, the conjugate as described herein, or the composition as described herein and then screening for the presence of the presence of any peptide bound to the breast cancer cell in the subject. In one aspect, the administered composition detectively labeled, e.g., with a fluorescent dye or a PET label. In one aspect, the human patient is HER2+ patient.

BRIEF DESCRIPTION OF THE FIGURES

FIG. 1A shows the design of an N-methyl library from cyclic GIBP (also indentified as "GiBP" herein) (SEQ ID NOS 19 and 51-52, respectively, in order of appearance). Boxed amino acids were found in the selected peptide. FIG. 1B shows a selection strategy including proteolysis.

FIG. 2A shows a selected peptide sequence (SEQ ID NO: 53). FIG. 2B is the chemical structure of cycGIBP. FIG. 2C is the chemical structure of an exemplary SUPR peptide. Location of N-methyl incorporation is illustrated in light gray scale, change in side-chain structure found in a darker gray scale.

FIG. 4A shows the predicted chymotrypsindigest sites with arrows above the sequence. Actual digest sites determined by MALDI-TOF and illustrated below the sequence. FIG. 4B shows the half-life of linGIBP(▲), cycGIBP(■), linSUPR(●), and cycSUPR(◆) for chymotrypsin digest. FIG. 4C shows the predicted proteinase k digest sites in red. Actual digest sites determined by MALDI-TOF and illustrated in blue (SEQ ID NO: 7). FIG. 4D shows the half-life of linGIBP(▲), cycGIBP(■), linSUPR(●), and cycSUPR(◆) for proteinase K digest. FIG. 4E shows human serum half-life of half-life of linGIBP(▲), cycGIBP(■), linSUPR(●), and cycSUPR(◆). FIG. 4F shows half-life stability to human liver microsomes for half-life of linGIBP(▲), cycGIBP(■), linSUPR(●), and cycSUPR(◆).

FIG. 5A is Vmax for chymotrypsin digestion of cycGIBP(●), linSUPR(◆), and cycSUPR(■). A close up of linSUPR and cycSUPR is embedded in the Figure to show the data in more detail. FIG. 5B is a Table showing values for Km and Vmax as derived by processing the data through Graphpad Prism 5.0. Both Km and Vmax are highly optimized for protease resistance in cycSUPR peptide when compared to cycGIBP.

FIG. 6A shows the sequence of a SUPR peptide (SEQ ID NO: 54) with fluorescein on the side chain of lysine. FA-SUPR peptide (SEQ ID NO: 55) has an additional modification to include palmitoleic acid on the side chain of a C-terminal lysine. FIG. 6B shows in vivo stability of cycGIBP(▲), linSUPR(■), cycSUPR(◆), and FA-cycSUPR(●). Y-axis shows percent peptide intact (undigested).

FIG. 7A shows percent oral bioavailability vs time after feeding mice biotinylated peptide by oral gavage. FIG. 7B shows percent oral bioavailability of cyclic peptide vs biotinylated cyclic peptide versus palmitoleic acid cyclic peptide. In FIGS. 7A and 7B, data represents the average of two points and error is shown as standard deviation.

FIG. 9 illustrates Her-2 N-methyl library design (9A) and the design of N-methyl library from cyclic GIBP (9B). Boxed amino acids were found in the winning peptide. V represents N-methyl norvaline (SEQ ID NOS 58, 60, 59 and 61, respectively, in order of appearance).

FIG. 11A shows fluorescent labeled HRAP is binding to SKBR-3 cells. Growth media, trypsin solution, and nonfunctional peptide all show signal at background. FIG. 11B shows that 200,000 cells bind to approximately 1.5 pmoles of peptide.

FIG. 13A shows a peptide taken from the Herceptin antibody loop was put in the context of a $MX_8K$ cyclic peptide and randomized as previously illustrated in FIG. 1 The amino acid sequence is shown above its chemical structure (SEQ ID NOS 62-63, respectively, in order of appearance). Insertion of N-methyl amino acids is highlighted in red, and other changes are shown in the chemical structure in blue. FIG. 12B shows a peptide taken from the Omnitarg antibody loop that was put in the context of a $MX_7K$ cyclic peptide and randomized as previously described (SEQ ID NOS 64-65, respectively, in order of appearance). The amino acid sequence is shown above its chemical structure. Insertion of N-methyl amino acids is highlighted in red, and other changes are shown in the chemical structure in blue.

FIGS. 17A to 17G show the biotin mediated transport of peptide across the plasma membrane. Images are the fluorescent channel followed by the light channel. FIG. 17A shows peptide sequences used incorporating a bridging disulfide between the biotin conjugate and the peptide (SEQ ID NOS 66-69, respectively, in order of appearance). FIG. 17B shows 3T3 cells incubated with peptide 1 overnight. FIG. 17C shows HeLa cells incubated with peptide 1 overnight. FIG. 17D shows 3T3 cells incubated with peptide 2 overnight. FIG. 17E shows HeLa cells incubated with peptide 2 overnight. FIG. 17F shows neurons incubated overnight with peptide 3. FIG. 17G shows neurons incubated overnight with peptide 4.

FIG. 20A shows percent oral bioavailability vs time after feeding mice biotinylated peptide by oral gavage. FIG. 20B shows percent oral bioavailability of cyclic peptide vs biotinylated cyclic peptide vs palmitoleic acid cyclic peptide. In FIGS. 20A and 20B, data represents the average of two points and error is shown as standard deviation.

FIG. 21A shows the site of biotinylation is on the N-terminus of the B-chain of insulin as determined by chymotrypsin digest and mass spec analysis. Sequences are disclosed as SEQ ID NOS 71-72, respectively, in order of appearance. FIG. 21B shows the insulin response from 4 mice having biotinylated insulin administered at 3.5 nmol/kg intravenously. FIG. 21C shows the insulin response from 4 mice having unmodified human insulin administered at a dose of 3.5 nmol/kg intravenously.

FIG. 22 shows blood glucose levels in vivo when mice are administered phosphate buffer (■), insulin (▲) at 7 ng/kg, or biotinylated insulin (♦) at 7 ng/kg. Points represent the average response for four mice and error is in SEM.

FIG. 25A shows that linGIBP (the starting peptide) has a CD profile indicating that it is entirely unstructured. FIG. 25B shows that cyclic SUPR peptide is highly structured, and seems to be helical. FIG. 25C shows that removal of the N-methyl amino acids results in a loss of helicity. FIG. 25D shows that linear SUPR peptide is also helical.

FIG. 26A shows a SUPR peptide having a helical profile. FIG. 26B shows that peptide D, of the Her-2 binding peptide family, shows a distorted helical structure. FIG. 26C shows that Peptide 7, of the Her-2 binding peptide family, shows a beta-turn structure. FIG. 26D shows that Peptide 1, of the Her-2 binding peptide family, has a beta turn profile very similar to cyclosporine (FIG. 26E). −10,000 mean molar ellipticity units correlates to approximately −2.7 mdeg units. Therefore not only are peptide 1 and cyclosporine have a similar shape, but also their degree of structure is very similar.

DETAILED DESCRIPTION

Figure 1A:
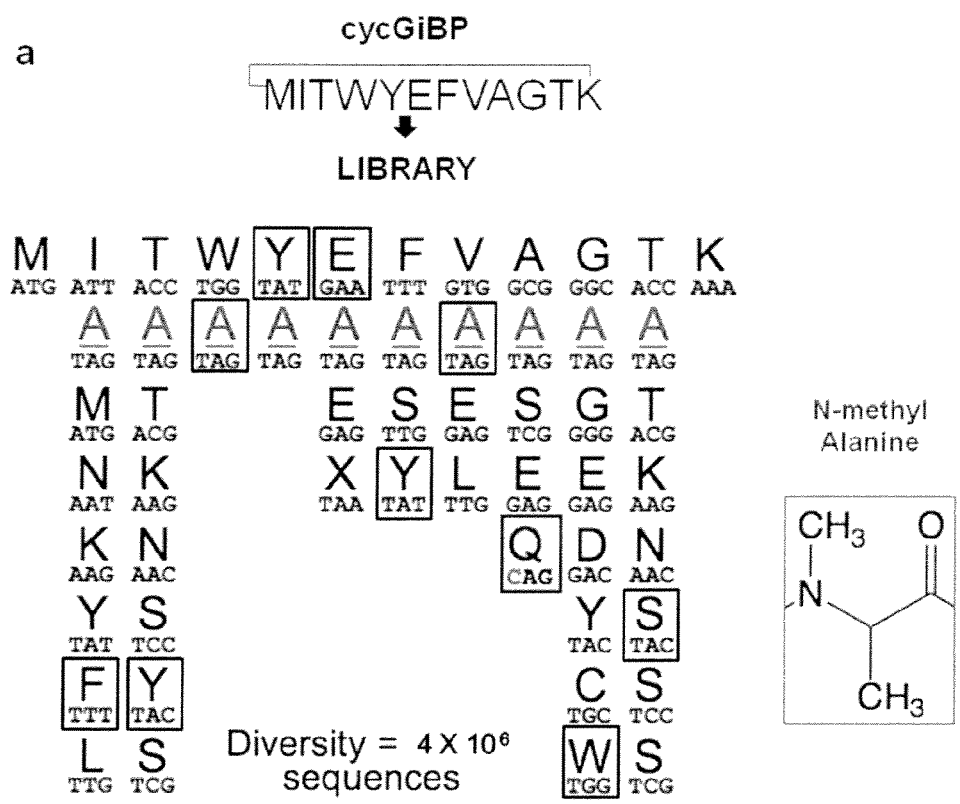
FIGS. 1A and 1B are general schematics of an N-methyl cyclic mRNA-display.

Unless defined otherwise, all technical and scientific terms used herein have the same meanings as commonly understood by one of ordinary skill in the art to which this invention belongs. All nucleotide sequences provided herein are presented in the 5' to 3' direction. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address://align.genome.jp/, last accessed on Mar. 7, 2011.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "stop codon" intends a three nucleotide contiguous sequence within messenger RNA that signals a termination of translation. Non-limiting examples include in RNA, UAG, UAA, UGA and in DNA TAG, TAA or TGA. Unless otherwise noted, the term also includes nonsense mutations within DNA or RNA that introduce a premature stop codong, causing any resulting protein to be abnormally shortened. For example, one can remove all the nucleotides encoding for valine, and then reduce in positions where they are not typically located within the wild-type sequence.

A "nonribosomal peptide" or "NRP" is a peptide that is not synthesized by the ribosome.

An intracellular PPI is an intracellular protein-protein interaction ("PPI").

As used herein, the term "pre-determined specificity" intends a peptide having a selected ability to specifically recognize and bind a pre-selected target, e.g., Her-2 receptor. Non-limiting examples of pre-selected targets include for example, any peptide, antigen, polynucleotide or antibody.

As used herein, the term "bioavailable peptide" means a peptide, polypeptide or protein that is capable of crossing the various biological barriers to reach target cells after its administration, and particularly to pass through the intestinal barrier after oral administration. Bioavailability is determined for a selected cell type as a function of the envisaged application. Methods for determining bioavailability are known in the art and described herein.

As used herein, the term "stable peptide" intends a peptide, polypeptide or protein that has a lifetime, once administered in vivo, which is sufficient to reach target cells and to exert its biological action. These peptides have a conformation which protects them against degradation by cell proteases while retaining biological activity. An indication of the stability of a peptide may be obtained using tests carried out in vitro. For example, in vitro degradation of a peptide is measured by contact with a variety of purified proteases, which are commercially available, for increasing incubation periods (1 hour to 72 hours, for example). Peptide degradation is then demonstrated by reverse phase HPLC, comparing the profiles obtained before and after digestion. In one aspect, the stable protein is more resistant to proteases present in human serum, e.g., more than about 20%, or alternatively, more than about 40%, or alternatively more than about 50%, or alternatively more than about 60%, or alternatively than about 70%, or alternatively more than about 75%, or alternatively more than 80% more resistant.

As used herein, the term "mRNA library" intends a plurality of at least two RNA members having a promoter region followed, by the amino acid Met, followed by a number of randomized amino acids (typically 7 to 10), followed by lysine.

A "biotin analog" as used herein intends a peptide sequence conjugated at or near the N or C terminus for the purpose of enhancing membrane permeability, cell penetration, and/or oral availability. Non-limiting examples of biotin analogs include, dehydrobiotin, iminobiotin, biotinamine, diaminobiotin, desthiobiotin, halogenated biotin, long chain biotin, and biotin-PEG. Methods to PEGylating peptides are known in the art and described, for example in Mero et al., *Bioconjugation Protocols Methods in Molecular Biology* 2011, Vol. 751, Part. 1, 95-129; and Gonen-Wadmanya et al. (2011) Biomaterials 32(26):6025-6033.

As used herein, the term "predetermined specificity" intends a selected ability to specifically recognize and bind a predetermined target, e.g., the Her-2 receptor.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT Publication No. WO 95/27071. Ads do not require integration into the host cell genome. Recombinant Ad derived vectors, particularly those that reduce the potential for recombination and generation of wild-type virus, have also been constructed. See, PCT Publication Nos. WO 95/00655 and WO 95/11984. Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. DNA virus, RNA virus, modifications, liposomes are non-limiting examples of vectors.

Gene delivery vehicles also include DNA/liposome complexes, micelles and targeted viral protein-DNA complexes. Liposomes that also comprise a targeting antibody or fragment thereof can be used in the methods of this invention. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$m, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) *Handbook of Fluorescent Probes and Research Chemicals* ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called an episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission.

Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen of the invention is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

Figures 2A, 2B, 2C:
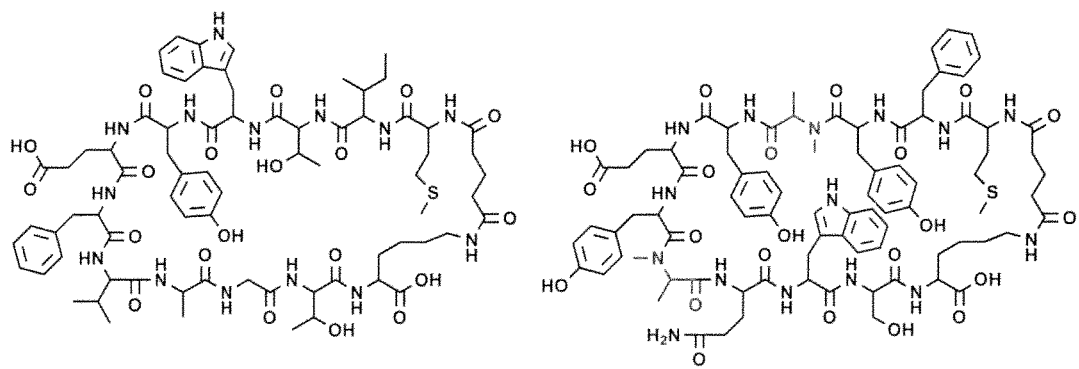
FIGS. 2A to 2C are exemplary Scanning Unnatural Protease Resistnt "SUPR" peptides.

"SUPR" is an acronym for "Scanning Unnatural Protease Resistant" peptide, examples of such are shown in FIG. 2. A specific example is the peptide MFYAYEYĀQWSK, wherein A is N-methyl alanine (SEQ ID NO: 7).

The term "oral uptake" is synonymous with oral bioavailability, which is the percent of a compound that gains access to the bloodstream after oral consumption.

MODES FOR CARRYING OUT THE DISCLOSURE

Methods, mRNA, Libraries, Polypeptides and Proteins

In one aspect, this invention provides a method for selecting one or more RNA members from an mRNA library, wherein the one or more RNA members encode one or more stable and bioavailable peptide(s). The method comprises, or alternatively consists essentially of, or yet further consists of, selecting from an mRNA library containing sequences encoding peptides, wherein one or more members of the mRNA library contain one or more unnatural amino acids and/or stop codons, and wherein the peptides encoded by the one or more members are selected for pre-determined specificity and stability, thereby selecting for one or more RNA that encode one or more stable and bioavailable peptide(s). Methods for selecting the one or members are described herein. Non-limiting examples include screening for an in vitro or in vivo function, such as protease resistance and/or the ability to bind to a pre-selected target such as the Her-2 receptor, the ability to disrupt a protein-protein interaction, and/or the ability to withstand enzematic modification.

This disclosure also provides a method for preparing one or more RNA that encode one or more stable and bioavailable peptide(s), comprising, or alternatively consisting essentially of, or yet further consisting of, mutating a library of peptides selected for a pre-determined specificity to incorporate amino acids that impart stability and then incorporating one or more stop codons. In another aspect, the method further comprises, or alternatively consists essentially of, or yet consists of, reverse translating the library of peptides to a RNA library; cyclizing one or more of the individual sequences of the RNA library; and selecting individual sequences of the mRNA library for protease resistance, thereby selecting for one or more RNA that encode one or more stable and bioavailable peptide(s). An example of a pre-determined specificity is the Her-2 antigen. Another example examined is GIBP binding to Gαi1. Any protein and binding partner could work. For example, a protein with an antibody, endogenous binding partner, peptide found by selection process such as ribosome, phage, or mRNA display are also within the scope of this invention. Amino acids that impart stability are known in the art and include without limitation, N-methyl amino acids. Examples of N-methyl amino acid include, but are not limited to N-methyl norvaline or N-methyl alanine or alternatively any modification to an amino acid that confers stabilization, e.g., proline, D-amino acids, Beta amino acids, peptoids, and 2-aminoisobutyric acid (Aib) or any amino acid not encoded for ribosomally. In one aspect, the one or more mRNAs are isolated from the library.

In one aspect, the method further comprises, or alternatively consists essentially of, or yet further consists of translating the one or more selected RNAs to a peptide.

Using the disclosed methods, stable peptides were generated. Thus, in one aspect this disclosure provides a non-naturally occurring peptide comprising, or alternatively consisting essentially of, or yet further consisting of an amino acid sequence of the group:

a) MAVYVHYHK, wherein Position 1 is Met or (norvaline, alanine, norleucine); Position 2 is Ala or (V, M, S, T, H, K, R, Q, N, L, V, I) Position 3 is N-Methyl Norvaline or (S, T, Q, N, H, P, I, V, L, Y, F, P); Position 4 is Tyr or (V, Y, F, Q, N, S, T, H); Position 5 is N-Methyl Norvaline or (Y, F, S, T, E, D, M, A, P); Position 6 is His or (V, Y, F, Q, N); Position 7 is His or (V, F, Y, V, I, L); Position 8 is His or any amino acid and Position 9 is Lys or (lysine derivatives e.g. Orn) (SEQ ID NO: 1);

b) MFVQVYYHK, wherein Position 1 is Met or (norvaline, norleucine, alanine); Position 2 is Phe or any amino acid; Position 3 is N-methyl norvaline or (Q, N, S, T, H, Y, F, P); Position 4 is Gln or (Y, F, V, P, S, T); Position 5 is N-methyl norvaline or (Y, F, S, T, D, E, A, M); Position 6 is Tyr or (F, H); Position 7 is Tyr or (F, L, I, V, S, T, V); Position 8 is His or (T, S); Position 9 is Lys or (lysine derivatives e.g. Orn) (SEQ ID NO: 2);

c) MLHYVYVRK, wherein Position 1 is Met or (norvaline, norleucine, alanine); Position 2 is Leu or (I, V); Position 3 is His or (Y, F); Position 4 is Tyr or (F); Position 5 is N-methyl norvaline or (S, T, D, E, A, M, P); Position 6 is Tyr or (H, Q, N, L, I, V, V); Position 7 is N-methyl norvaline or (F, Y, L, I, V, H, P); Position 8 is Arg or any amino acid; Position 9 is Lys or (lysine derivatives e.g. Orn) (SEQ ID NO: 3);

d) MVCVVLYDDK, wherein Position 1 is Met or (norvaline, norleucine, alanine); Position 2 is Val or (I, L); Position 3 is Cys, Position 4 is N-methyl norvaline or (Y, F, P, D, E, M); Position 5 is N-methyl norvaline or (Y, F, D, E, W, C, G, P); Position 6 is Leu or (Y, F, V, V, I, P, C); Position 7 is Tyr or (V, E, D); Position 8 is Asp or (S, T, E, Y, F, A, P, V); Position 9 is Asp or (E, G, L, I, V); Position 10 is Lys or (lysine derivatives e.g. Orn) (SEQ ID NO: 4);

e) MEVYEYVSLK, wherein Position 1 is Met or (norvaline, norleucine, alanine); Position 2 is Glu or any amino acid; Position 3 is N-methyl norvaline or (P, D, E, F, Y, S, T, Q, N); Position 4 is Tyr or (D, E, F, V, P); Position 5 is Glu or (D, Y, F, P, V); Position 6 is Tyr or (F, L, V, I, P, V); Position 7 is N-methyl norvaline or (F, L, V, I, P, V); Position 8 is Ser or any other amino acid; Position 9 is Leu or any other amino acid; Position 10 is Lys or (lysine derivatives e.g. Orn) (SEQ ID NO: 5);

f) MNEYVLYVLK, wherein Position 1 is Met or (norvaline, norleucine, alanine); Position 2 is Asn or any amino acid; Position 3 is Glu or (D, I, V, L, F, Y, P, V); Position 4 is Tyr or (D, E, P, V); Position 5 is N-methyl norvaline or (D, E, F, Y, G, C, P); Position 6 is Leu or (Y, F, P, V); Position 7 is Tyr or (F, V, I, L); Position 8 is N-methyl norvaline or (S, T, Y, F, E, D, A, P); Position 9 is Leu or (K, R, I, L, V, D, E, G, S, T); Position 10 is Lys or (lysine derivatives e.g. Orn), and for each of the above, V, is as disclosed above or alternatively, an amino acid that confers stability such as an N-methyl amino acid (SEQ ID NO: 6).

The peptides can be further modified by conjugating the peptide to a biotin molecule or biotin analog through a disulfide linkage or palmitoleic acid. Non-limiting examples of such include a reducible biotin molecule; a biotin on the side chain of lysine of the peptide; a biotin linked to the peptide through an amide linkage or an ester linkage. Methods to conjugate the peptide to biotin molecules and/or biotin analogs to the peptides are known in the art and are disclosed herein. Examples of such include without limitation, PEGylation, biotinylation or lipidation.

Additional specific examples of peptide conjugates comprise insulin or the amino acid sequence MFYAYEY AQWSKK-mod, wherein A is N-methyl alanine and K(mod) is lysine with a modified side chain including biotin, a biotin analog or palmitoleic acid (SEQ ID NO: 8).

This disclosure also provides conjugates, comprising a linear or cyclized peptide linked at the N- and/or C-terminal to a biotin molecule or a biotin analog through a suitable linkage, e.g., a disulfide linkage. In one aspect the biotin analog is a reducible biotin molecule. In an another aspect, the peptide conjugate, comprises a peptide linked to biotin on the side chain of lysine, or alternatively, a peptide linked to biotin through an amide linkage, or alternatively a peptide linked to biotin through an ester linkage. These peptide conjugates are suitable for oral delivery and therefore, formulations suitable for oral delivery also are provided herein.

Although not intending to be limited to the size of the peptide of the conjugate, some alternative embodiments include conjugates wherein the peptide comprises between 4 and 50 amino acids of insulin, or alternatively between 4 and 30 amino acids, or yet further between 4 and 100 amino acids. Examples of peptides include the amino acid sequences identified as 1 to 10 in Table 2.

Non-limiting examples of biotin analogs include, dehydrobiotin, iminobiotin, biotinamine, diaminobiotin, desthiobiotin, halogenated biotin, long chain biotin, and biotin-PEG. Methods to PEGylating peptides are known in the art and described, for example in Mero et al., *Bioconjugation Protocols Methods in Molecular Biology* 2011, Vol. 751, Part. 1, 95-129; and Gonen-Wadmanya et al. (2011) Biomaterials 32(26):6025-6033.

Alternatively, the peptide conjugates contain an unsaturated fatty acid in place of the biotin or biotin analog. An example of such is palmitoleic acid.

The peptide conjugates of this disclosure contain a peptide having a N-methyl amino acid (e.g., N-methyl alanine or N-methyl norvaline) modified peptide or a modified amino acid whose modification confers stability on the peptide. Examples of such are described herein.

In a further aspect, the peptide conjugates described herein comprise peptides wherein the amino acid sequence is cyclized from lysine to the N-terminus.

In another aspect the peptides and/or conjugates can be combined with a carrier, such as a pharmaceutically acceptable carrier, for diagnostic and/or therapeutic use.

In another aspect, the mRNA or the peptide is isolated. They can be further screened for an in vivo therapeutic utility, such as the ability to inhibit the growth or kill a cancer cell or a pre-cancerous cell. Methods to further screen the peptides for in vivo utility are disclosed herein.

Also disclosed is an isolated RNA library; an isolated peptide library; an isolated peptide; each prepared by the disclosed methods. These can be combined with a carrier, such as a pharmaceutically acceptable carrier, as disclosed herein.

For reproduction and expression of a polynucleotide, a peptide, a proteins and a polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins of this disclosure by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

Also provided by this application are the peptides described herein conjugated to a detectable agent for use in therapeutic or diagnostic methods. For example, detectably labeled peptides can be bound to a column and used for the detection and purification of antibodies. They also are useful as immunogens for the production of antibodies. The peptides of this disclosure are useful in an in vitro assay system to screen for agents or drugs, which modulate cellular processes. For example, detectably labeled peptides can be bound to a column and used for the detection and purification of antibodies.

It is well know to those skilled in the art that modifications can be made to the peptides of the disclosure to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides of the disclosure can be modified to include unnatural amino acids. Thus, the peptides may comprise D-amino acids, a combination of D- and L-amino acids, and various "designer" amino acids (e.g., .beta.-methyl amino acids, C-.alpha.-methyl amino acids, and N-.alpha.-methyl amino acids, etc.) to convey special properties to peptides. Additionally, by assigning specific amino acids at specific coupling steps, peptides with .alpha.-helices .beta. turns, .beta. sheets, .gamma.-turns, and cyclic peptides can be generated. Generally, it is believed that .alpha.-helical secondary structure or random secondary structure is preferred.

The peptides of this disclosure also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils.

The peptides of this invention can further comprise a carrier such as a pharmaceutically acceptable carrier. In one aspect, the carrier is one that is suitable for oral administration.

In one aspect, the peptides are useful for treating cancer or separately, regulating blood sugar or treating diabetes, prediabetes or an associated condition or disorder in a subject in need of such treatment, comprising administering to the subject an effective amount of a suitable peptide, polypeptide, polynucleotide, conjugate or composition of this disclosure. In one aspect, the subject is a human patient.

Also provided are method for determining if a candidate agent is a potential therapeutic suitable for oral administration, the method comprising administering the candidate agent to a subject and assaying for bioavailability, and comparing the bioavailability of the candidate agent with the bioavailability of the peptide conjugate of this disclosure, wherein the candidate agent is a potential therapeutic if the bioavailability of the agent is at least substantially the equivalent of that of the peptide conjugate of this disclosure.

Further provided are kits for determining if a candidate agent is a potential therapeutic suitable for oral administration, comprising, or alternatively consisting essentially of, or yet further consisting of, the peptide conjugate as described herein and instructions for use.

This disclosure also provides a pharmaceutical composition comprising or alternatively consisting essentially of, or yet further consisting of, any of a peptide, analog, mutein, or fragment of this disclosure, alone or in combination with each other or other agents, and an acceptable carrier or solid support. These compositions are useful for various diagnostic and therapeutic methods as described herein.

Polynucleotides

This disclosure also provides isolated or recombinant polynucleotides encoding one or more of the above-identified peptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides of the disclosure encode polypeptides or proteins having diagnostic and therapeutic utilities as described herein as well as probes to identify transcripts of the protein that may or may not be present.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See Sambrook, et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g. a mammalian cell, an animal cell (rat or mouse), a human cell, or a prokaryotic cell such as a bacterial cell, containing a polynucleotide encoding a protein or polypeptide or antibody.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this disclosure can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides or polypeptides of this disclosure. The genetically modified cells can be produced by insertion of upstream regulatory sequences such as promoters or gene activators (see, U.S. Pat. No. 5,733,761), or by insertion of the peptides of this disclosure.

The polynucleotides also can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide of this disclosure under conditions permitting hybridization (preferably moderately stringent hybridization conditions) of complementary single-stranded polynucleotides, or more preferably, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

The polynucleotides of this disclosure can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (1994)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

Alternatively, RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide of this disclosure are useful as hybridization probes or as an equivalent of the specific polynucleotides identified herein. Since the full coding sequence of the transcript is known, any portion of this sequence or homologous sequences, can be used in the methods of this disclosure.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region. More preferably, the probe is 85% identical to the corresponding gene sequence after alignment of the homologous region; even more preferably, it exhibits 90% identity.

These probes can be used in radioassays (e.g. Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide of this disclosure. Accordingly, this disclosure also provides a probe comprising or corresponding to a polynucleotide of this disclosure, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally preferred, so as to increase stability and selectivity of the hybrid, and thereby improving the specificity of particular hybrid molecules obtained. More preferably, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase. For illustration purposes only, a primer is the same length as that identified for probes.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Compositions

Compositions are further provided. The compositions comprise a carrier and one or more of an isolated mRNA of the disclosure, an isolated polypeptide of the disclosure, an isolated polynucleotide of the disclosure, a vector of the disclosure, an isolated host cell of the disclosure, or an antibody of the disclosure. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide of the disclosure, an isolated polynucleotide of the disclosure, a vector of the disclosure, an isolated host cell of the disclosure, or an antibody of the disclosure, formulated with one or more pharmaceutically acceptable auxiliary substances.

For oral preparations, any one or more of an isolated or recombinant polypeptide as described herein, an isolated or recombinant polynucleotide as described herein, a vector as described herein, an isolated host cell as described herein, can be used alone or in pharmaceutical formulations of the disclosure comprising, or consisting essentially of, the peptide or other agent of this disclosure in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated peptide of the disclosure, an isolated polynucleotide of the disclosure, a vector of the disclosure, an isolated host cell of the disclosure, can be formulated into preparations for administration in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other anticancer agents. For intravenous administration, suitable carriers include physiological saline, or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations of the disclosure comprise a peptide of the disclosure formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself (e.g. by an elastic bladder)).

Suppositories of the disclosure can be prepared by mixing a compound of the disclosure with any of a variety of bases such as emulsifying bases or water-soluble bases. Embodiments of this pharmaceutical formulation of a compound of the disclosure can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds of the disclosure. Similarly, unit dosage forms for injection or intravenous administration may comprise a compound of the disclosure in a composition as a solution in sterile water, normal saline or another pharmaceutically acceptable carrier.

Embodiments of the pharmaceutical formulations of the disclosure include those in which one or more of an isolated polypeptide of the disclosure, an isolated polynucleotide of the disclosure, a vector of the disclosure, an isolated host cell of the disclosure, or an antibody of the disclosure is formulated in an injectable composition. Injectable pharmaceutical formulations of the disclosure are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations of the disclosure.

In an embodiment, one or more of an isolated polypeptide of the disclosure, an isolated polynucleotide of the disclosure, a vector of the disclosure, an isolated host cell of the disclosure, or an antibody of the disclosure is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound of the disclosure can be accomplished using any of a variety of refillable, pump systems. Pumps provide consistent, controlled release over time. In some embodiments, a compound of the disclosure is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a peptide of the disclosure are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. After administration, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the peptide (as well as combination compositions) is delivered in a controlled release system. For example, a peptide of the disclosure may be administered using intravenous infusion, an implantable osmotic pump, a transdermal patch, liposomes, or other modes of administration. In one embodiment, a pump may be used (Sefton (1987) CRC Crit. Ref Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose.

In another embodiment, the compositions of the present disclosure (as well as combination compositions separately or together) include those formed by impregnation of a peptide described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Therapeutic Methods

Further provided are methods for treating a subject in need of treatment, comprising consisting essentially of, or yet further consisting of, administering to the subject an effective amount of a peptide obtainable by the methods of this disclosure, the conjugate, or a composition of this disclosure, or a combination of any thereof.

Also provided by this disclosure are therapeutic methods comprising, or alternatively consisting essentially of, or yet further consisting of, contacting a target cell, such as a cancer cell, with an effective amount of a peptide obtainable by the methods of this disclosure, the conjugate, or a composition of this disclosure, or a combination of any thereof. Contacting can be in vitro or in vivo. When performed in vitro, the method is a useful pre-clinical screen. When the method is performed in vivo in an animal such as a mouse or other animal model, it is a secondary pre-clinical screen for the testing of candidate agents.

Also provided by this disclosure are methods for regulating blood sugar or for treating diabetes or an associated condition or disorder in a subject in need of such treatment, comprising, or alternatively consisting essentially of, or yet further consisting of, administering to the subject an effective amount of a composition of this disclosure. In one aspect, the subject is a human patient, e.g., a patient suffering from diabetes or an associated condition.

Combination Therapy

The compositions and related methods of the present disclosure may be used in combination with the administration of other therapies, e.g., administration of a GLP-1 analog, described below. The additional therapeutic treatment can be added prior to, concurrent with, or subsequent to methods or compositions used to treat diabetes and/or related conditions, and can be contained within the same formulation or as a separate formulation.

Screening Assays

The present disclosure provides methods for screening for equivalent agents, such as equivalent peptides to a peptide or composition of this disclosure, and various agents that modulate the activity of the active agents and pharmaceutical compositions of the disclosure or the function of a polypeptide or peptide product encoded by the polynucleotide of this disclosure. For the purposes of this disclosure, an "candidate agent" is intended to include, but not be limited to a biological or chemical compound such as a simple or complex organic or inorganic molecule, a peptide, a protein (e.g. antibody), a polynucleotide (e.g. anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

Kits

Kits containing the agents and instructions necessary to perform the in vitro and in vivo methods as described herein also are claimed. Accordingly, the disclosure provides kits for performing these methods which may include peptides and/or other composition of this disclosure as well as instructions for carrying out the methods of this disclosure such as collecting tissue and/or performing the screen, and/or analyzing the results, and/or administration of an effective amount of a peptide or other composition as described herein. These can be combined with other known or other candidate agents.

The following examples are intended to illustrate, and not limit, the disclosures disclosed herein.

Experiment No. 1

This experiment describes the synthesis and screening of mRNA libraries that encode protease resistant peptides and synthesis of peptides for oral administration.

Gαi1 Expression and Immobilization.

2 L Gαi1 was expressed with a C-terminal BirA tag in the XL-10 gold strain of *E. Coli* under standard conditions. 50 mL aliquots of the growth were spun down at 6000 rpm at 4° C. and the pellets were washed with ice cold PBS and stored at −80° C. Prior to each round of selection, a pellet is lysed with 1 mL of BPER. 120 uL of NeutrAvidin agarose beads are used for immobilization. Immobilization takes place in binding buffer with 1 mM PMSF for 1 hr at 4° C. The remaining biotin binding sites are quenched by the addition of 1 mM biotin for 30 min. The beads are then stored in binding buffer at 4° C. for up to one week.

THG73 tRNA Preparation.

The sequence 5'-ATT ATG CTG AGT GAT ATC CAA GAT ATC ATA TCG CCA ATC ATG ACC CCT GAG ATT TAG GGA ACT GGA CCC AAG CTT AGG GTC ATC CTG GAG-3' (SEQ ID NO: 9) was ordered PAGE gel purified from Integrated DNA Technologies. Standard transcription was accomplished by T7 runoff transcription and purified by urea-PAGE.

NMA-tRNA.

The synthesis of N-methyl, N-nitroveratrylcarbonyl alanine cyanomethyl ester was carried out according to the published protocol, see for example Millward et al. (2007), supra. The final product was purified by silica gel chromatography in 3:1 EtOAc/hexanes. Yield 187.5 mg (24%). The synthesis of N-methyl, N-nitroveratrylcarbonyl alanine-dCA was carried out according to Millward et al. (2007), supra. Yield % 0.5 mg (2.5%). Following ligation to THG-73 tRNA, deprotection of the nitroveratryloxycarbonyl group was effected by photolysis with a xenon lamp equipped with a 315-nm cutoff filter, and the NMAtRNA was immediately added to the translation reaction.

Synthesis of N-Methyl Scanning Library.

Single-stranded DNA template was ordered from Integrated DNA Technologies and the sequence was is 5'-GGG ACA ATT ACT ATT TAC AAT TAC AAT GWW KWM STR GTA KKA RTW KKW GKM GKR SWM SAA ATC TGG AAG TGG AAG TGG A-3' (SEQ ID NO: 10) using machine mixing for variable positions (W=A or T, K=G or T, M=A or C, R=G or A, S=G or C). The double stranded library was produced and amplified by performing 6 cycles of PCR on 1 pmole of PAGE gel purified single-stranded library. PCR was performed under standard conditions utilizing the primers Gen-FP (5'-TAA TAC GAC TCA CTA TAG GGA CAA TTA CTA TTT ACA ATT ACA-3' (SEQ ID NO: 11)) and the reverse primer (5'-CCA CTT CCA CTT CCA GAT TT-3' (SEQ ID NO: 12)).

The Round 0 mRNA pool was generated by T7 runoff transcription and purified by urea-PAGE. The purified mRNA was ligated to F30P (5=–dA21[C9]3dAdCdC-P (SEQ ID NO: 74); C9 tri-(ethylene glycol) phosphate (Glen Research), P puromycin (Glen Research)), via an oligonucleotide splint (5'-TTT TTT TTT TTT TCC ACT TCC ACT-3' (SEQ ID NO: 13)). Ligation was urea-PAGE purified and quantified by absorbance at 260.

Translation and Cyclization.

50 pmol of ligation was translated in rabbit reticulocyte lysate under standard conditions. The translation reaction was supplemented with 20 ug of NMAtRNA-CUA in 1 mM NaOAc (pH=4.5) and 35S-methionine. After 45 min of translation at 30° C., KOAc and MgOAc were added to a final concentration of 600 and 50 mM, respectively, and the reactions were incubated at room temp for 15 min. Translation mixtures were diluted 1:5 in dT binding buffer (10 mg mL*1 dT cellulose, 1 M NaCl, 20 mM Tris, 1 mM EDTA, 0.2% (v/v) Triton X-100, pH 8) and agitated for 45 min at 4° C. The dT cellulose was filtered and washed with dT wash buffer (300 mM NaCl, 20 mM Tris, pH 8). The conjugates were eluted with water and ethanol precipitated in the presence of linear acrylamide (Ambion). The round 0 pool was cyclized by adding 150 uL of dTpurified fusions in 50 mM phosphate buffer (pH 8) to 50 μL of DSG (1 mgmL/1 in DMF). The reaction was allowed to proceed for 1 hour, and the fusions were repurified by ethanol precipitation.

Selection.

Following ethanol precipitation of the round 0 DSG treated fusions, the pellet was dissolved in 100 μL of dH$_2$O and reverse transcribed with Superscript II under standard conditions. Following reverse transcription, the library was diluted 2 fold into 50 mM potassium phosphate buffer (pH=8.0). Round 0 digest used 1 mg of immobilized trypsin, 1 mg of immobilized chymotrypsin, 1 mg of immobilized proteinase K, and 1 mg of immobilized aminopeptidase for 20 min at room temp. All immobilized proteases were purchased from Sigma. Subsequent rounds used only immobilized chymotrypsin and proteinase K for proteolysis. Fusions were purified from proteases by spin filtration.

Digested fusions were put into 1.5 mLs of binding buffer (25 mM HEPES-KOH (pH % 7.5), 150 mM NaCl, 0.05% (v/v) Tween-20, 1 mM EDTA, 5 mM MgCl2, 10 μM GDP, and 0.05% (w/v) bovine serum albumin) containing 20 μL of Gαi1-NeutrAvidin agarose (preblocked with biotin). The binding reaction was carried out at 4° C. for 1 hour. The reaction was filtered, and the resin was washed four times with 1× selection buffer. The library was eluted with 0.15% (w/v) SDS at RT, and the SDS was removed from the sample using SDS-Out (Pierce). Following ethanol precipitation, the library was amplified by PCR. PCR amplification of the eluted library members was carried until band was observed on a 4% agarose gel (18-24 cycles).

The round 5 pool was amplified by PCR and was subcloned into the TOPO-TA vector (Invitrogen) followed by transformation into TOP10 competent cells (Invitrogen). Individual clones were sequenced (Laragen).

Peptide Synthesis.

All solvents were purchased from Sigma. C-terminally biotinylated SUPR peptide was synthesized on Novatag resing (250 mgs, 0.12 mmoles, EMD Biosciences). Palmitoleic acid conjugated SUPR was synthesized on Wang resin preloaded with D-Lys (250 mgs, 0.1 mmoles, Anaspec). All other peptides were synthesized using Rink Amide Am resin (250 mgs, 0.15 mmoles). Standard couplings were carried out with 5 eq. of monomer (Novabiochem) in (2 mL, 0.6 mMolar) HATU (Novabiochem) in DMF with (1.2 mMolar) DIEA at room temperature for 20 min. Coupling to an N-methyl amino acid followed the same procedure with the addition of HOAT (1.2 mMolar) and an extended coupling time of 30 min. Fmoc deprotection was carried out with 20% piperidine (Anaspec) at room temperature for 15 min. Following, deprotection, cleavage with 95% TFA, filtration and ether extraction, the crude product was purified on a Vydac C-18 reverse phase column using gradient elution (0% B for 5 min, 10-50% B in 40 min. Solvent A: H$_2$O with 0.1% TFA), Solvent B: CH$_3$CN with 0.035% TFA. Lyophilized solid was reconstituted in DMSO and quantitated by absorbance at 280 nm (ε280=9970 L mol-1 cm-1). Yield=10-25%. Cyclization of peptide (1 mg/mL) with 20 equivalents of disuccinimidyl glutarate (DSG, Pierce) was carried out in PBS with 70% DMSO at 42° C. overnight. Peptide was purified as previously described. Yield=15-25%

Specificity Analysis.

TNT pulldown experiments were carried out as previously described in Stoop and Craik (2003) Nat. Biotech 21:1063. Equal amounts of each radiolabeled subunit were added to 10 μL of NeutrAvidin-agarose containing 15 pmol of prebound SUPR-Bio peptide in 1 mL of 1× selection buffer. Control NeutrAvidin-agarose was treated with DMSO alone. Binding reactions proceeded for 1 h at 4° C. followed by filtration and washing with 1× selection buffer. The matrix was analyzed by scintillation counting, and the percent bound was determined by the matrix counts divided by the total counts as determined by TCA precipitation.

R6A Competition/Equilibrium Binding.

The relative binding affinities of R6A and SUPR were determined by equilibrium competition experiments versus biotinylated R6A (Bio-R6A), and fits and midpoints were determined using GraphPad Prism 5.0 following previously established protocols, such as Fiacco et al. (2008), supra.

Protease Resistance Experiment.

Immobilized chymotrypsin and proteinase K purchased from Sigma. 250 nmoles of peptide in DMSO were added to 50 mM sodium phosphate buffer (pH=8.0) with a final DMSO concentration of 2% Immobilized protease was added (60 units of chymotrypsin agarose, or 6 units of proteinase K) was added at room temp for chymotrypsin, and 4° C. for proteinase K. Alaquotes were taken at various time points, filtered and injected onto a C-18 reverse phase column and separated by gradient elution (15-90% B in 25 min. Solvent A: 0.1% TFA in water. Solvent B: CH3CN (0.05% TFA). The area under the starting material peak was quantitated using the 32 KaratGold Software package (Beckman). The plotted values represent the mean of two experimental values, and the error bars represent the standard error of the mean. The graph was generated by fitting the data to a one phase exponential decay equation (GraphPad Prism 5.0).

Human Serum Digests.

Delipidated/lyophilized human serum was purchased from Thermo Scientific and reconstituted as per manufacturer's instructions. 250 nmoles of peptide in 50 μLs of sodium phosphate buffer (pH=8.0) with 10% DMSO was added to 1 mL of reconstituted serum and incubated at 37° C. 100 μL aliquots were taken at various time points and quenched in 300 μLs of acetonitrile. Samples were spun down and decanted to remove precipitate followed by dilution in water to 1.5 mLs. Samples were then analyzed by HPLC as described in the protease resistance experiment.

Human Microsome Digests.

Pooled, mixed gender human microsomes containing cytochrome P450's were obtained from Xenotech. 100 μL of microsomes were added to 500 μL of PBS buffer containing 250 nmoles of peptide with 1% DMSO. 50 μL aliquots were removed at various time points and worked up in the same manner as the human serum digests.

In Vivo Half-Life.

Peptides synthesized as previously described with an additional C-terminal lysine(FAM). 200 μL of peptide was administered by IV injection into the tail vein of C57BL6 mice at a dose of 10 mg/kg. 50 μL blood samples were taken at various time points by orbital bleeding using heparin coated capillary tubes and isoflurane for anesthesia. Samples are diluted to 600 μL in TE buffer (pH=8.0) then filtered by centrifugation through a 3000 MWCO filter. The flowthrough was analyzed on a Shimadzu RF-5301 PC fluorometer. Time points were integrated and analyzed using Prism 5.0 software.

Oral Bioavailability.

The following peptides were synthesized for oral administration: MFYVVYEYVQWSKK(FAM) (SEQ ID NO: 14), MFYVYEYVQWSKK(FAM)DK(Palmitoleic acid) (SEQ ID NO: 15), and MITWYEFVAGTKK(FAM) (SEQ ID NO: 16), wherein FAM is a lysine derivative containing fluorescein. All peptides were cyclized from the side chain to lysine to the N-terminus as previously described. Anesthetized C57BL6 mice had peptide administered at a dose of 10 mg/kg by oral gavage. After administration, mice were removed from isoflurane. At various time points, blood samples were taken by orbital bleeding as previously described. Peaks were normalized to a 15 minute time point from mice that had peptide administered by IV injection.

Quantifying Frequency of SUPR in R5 Pool.

The following DNA sequence 5'-biotin-TTT GGA CCA CTG CTA ATA CTC ATA CTA GTA AAA CAT (SEQ ID NO: 17) was the anticoding strand for FYVYEYVQWS (SEQ ID NO: 18) was ordered as a biotinylated oligo from Integrated DNA Technologies. Approximately 35 nmoles of DNA was immobilized to approximately 265 μL of NeutrAvidin agarose beads (Pierce). Transcription from round 5 was incubated with beads containing either SUPR DNA or beads without DNA. As a positive control, transcription for SUPR peptide was incubated with beads containing the complementary DNA. The library and the beads were rotated in DT Buffer (50 mM HEPES-KOH pH=7.5, 1 M NaCl, 1 mM EDTA, 0.05% Tween) for 1 hour at 4° C. Absorbance at 260 was taken before and after incubation with immobilized DNA.

DISCUSSION

This disclosure provides methods to isolate and produce peptides that are readily translated, and thus amenable for use in mRNA display. The peptides provided by these methods also exhibit a high level of generalized protease resistance. In one aspect, chymotrypsin and trypsin were incorporated because they are proteases that are abundant in the intestines. In another embodiment, aminopeptidase was chosen since its prevalence in human serum. In a yet further embodiment, proteinase K was incorporated for two reasons (1) as a surrogate for all proteases generally due to its broad specificity and (2) because N-methyl insertion provided a high level of proteinase K resistance as reported by Frankel et al. (2003) supra.

Figure 1B:
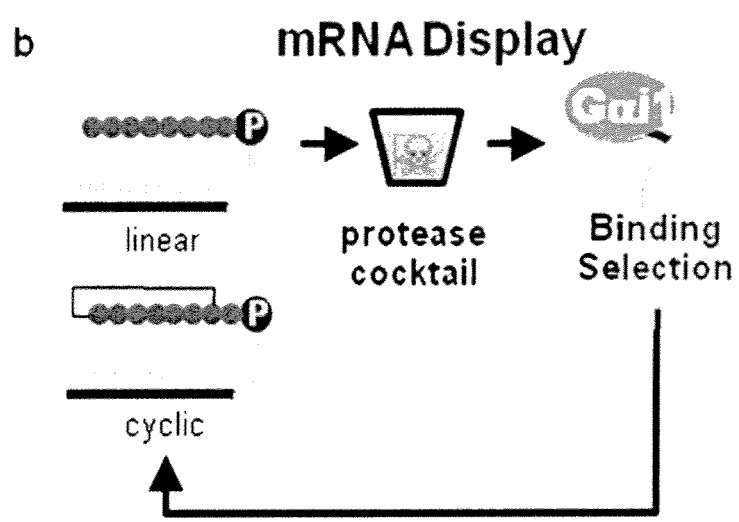

In one aspect, the method comprises scanning library based on cyclic GIBP (cycGIBP) although larger and smaller peptides can be used in the methods of this disclosure in which each position was systematically combined with either the wild type or UAG or other nonsense suppressor (see FIG. 1A). In addition, codons for natural amino acids could be used (e.g., valine). This resulted in a library with a primary sequence diversity with approximately $4 \times 10^6$. The library was designed such that members can contain 0 to 10 N methyl amino acids, with two being the most common. In addition to the N-methyl residues, this mutagenesis resulted in insertion of a number of natural sequences (FIG. 1A). Libraries were cyclized such that there was a mixture of linear and cyclic peptides, subjected to protease digestion, and selected for binding to the target (FIG. 1B).

The selection procedure can be repeated until a sufficient degree of binding between the peptides and the target is shown. In one aspect, sufficient binding was shown after 5 rounds of selection and the pool was subsequently sequenced. All of the 23 sequences found from this selection contained at least 1 NMA. The average quantity of NMA per peptide sequence increased in both the round 4 and round 5 pools with respect to the round zero pool. One sequence, MFYAYEYAQWSK (SEQ ID NO: 7) was found to dominate the pool. By pulldown, it was determined that approximately 35% of the sequences in the pool coded for this peptide. To the best of our knowledge, this is the first functional peptide derived by selection to incorporate unnatural amino acids for the enhancement of drug like characteristics. This peptide was attractive for other reasons as well. It incorporated a core motif of YEY that is similar to the core motif found in multiple other selections against Gαi proteins. The NMA residues are spaced apart, and predicted to provide a sufficient window of protease resistance predicted by previous predictive measures. There is also only a single lysine residue, indicating that there is only one possible cyclization. This molecule was named SUPR for scanning unnatural protease resistant peptide.

There are significant changes from the parental molecule to the selected molecule. 8 of the 10 possible positions for amino acid changes showed a change in sequence. Some of these changes, such as PHE and THR in cycGIBP to TYR and SER respectively, were conservative. However may other, such as the VAL and GLY of cycGIBP to GLN and TRP respectively, show a significant change in side chain functionality that would not have been predicted by analyzing sequences of Gαi1 binding peptides. A structural comparison can be made by observing sequence changes as outlined in FIG. 2.

Figures 3A, 3B, 3C, 3D:
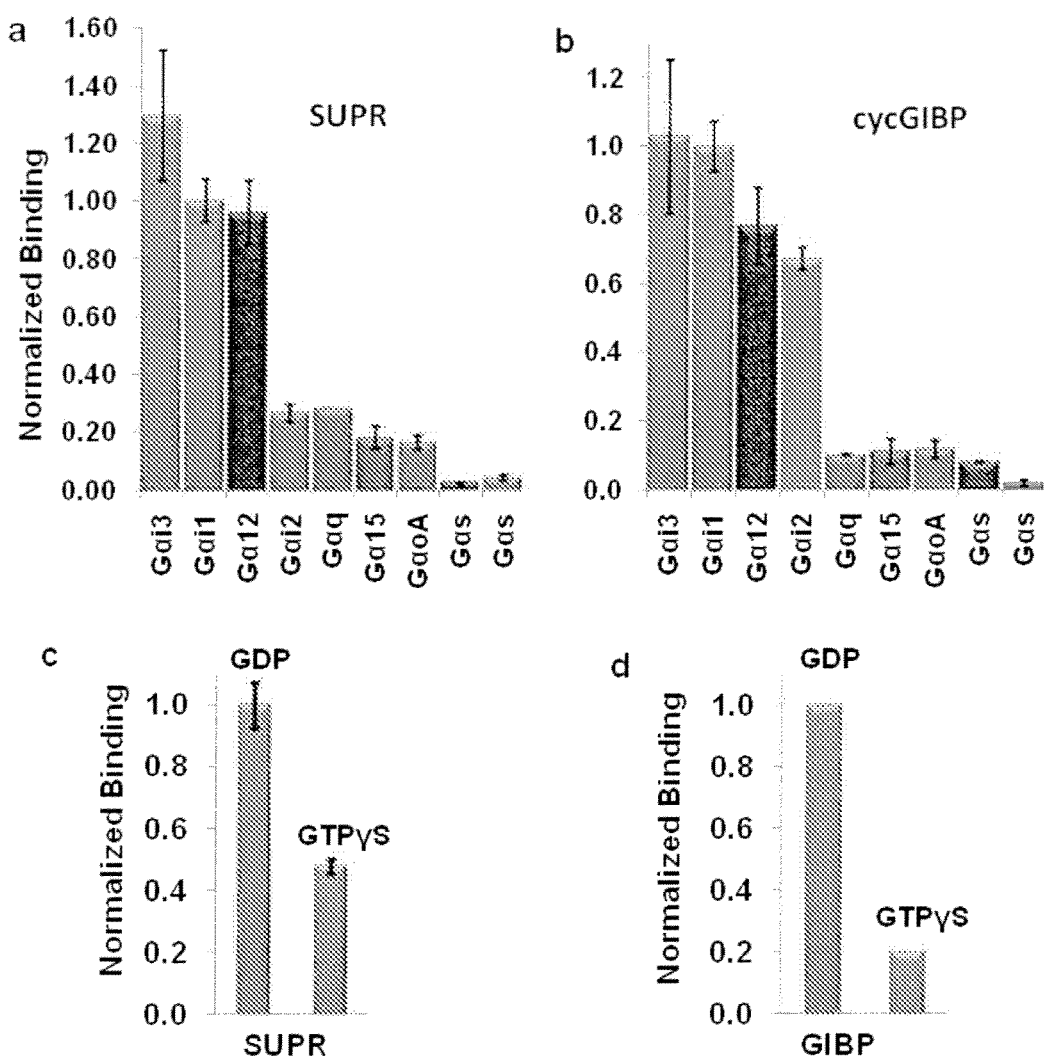
FIGS. 3A to 3D show that a SUPR peptide retained the selectivity of cycGIBP. NeutrAvidin-agarose was pretreated with (FIG. 3A) C-terminally biotinylated cycSUPR or (FIG. 3B) C-terminally biotinylated cycGIBP pulled down various radiolabeled Gα subunits. Binding is normalized to Gαi1 binding. Percent values represent the average of three experiments, and error is given in SEM see FIG. 3C. NeutrAvidin-agarose was pretreated with C) C-terminally biotinylated cycSUPR peptide or FIG. 3D) C-terminally labeled cycGIBP and incubated with Gαi1 in either the GDP state or the active GTP (GTPγS) state.

The peptide was characterized by utilizing standard pull down assays. cycSUPR peptide was synthesized incorporating a biotin at the C-terminus. The peptide was immobilized on NeutrAvidin-agarose and used to pull down radiolabeled protein. The efficiency of this pulldown was tested against multiple different Gα subunits. cycSUPR peptide retained specificity of its parent molecule as can be seen in FIG. 3. This was true both for specificity within the Gα family as well as state specificity of Gαi1. In fact, there was a small enhancement of specificity for the target Gαi1 over a protein with nearly 85% sequence similarity, Gαi2. The ability to match target specificity is in direct contrast to results from chemical incorporation of N-methyls which resulted in altered selectivity in 8 of 9 positions. The ability to retain or enhance selectivity for a desired target is of tremendous importance for therapeutic and diagnostic development. This data suggests that N-methyl incorporation into mRNA display will provide that ability.

Protease resistance enhancement was then tested. The simplest solution for enhancing protease resistance would be the removal of amino acids recognized by protease K and chymotrypsin. However, this peptide has roughly as many theoretical digest sites as the parent molecule. Upon digestion with proteinase K and chymotrypsin, SUPR peptide has seven and five theoretical digest sites, respectively. However, samples analyzed showed only 1 digest site from proteinase K and two from chymotrypsin. Proteolytic digestion revealed that SUPR cyclic peptide was approximately 5200 fold more resistant to proteinase K and 200 fold more resistant to chymotrypsin when compared to CycGIBP. Cyclization of SUPR enhanced protease resistance to both of these enzymes, suggesting a cooperate effect between cyclization and N-methylation as may be noted in FIGS. 4A to 4D.

These enhancements translated to stability when subject to human serum as well. Human serum is composed of more than 1500 proteins and hundreds of proteases. This is a close in vitro mimic to the in vivo environment a peptidic therapeutic would experience. Therefore for a peptide to be viable as a potential therapeutic, it must be stable to human serum. Current drugs, including peptidic drugs and monoclonal antibodies, show serum half-lives of days to weeks. Lin-GIBP and cycGIBP showed a half-life of approximately 0.14 hrs and 0.33 hrs respectively, far too quick to be predicted to be a potential drug candidate. LinSUPR also exhibited poor stability, with a half-life of only 0.27 hrs. This is likely due to some sort of exopeptidase activity, since it is generally known in the field that N-terminal alkylation and C-terminal amidation will help with stability. The incorporation of both cyclization and N-methylation found in cyc-SUPR peptide resulted in a very significant stability increase, generating a peptide with a 160 hr half-life in human serum shown in FIG. 4E. This data suggests that surviving chymotrypsin and proteinase K degradation is sufficient for conferring general protease resistance because neither active chymotrypsin nor proteinase K is found in human serum.

Figures 4A, 4B, 4C, 4D, 4E, 4F:
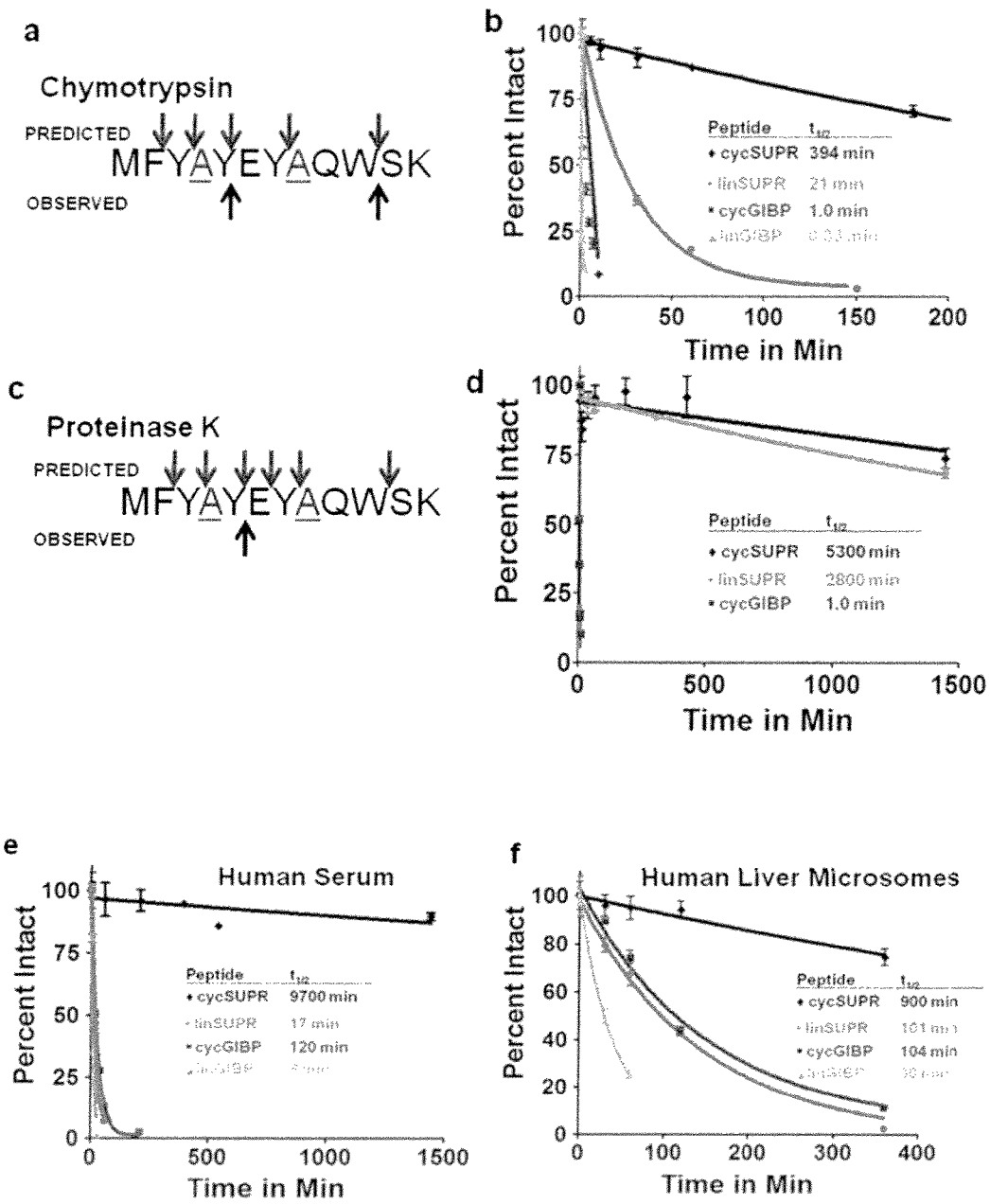
FIGS. 4A to 4F show that a selected SUPR peptide (SEQ ID NO: 7) is resistant to proteolysis.

Another vital area for the in vivo processing of drugs is the liver. All blood is eventually filtered through the liver, where various types of enzymes functionalize drugs for the purpose of excretion. The largest and most active class of liver enzymes involved in this process are the cytochrome P450s. These enzymes are largely involved in the oxidation of drugs, and can be found on the extracellular surface of the liver. Human liver microsomes are functional liver extract containing cytochrome P450s. Therefore half-life of modification of peptides by cytochrome P450s from exposure to human microsomes was examined. The results were similar to the human serum result in that both cyclization and N-methylation were necessary for significant enhancement of resistance to modification. In fact, there was nearly an order of magnitude increase in stability from either cycGIBP or linSUPR (similar half-lives) to cycSUPR as shown in FIG. 4F. This is interesting because the trait of protease resistance, not resistance to cytochrome P450 modification was a selection criteria. This suggests that the enhancements conferred by resistance to chymotrypsin and proteinase K will not only translate to general stability to proteases, but also to resistance to other classes of enzyme modification.

Figures 5A, 5B:
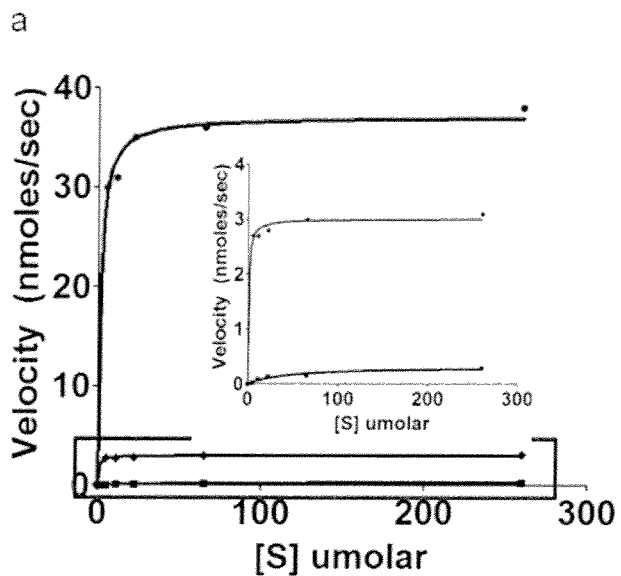
FIGS. 5A and 5B show cycSUPR optimized both Km and Kcat.
Figures 6A, 6B:
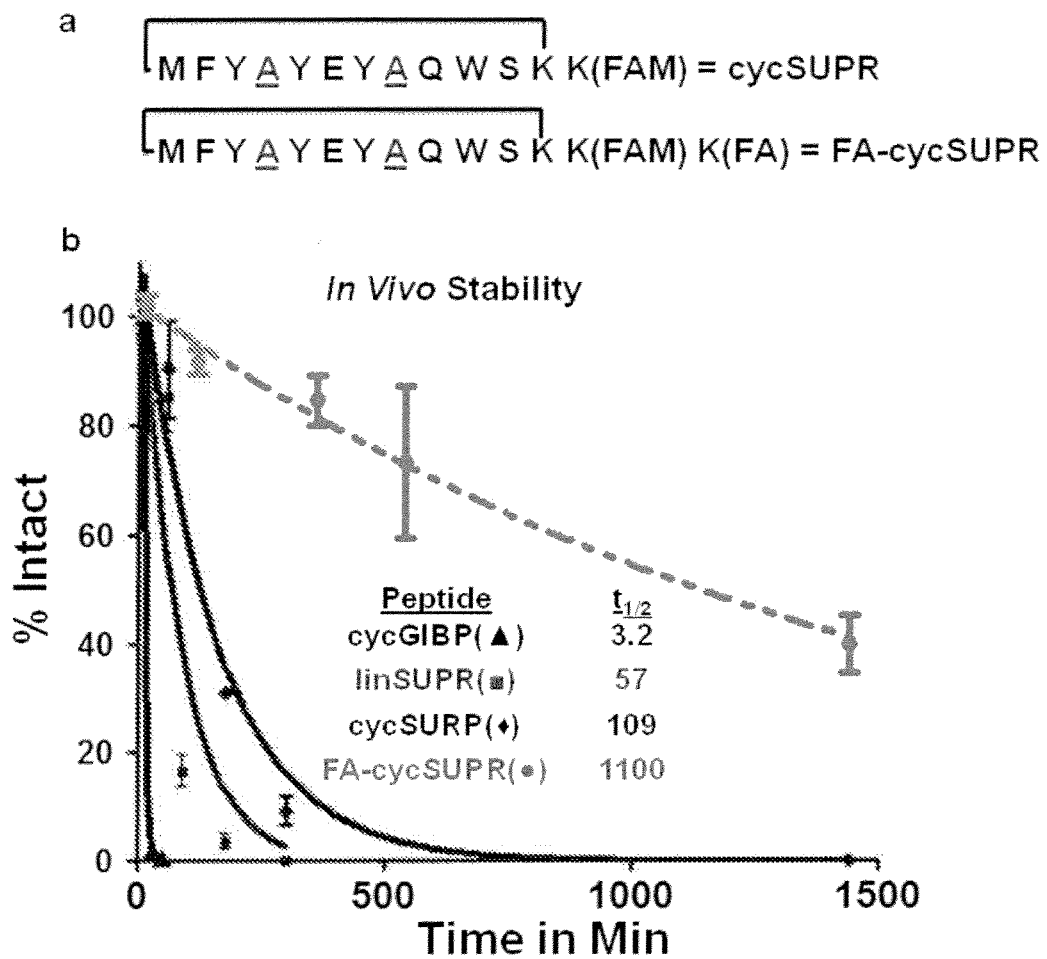
FIGS. 6A and 6B illustrate in vivo stability of a SUPR peptide.
Figures 7A, 7B:
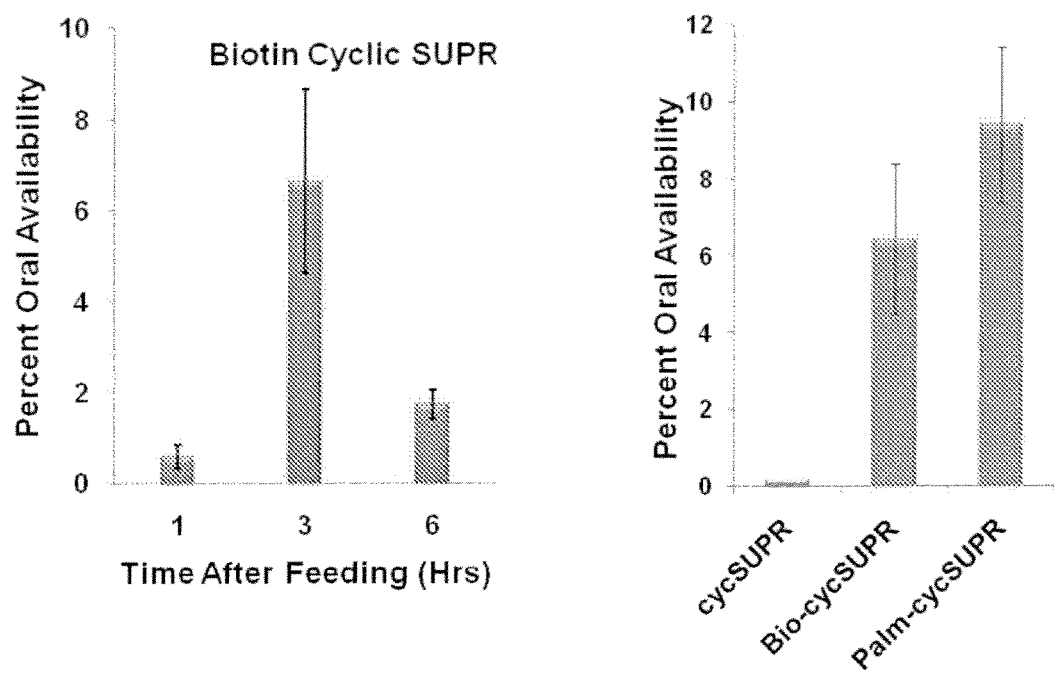
FIGS. 7A and 7B show that biotinylation and palmitoleic acid conjugation enhances oral bioavailability.

Crystal structures of serine proteases such as chymotrypsin and proteinase K show a hydrogen bonding network from the protease to the backbone of their substrate at four amino acid positions. Applicants postulated that N-methylation would result in a steric clash between the substrate and protease, thereby inhibiting the ability of the protease to bind to the peptide. In enzyme kinetic terms, this would result in an enhancement of Km. Additionally, several experiments have shown that proteases such as chymotrypsin, will not cut all of their predicted digest sites equally. It has long been observed that secondary structure will have an effect on proteolysis of a protein. However, there are now several independent examples of peptides with, with no predicted secondary structure that have predicted protease digest sites that are not proteolyzed. Applicants suspect that there may be some local sequence context that is inhibitor for proteolysis. This sequence context may either make it harder for the protease to bind its substrate (Km), or it may make it more difficult for the protease to perform catalysis on the substrate (Vmax). To investigate the origin of these enhancements, Applicants conducted a basic kinetic study with chymotrypsin. Proteinase K digested GIBP too quickly for this type of analysis but could be utilized in other systems and with other peptides. What Applicants found was that SUPR peptide optimized both Km (binding of enzyme to substrate), and Vmax (ability of the enzyme to process the substrate) were optimized for protease resistance relative to cycGIBP as may be observed in FIG. 5.

Next the role of each of the N-methyl alanines was analyzed independently. A traditional medicinal chemistry approach would suggest optimizing each position in a stepwise manner. For example sequence modifications, including N-methylation would be accomplished one amino acid at a time, walking the peptide from low protease stability to high stability. Whether this is a viable approach for making a peptide like SUPR was investigated. Towards that end, Applicants walked back from SUPR peptide to something closer to cycGIBP, and to determine if there was a gradual decrease in protease resistance. Towards that end, three peptides were synthesized. Two of them contained only one NMA (alanine was substituted for NMA), and the other had no NMA. It was hypothesized that if one could walk back to cycGIBP, then one would expect the loss of a single N-methyl to have some effect on reducing protease resistance, but to still be better than cycGIBP. One could also predict that the double mutant, SUPR peptide sequence containing no N-methylations would exhibit similar properties to cycGIBP. The effects were dramatic and surprising. Loss of a single NMA in both cyclic and linear sequences resulted in protease resistance significantly worse than that of the parent molecule GIBP. This was true for both chymotrypsin digestion and proteinase K digestion as detailed in Table 1. In fact, the proteolysis was so efficient for chymotrypsin that Applicants were not able to measure its half-life. This implies not only that there is a synergistic effect between the N-methylation but also that it would be extremely difficult to derive this peptide by traditional stepwise optimization.

Clinically, the overexpression of Her-2 in breast cancer correlates to a more invasive disease with increased tumor growth, chemotherapy resistance, and significantly lower long term survival for patients. Sausville, E. A and Burger, A. M. (2006) Cancer Research, 66:3351. Every year ~50,000 women are diagnosed with this form of breast cancer. Monoclonal antibodies to the ectodomain of Her-2 have been shown to be clinically effective in limiting the growth of tumors in vivo. Herceptin was one of the first examples of a FDA approved monoclonal antibody for the treatment of cancer. However, as is typical with antibody therapeutics, treatment is very expensive. Herceptin is typically dosed at 2 to 8 mg/kg costing patients up to $100,000 per year (Szabo, L. (2006) USA Today, available at the web address: www.usatoday.com/news/health/2006).

As with all antibody therapeutics, they are expensive to develop, control quality, produce, store, dose, not orally available, and their size limits their efficacy with solid

TABLE 1

TABLE 1: Synergistic effect of N-methyl alanine. Loss of a single N-methyl alanine results in peptide stability that is equal to, or lower than the stability of GIBP.

| Sequence | Chymotrypsin | | Proteinase K | |
|---|---|---|---|---|
| | Lin $t_{1/2}$ | Cyc $t_{1/2}$ | Lin $t_{1/2}$ | Cyc $t_{1/2}$ |
| MITWYEFVAGTK (SEQ ID NO: 19) | 0.33 min | 2.1 min | <0.2 min | 1.0 min |
| MFYAYEYAQWSK (SEQ ID NO: 7) | 21 min | 394 min | 2800 min | 5300 min |
| MFYAYEYAQWSK (SEQ ID NO: 20) | <0.2 min | <0.2 min | <0.2 min | 0.71 min |
| MFYAYEYAQWSK (SEQ ID NO: 21) | <0.2 min | <0.2 min | <0.2 min | 0.77 min |
| MFYAYEYAQWSK (SEQ ID NO: 22) | <0.2 min | <0.2 min | <0.2 min | <0.2 min |

Experiment No. 2

This experiment shows application of the method of Experiment No. 1 to synthesize peptides with pre-determined functionality. In addition, N-methyl norvaline was utilized and the starting peptide was selected from an antibody loop region.

Every year 50,000 women are diagnosed with the highly lethal Her-2 (+) breast cancer. Herceptin (Trastuzumab) is the only FDA-approved biological therapy but costs $100,000 per year. This creates a financial barrier to health care or a tremendous burden for those who choose to pay for treatment. Furthermore, treatment is painful, inconvenient, and presents an infection risk since it must be administered through large IV injections. Herceptin sales generate ~$5 billion annually for Roche, validating the size and importance of this market.

Her-2 (Human epithelial growth factor 2) is a receptor tyrosine kinase found to be overexpressed in 20-30% of breast cancer patients. Lin, N. et al. (2007) Clinical Cancer Research, 13:1648. Her-2 is a unique receptor, having no known ligand, and functions by homo- and heterodimerization with other Her (1,3 and 4) family members. Dimerization promotes the stimulation of cellular proliferation, invasion, and anti-apoptosis (Lin et al. (2007), supra.)

tumors (Cho, M. J. and Juliano, R. (1996) Trends in Biotechnology, 14:153). Stabilized peptide therapeutics could greatly benefit patients with this disease by increasing accessibility to treatment by dramatically reducing cost and providing a potentially oral route to administration.

THG73 tRNA Preparation.

The method described in Example 1 was followed.

N-methyl Norvaline-tRNA.

Figure 10:
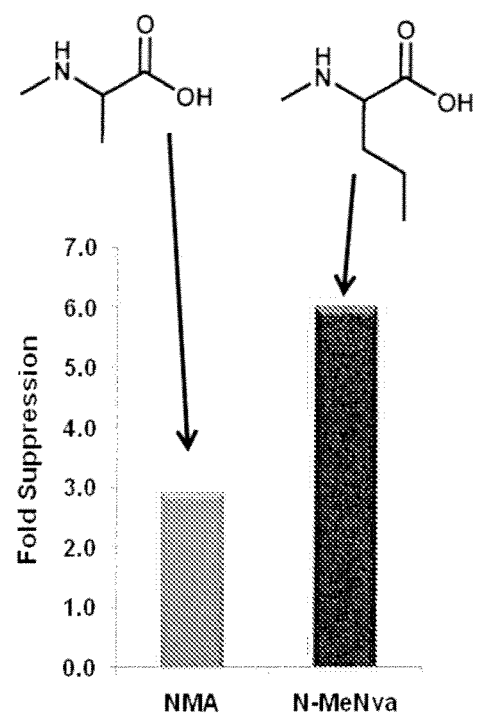
FIG. 10 shows enhanced translation efficiency of N-methyl norvaline. N-methyl norvaline (N-MeNva) translates approximately twice as efficiently as N-methyl alanine (NMA) in the context of a MFFXFF (SEQ ID NO: 73), template where X is the N-methyl amino acid. The sidechain of N-methyl norvaline is also an isostere for methionine, which is a prevalent amino acid found in protein-protein binding domains.
Figures 11A, 11B:
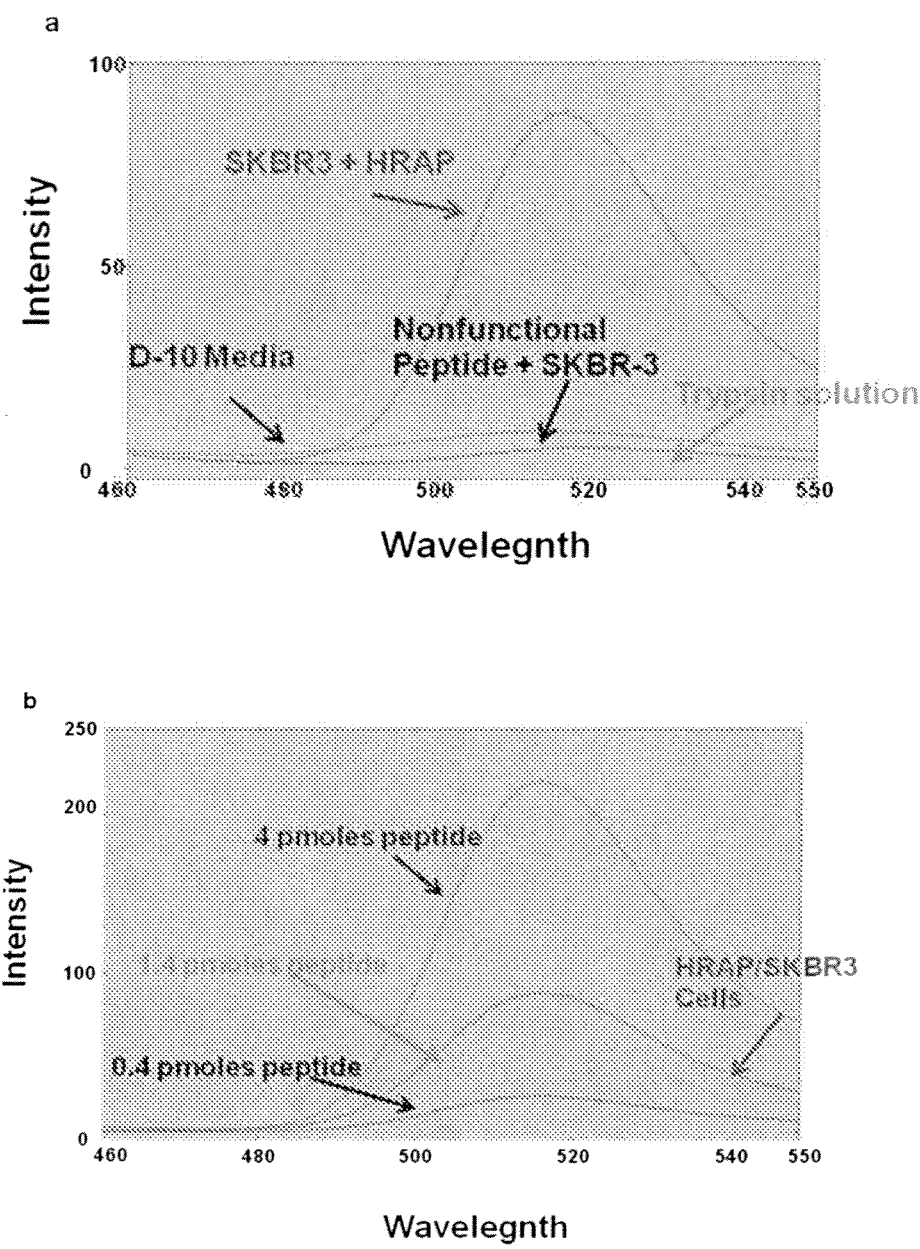
FIGS. 11A and 11B show quantitation of Her-2 expressed on SKBR-3 cells.

Norvaline is an amino acid with a straight 3 carbon side chain, and reasonably isosteric for methionine. N-methyl norvaline translates more efficiently than N-methyl alanine. When translating the sequence MFXFF (SEQ ID NO: 23), where X is the n-methyl amino acid, N-methyl norvaline shows twice the suppression efficiency (the ratio of translation efficiency with tRNA-N-methyl amino acid to translation efficiency without tRNA-N-methyl amino acid), as can be seen in FIG. 10. The synthesis of N-methyl, N-nitroveratrylcarbonyl norvaline cyanomethyl ester was carried out according to methods known in the art and published protocol. The final product was purified by silica gel chromatography in 3:1 EtOAc/hexanes. Yield 187.5 mg (24%). The synthesis of N-methyl, N-nitroveratrylcarbonyl alanine-dCA was carried out according to previous protocol. Yield 0.5 mg (2.5%). Following ligation to THG-73 tRNA, deprotection of the nitroveratryloxycarbonyl group was effected by photolysis with a xenon lamp equipped with a 315-nm cutoff filter, and the N-methyl norvaline tRNA was immediately added to the translation reaction.

Synthesis of N-Methyl Scanning Library.

Two single-stranded DNA templates were ordered from Integrated DNA Technologies. The sequences were 5'-GGG ACA ATT ACT ATT TAC AAT TAC AAT GNN SKR SKA KKR KTW STA KKM SNN SAA AAG TAG TGG TAG CAG CGA TTA CA-3' (SEQ ID NO: 24) and 5'-GGG ACA AAT ACT ATT TAC AAT TAC AAT GNN SYM KYA KKM KYA STW KNN SAA AAG TAG TGG TAG CAG CGA TTA CA-3'(SEQ ID NO: 25) using machine mixing for variable positions (W=A or T, K=G or T, M=A or C, R=G or A, S=G or C, Y=T or C). The double stranded library was produced and amplified by performing 6 cycles of PCR on 1 pmole of PAGE gel purified single-stranded library. PCR was performed under standard conditions utilizing the primers Gen-FP (5'-TAA TAC GAC TCA CTA TAG GGA CAA TTA CTA TTT ACA ATT ACA-3' (SEQ ID NO: 11)) and the reverse primer (5'-TGT AAT CGC TGC TAC CAC TAC TTT T-3' (SEQ ID NO: 26))

The Round 0 mRNA pool was generated by T7 runoff transcription and purified by urea-PAGE. The purified mRNA was ligated to F30P (5=–dA21[C9]3dAdCdC-P (SEQ ID NO: 74); C9 tri-(ethylene glycol) phosphate (Glen Research), P puromycin (Glen Research)), via an oligonucleotide splint (5'-TTT TTT TTT TTT TTG TAA TCG CTG C-3' (SEQ ID NO: 27)). Ligation was urea-PAGE purified and quantified via absorbance at 260.

Translation and Cyclization.

The method described in Example 1 was followed.

Selection.

Obtaining target protein for this selection step was a technical challenge. Her-2 is a multidomain protein, and the peptides had to target the ectodomain and not the intracellular kinase domain. Additionally, Her-2 is heavily post-translationally modified. Expressing and purifying functional Her-2 with the correct post-translational modifications would be difficult. However, several immortalized cell lines have been derived from breast cancer patients with Her-2 heavily overexpressed and since they are human cell lines, should have all the post-translational modifications present in a Her-2 positive cancer patient. Following ethanol precipitation of the round 0 DSG treated fusions, the pellet was dissolved in 100 µL of dH$_2$O and reverse transcribed with Superscript II under standard conditions. Following reverse transcription, the library was diluted 2 fold into 50 mM potassium phosphate buffer (pH=8.0). Proteolysis became more stringent as the selection continued. All proteolysis used immobilized proteases purchased from Sigma. Round 0 fusions were subject to 0.1 mgs of proteinase K for 30 sec. Round 1 was proteolyzed with 1 mg of proteinase K for 30 sec. Rounds 2 and 3 fusions were proteolyzed with 1 mg of proteinase K for 5 min. Finally, round 4 fusions were proteolyzed with 1 mg of proteinase K, 1 mg of chymotrypsin, and 1 mg of trypsin for 5 min. All proteolysis was performed at room temperature. Proteases were removed by spin filtration.

Two days prior to selection 150,000 SKBR-3 cells per well were seeded into 2 wells of a 96 well plate and grown under standard cell culture conditions (D-10 media, 5% CO$_2$, 37° C.). SKBR-3 cells were incubated with proteolyzed fusions that had been diluted to 400 µL in D-10 media (200 µL used per well). After 1 hr at room temp fusions were removed and cells were washed 4 times with D-10 media. After washings, cells were proteolyzed for 20 min at room temp. using proteinase K (0.5 mgs/well). Fusions were removed from cells and protease by spin-x filtration. The Her-2 libraries were regenerated by a 400 µL PCR using the "Phusion Blood Direct PCR Kit" (New England Biolabs), following manufactures instructions. PCR amplification of the eluted library members was carried until band was observed on a 4% agarose gel (15-20 cycles).

The round 5 pool was amplified by PCR using taq polymerase and subcloned into the TOPO-TA vector (Invitrogen) followed by transformation into TOP10 competent cells (Invitrogen). Individual clones were sequenced (Laragen).

Cell Culture.

SKBR-3 cells were purchased from the ATCC. DMEM and FBS were purchased from GIBCO. Cells were cultured under standard conditions using D-10 media.

Cell Proliferation.

Proliferation was measured by standard BrdU cell proliferation assay (Calbiochem). Cell lines were plated in 96-well plates (20,000 cells/well) in D-10 media with indicated amount of peptide with 2% DMSO, and incubated overnight. The BrdU compound was given to the cells for 2 hrs. Following the manufacturer's protocol, samples were analyzed by UV absorbance measurements at 450 nm. Peptide signal was normalized to cells incubated with 2% DMSO but no peptide. IC50 data was generated by fitting the data to a drug response equation (Log(drug) vs. Response, GraphPad Prism 5.0).

In Vivo Studies.

NCr homozygous athymic (nude) mice (six to eight weeks-old) were purchased from the National Cancer Institute. An aliquot of 2×10$^6$ SKBR-3 cells were suspended in 200 ml of PBS and injected subdermally in the right thigh of each animal. Treatment began 7 days after inoculation. Peptide 1 and Peptide D were coadministered at a total peptide concentration of 7 mg/kg three times a week by IV injection. Tumor growth was monitored weekly for four weeks. Tumor volume measurements were my following standard protocols using an electronic caliper.

Peptide Synthesis.

All solvents were purchased from Sigma. All other peptides were synthesized using fmoc-Gly-Wang resin (250 mgs, 0.15 mmoles) unless otherwise specified. Standard couplings were carried out with 5 eq. of monomer on a PS-3 automated peptide synthesizer (Protein Technologies). Fmoc deprotection was carried out with 20% methyl piperidine at room temperature for 10 min. After the addition of the N-terminal amino acid, peptides were capped with glutaric anhydride. Following N-terminal capping, lysine(mmt) was selectively deprotected with 3% DCM, 1.5% TIS, and 1.5% EDT in DCM for 1 hr at RT. After washing resin with NMP, cyclization on resin was accomplished by the addition of HATU (5 eq) and DIEA (10 eq) and rotating for 1 hr at RT. Following cyclization, deprotection, cleavage with 95% TFA, filtration and ether extraction, the crude product was purified on a Vydac C-18 reverse phase column using gradient elution (0% B for 5 min, 10-50% B in 40 min. Solvent A: H$_2$O with 0.1% TFA, Solvent B: CH$_3$CN with 0.035% TFA. Lyophilized solid was reconstituted in DMSO and quantitated by absorbance at 280 nm ($\epsilon$280=9970 L mol-1 cm-1). Yield=10-25%.

Human Serum Digests.

Delipidated/lyophilized human serum was purchased from Thermo Scientific and reconstituted as per manufacturer's instructions. 250 nmoles of peptide in 50 µL of sodium phosphate buffer (pH=8.0) with 10% DMSO was added to 1 mL of reconstituted serum and incubated at 37° C. 100 µL aliquots were taken at various time points and quenched in 300 μL of acetonitrile. Samples were spun down and decanted to remove precipitate followed by dilution in water to 1.5 mLs. Samples were injected onto a C-18 reverse phase column and separated by gradient elution (15-90% B in 25 min. Solvent A: 0.1% TFA in water. Solvent B: $CH_3CN$ (0.05% TFA). The area under the starting material peak was quantitated using the 32 Karat Gold Software package (Beckman). The plotted values represent the mean of two experimental values, and the error bars represent the standard error of the mean. The graph was generated by fitting the data to a one phase exponential decay equation (Graph-Pad Prism 5.0).

Discussion

Figure 8:
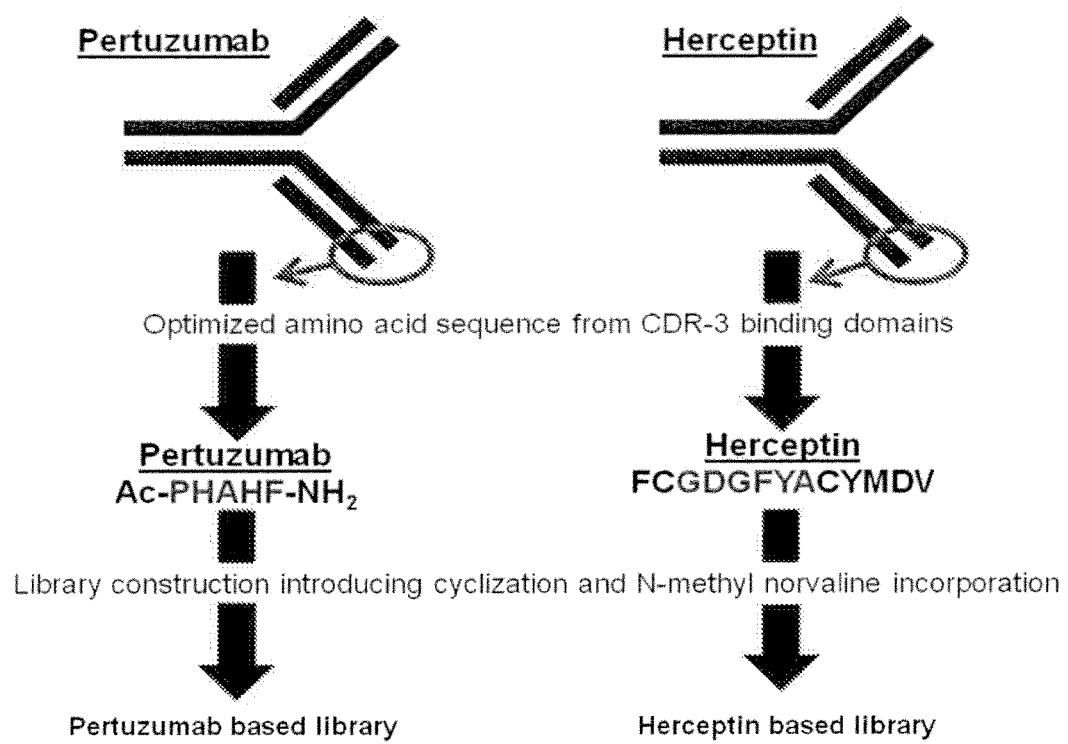
FIG. 8 illustrates the design of the Her-2 N-methyl scanning library. Previous work (Park, B., et al. (2000) Nat Biotech 18:194, Nakajima, H., et al. (2008) Breast Cancer 15:65) identified and optimized the residues of the monoclonal antibodies used in Her-2 binding. From that, libraries were constructed using the residues highlighted in gray scale. A flanking random amino acid was placed on either side of the sequence. Met to Lys cyclization was also incorporated. Millward, S. et al. (2007) ACS Chem. Biol., 2:625. Sequences disclosed as SEQ ID NOS 56-57, respectively in order of appearance.

Two peptides were derived from examining the antibody loops involved in target binding. ANHP is a peptide derived from the Herceptin loop, (Park, B.-W. et al. (2000) Nat Biotech, 18:194) and HRAP was derived from Omnitarg (Nakajima, H. et al. (2008) Breast Cancer 15:65). Both exhibit in vitro function at high micromolar concentrations. From these peptides, two separate cyclic peptide libraries were developed. A flanking randomized residue was placed on either side of the lead peptide sequence which is illustrated in FIG. 8.

The two resulting peptide libraries were of different lengths (MX8K for the Herceptin based library, and MX7K for the Omnitarg based library as depicted in FIG. 9) which allowed tracking to determine which peptides are derived from which original family of ligands to choose for coadministration. The two libraries were mixed after round 0 PCR in equal proportion and carried through the selection together, giving a total diversity of 21 million unique DNA sequences.

Applicants used fluorescein labeled HRAP peptide to quantitate Her-2 expression. Peptide was incubated with cells, and after washing the cells were trypsinized and analyzed on a fluorometer. Human cells highly expressing Her-2 will have 2 million or more copies on their surface. Applicants found that there were approximately 4.5 million copies of Her-2 expressed per cell. 200,000 cells would contain approximately 1.5 pmole of target, which is in the range necessary for targeting by mRNA display.

Figures 12A, 12B:
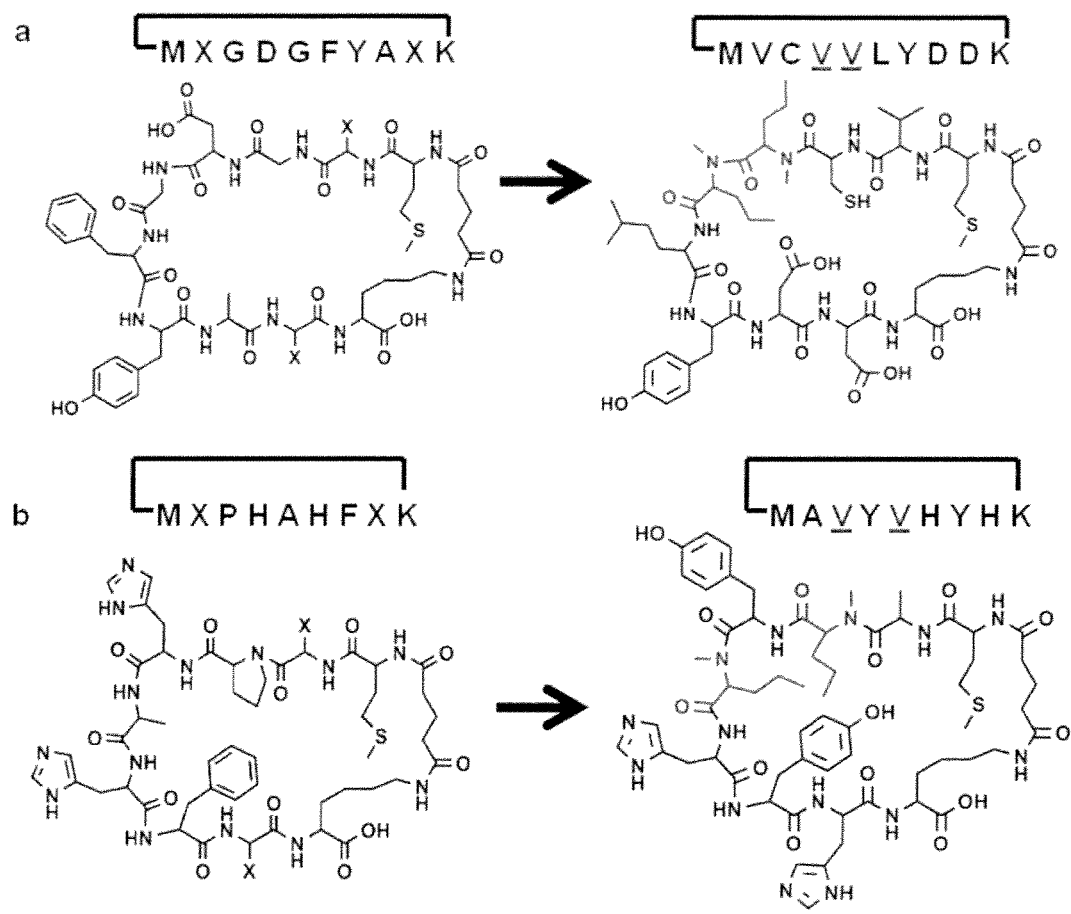
FIGS. 12A and 12B show evolution of peptides from their parental molecules.

Selection was conducted under similar conditions as described in Example 1. After 4 rounds of selection, pool 5 was sequenced and resulting sequences were separated into their original families. 5 members from the Omnitarg (named 1 through 5, 1-MAVYVHYHK (SEQ ID NO: 28), 2-MSYHYVVPK (SEQ ID NO: 29), 3-MLSYSHVQK (SEQ ID NO: 30), 4-MEYVSYVAK (SEQ ID NO: 31), 5-MRHQEVLLK (SEQ ID NO: 32) where V is N-methyl norvaline), family and 5 members from the Herceptin family (named A through E, A-MQYDEYVDSK (SEQ ID NO: 33), B-MLWDEYVACK (SEQ ID NO: 34), C-MMW VEFYSLK (SEQ ID NO: 35), D-MVCVVLYDDK (SEQ ID NO: 36), E-MVCEYYVYSK (SEQ ID NO: 37) where V is N-methyl norvaline) were chosen for initial screening. Cyclized fusions were tested for binding before and after proteolysis. The top binding peptide in each family was also the most protease resistant. These peptides, peptides 1 and D, were chosen for further characterization. Comparing the N-methylated molecules with the parental molecules showed significant changes. In peptide D, 5 of the 6 original residues had changed. One of the mutations was conservative, however the others would have been difficult to predict by rational design. In peptide 1 of the 5 positions changed, however the changes showed some conservation of the original functionality. For example, PHE changed to TYR and PRO changed to N-methyl norvaline. In examining the structures it is evident that there are significant chemical similarities between these peptides. However, both in the case of peptide 1 and D, the overall peptide structure is significantly different from the parental sequence. This data, suggests that their development by traditional medicinal chemistry would be extremely difficult. A schematic showing the structural changes can be seen in FIG. 12.

The peptides were then screened for function using a standard in vitro assays used to test efficacy of Her-2 targeting molecules. The assay involved analyzing a molecule's ability to inhibit proliferation in cell culture. A widely used kit is the BrdU cell proliferation assay. In this assay, cells are incubated with the molecule of interest before having their media supplemented with a bromodeoxyuridine. Bromodeoxyuridine is incorporated into the DNA of proliferating cells. DNA with this modified base is recognized with an antibody, and quantitated by ELISA. Applicants tested the peptides and compared them with their parental molecules. There were dramatic improvements in efficacy for both peptides. HRAP had an $EC_{50}$ of 230 μM in comparison to peptide 1's $EC_{50}$ of 520 nM, a nearly 450 fold improvement. ANHP had an $EC_{50}$ of 67 μM[7] in comparison to peptide D's value of 640 nM, nearly a 110 fold enhancement (see Table 2).

Applicants then added the peptides in equal concentration to cell culture and performed the BrdU cell proliferation assay. Applicants found an enhancement resulting in an $EC_{50}$ corresponding to a total peptide concentration of 15 nM. This corresponds to a 40 fold enhancement over peptide 1 and a 35 fold enhancement over peptide D when administered individually (Table 1). This suggests that peptide 1 and peptide D are functioning cooperatively.

TABLE 2

Dramatic improvement in the inhibition of proliferation of Her-2 positive cells based on BrdU incorporation.

| Peptide | IC50 |
| --- | --- |
| HRAP | 230000 nM |
| Peptide 1 | 520 nM |
| AHNP | 67000 nM |
| Peptide D | 640 nM |
| Peptide D + 1 | 15 nM |

Peptide 1 and Peptide D show approximately a 440 and 100 fold improvement with respect to their parental molecules. Coadministration of Peptide 1 and Peptide D shows approximately a 35 and 43 fold improvement over individual administration respectively.

Figure 13:
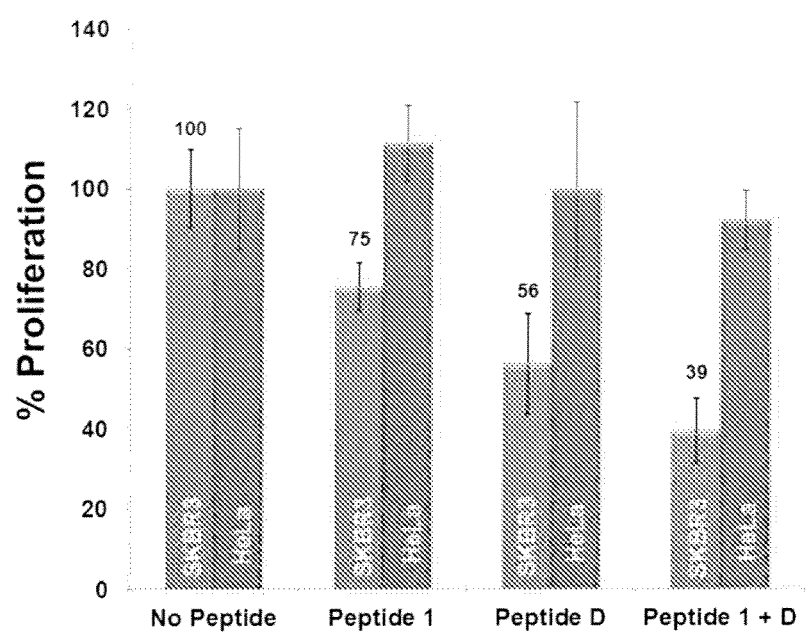
FIG. 13 shows the inhibition of cellular proliferation with peptide made by the disclosed methods. Shown is the maximal effect on proliferation of Her-2 positive cancer cells (SKBR-3 cells, in blue). Percent inhibition calculated by 100−(% proliferation). HeLa cells are used as a control because they are not a Her-2 overexpressing line.

Another measure of the effectiveness of these peptides is their maximal inhibition on cellular proliferation. That is, at concentrations significantly above the $EC_{50}$, how much slower is the proliferation of SKBR-3 cells. SKBR-3 cells treated with Herceptin proliferate at 75% the rate of untreated cells (25% inhibition). Peptide 1 and peptide D show inhibitions of 75% and 56% proliferation respectively (25% and 44% inhibition respectively) (see FIG. 13). HeLa cells were used as a control because they do not overexpress Her-2 and are not responsive to Her-2 targeting treatments. As expected, HeLa cells showed no inhibition in their ability to proliferate. If peptide 1 and peptide D function in a cooperative manner producing a multiplicative effect on inhibition Applicants would expect coadministration to exhibit an inhibition of 42% proliferation (58% inhibition). In fact the value was 39% proliferation (61% inhibition), within error of this prediction (see FIG. 13).

Figure 14:
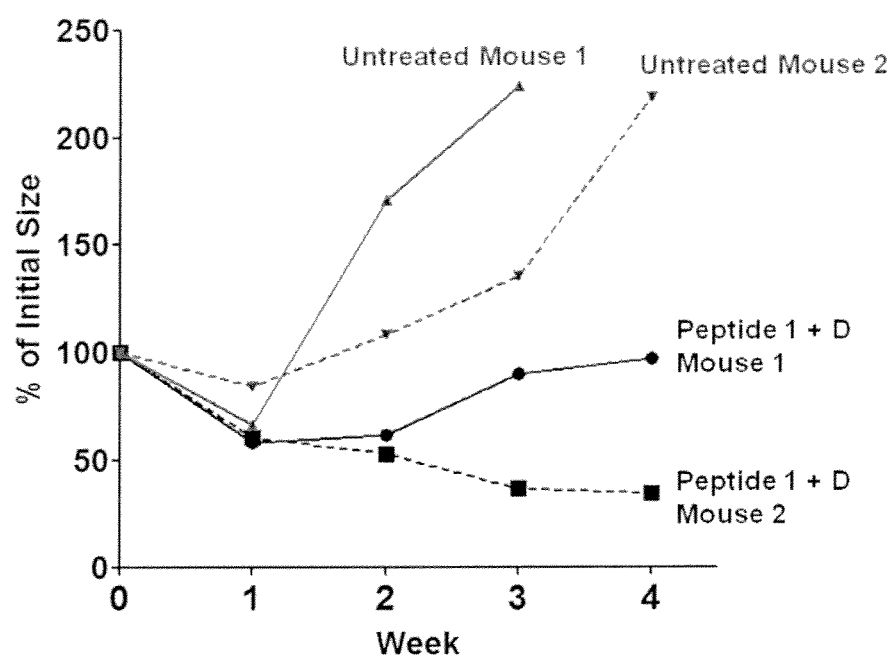
FIG. 14 shows selected peptides that show in vivo efficacy. Individual mouse curves are labeled. Mice were dosed at 7 mg/kg by intravenous administration 3 times weekly.
Figure 15:
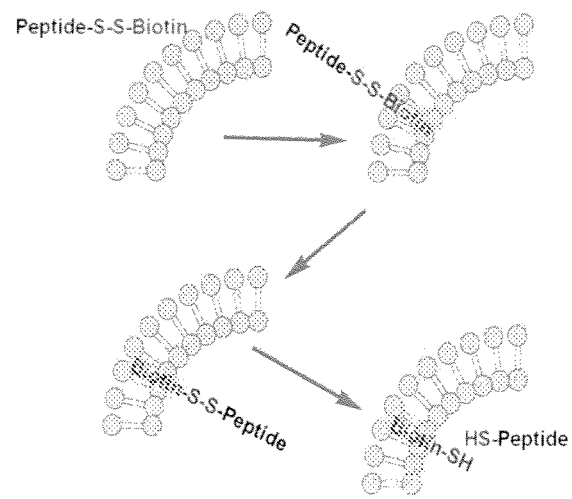
FIG. 15 is a proposed schematic displaying the mechanism of biotin mediated peptide shuttling.
Figure 16:
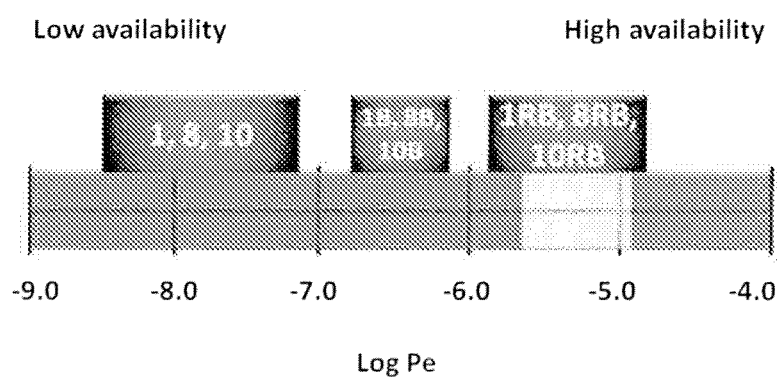
FIG. 16 shows the oral availability by PAMPA log Pe measurements. Stoop, A. A., et al. (2003) Nat Biotech 21:1063. Log Pe values associated with 50% availability or above in green, 5-75% in yellow, and below 5% in red. A notable exception is cyclosporine which has a log Pe of between −6.6 and −6.3 but is 25% bioavailable. Reducible biotin-labeled peptides denoted by RB following their number.

Finally Applicants wanted to determine if selected peptides could illustrate in vivo function. Literature shows that xenografts treated with Herceptin were characterized by a slower tumor growth in comparison to mice without treatment. Nude mice were inoculated with SKBR-3 cells. Mice were treated 3 times weekly for 4 weeks with intravenous injections of peptide 1 and peptide D with a total peptide concentration of 7 mg/kg. Mice treated with peptide showed either a halt in the progression of tumor growth, or a decrease in tumor volume. This result exceeds published results for Herceptin in this model system. See FIG. 14.

Even with advances in biotechnology, many proteins are difficult to purify in their functional state. By successfully targeting protein expressed on a human cancer cell, Applicants have derived a new path to obtaining targets for mRNA display. This also includes the creation of ligands to many proteins that were too technically difficult to target in the past. There are also implications to personalized medicine. The targeted cells in this selection, SKBR-3 cells, came from a breast cancer patient. An obvious extension of this technology would be to develop it to the point where a biopsy may be taken from a cancer patient, and those cells used as a target in this type of mRNA display to derive a truly personalized treatment.

With the targeting of Her-2, Applicants have shown that through the combination of cyclization and N-methyl amino acid incorporation into mRNA display Applicants are able to derive bioavailable peptide ligands. These ligands show in vivo stability sufficient for drug like function. These enhancements translated to peptides that could show high levels of in vivo efficacy. Additionally, the process of lead development was fast. Target selection to lead characterization was 3 months. In vivo efficacy was shown in a total of 5 months. This data validates this mRNA display method as a rapid platform technology able to efficiently develop highly stable, efficacious peptidic ligands for the purpose of peptidomimetic development in disease treatment. These Her-2 inhibiting peptides are merely the first of many in a new class of peptidomimetics able to be developed as highly effective treatments for disease.

Experiment No. 3

This example illustrates modification of the peptides for oral bioavailability.

Cellular Uptake Assay.

Fluorescein labeled peptide added to approximately $1.5 \times 10^5$ HeLa cells in 200 μLs of DMEM growth media with 5% FBS such that the final peptide concentration is 10 μM. Cells were incubated overnight at 37° C. with 5% $CO_2$. Cells were washed 4 times with PBS, trypsonized, and buffer exchanged to PBS. The cells were analyzed by using fluorescent flow cytometry and dead cells were excluded from the analysis. The data presented are the mean fluorescent signal for the 5,000 cells collected.

Confocal Microscopy.

Approximately $1.5 \times 10^5$ HeLa cells were plated on a 96 well plate. Cells were incubated with 10 μM fluorescein labeled peptide in DMEM media with 5% FBS and 2% DMSO overnight. The cells were washed with PBS and observed with an inverted microscope using a 60x objective. 490 nm light was used to excite fluorescein and a 520 emission filter was used for observation of the green emission. When comparing the uptake or activity of the peptides the imaging conditions (such as photomultiplier gain/offset, laser intensities and confocal aperture size) were kept constant for the observation of the different conjugates, so that the intensities represent the true differences in uptake/activity.

Oral Bioavailability.

The following peptides were synthesized for oral administration: MFYVYEYVQWSKK(FAM) (SEQ ID NO: 14), MITWYEFVAGTKK(FAM) (SEQ ID NO: 16), MFYVY-EYVQWSKK(FAM)DK(biotin) (SEQ ID NO: 38), and MFYVYEYVQWSKK(FAM)DK(Palmitoleic acid) (SEQ ID NO: 15). All peptides were cyclized from the side chain to lysine to the N-terminus as previously described in Millward, S. W. et al. (2007) ACS Chem. Biol. 2:625. Anesthetized C57BL6 mice had peptide administered at a dose of 10 mgs/Kg by oral gavage. After administration, mice were removed from isoflurane. At various time points, blood samples were taken by orbital bleeding as previously described. Peaks were normalized to a 20 minute time point from mice that had peptide administered by IV injection. Area under the curve was analyzed by Graphpad 5.0.

Peptide Synthesis.

All solvents were purchased from Sigma. Peptides were synthesized by manual solid-phase peptide synthesis using rink amide am resin, following standard protocols. Standard couplings were carried out with monomer (5 equiv; Novabiochem) in HATU (2 mL, 0.6 mmol; Novabiochem), HOAt (1.2 mmol; Genescript) in DMF with DIEA (1.8 mmol) at room temperature for 20 min. Coupling to an N-methyl amino acid followed the same procedure with a 30 min coupling time. Fmoc deprotection was carried out with 20% piperidine (Anaspec) at room temperature for 20 min. Following, deprotection, cleavage with 95% TFA, filtration and ether extraction, the crude product was purified on a Vydac C-18 reversed-phase column using gradient elution (0% B for 5 min, 10-50% B in 40 min. Solvent A: H2O with 0.1% TFA, Solvent B: $CH_3CN$ with 0.035% TFA). Lyophilized solid was reconstituted in DMSO and quantitated by absorbance at 280 nm. Yield=10-25%.

N terminal specific biotinyation with reducible biotin was accomplished by reacting peptides with NHS-biotin (Pierce) following manufacturer's protocols. Cyclosporine was purchased from Sigma Aldrich. DNA was purchased from IDT DNA.

PAMPA.

PAMPA assays were set up following manufacturer's instructions. Briefly, 1% phosphatidyl choline (Sigma) was dissolved in dodecane (Sigma) at 65° C. for 3 min. The membrane was applied to each well as per manufacturer's instructions. Peptides 1-10 and 1-10B (see Table 3, 15 μL of 4 mM peptide in DMSO) were diluted to 300 μL in PBS pH 7.4. 100 μL of sample was put into each donor well. The acceptor wells contained 300 μL of a 5% DMSO in PBS solution. Passive diffusion was allowed to occur at room temperature for 24 hrs. At this time, samples were run on a HPLC Vydac C-18 reversed-phase column using gradient elution (0% B for 5 min, 10-50% B in 40 min. Solvent A: H2O with 0.1% TFA, Solvent B: $CH_3CN$ with 0.035% TFA). Absorbance at 215 nm was monitored. The area under the peptide peak was integrated. Due to cyclosporine A's low absorbance reading, multiple wells acceptor solutions had to be combined.

Peptides 1RB, 8RB, and 10RB (sequences are provided in Table 3) followed the changes. The acceptor well contained 10 mM DTT as a reducing agent. Data was collected after 6, 12 and 24 hrs. Absorbance at 280 nm was analyzed. The following formula was used to calculate Log Pe:

$$\log P_E = \log\left(C - \ln\left(1 - \frac{[\text{drug}]\text{acceptor}}{[\text{drug}]\text{equilibrium}}\right)\right)$$

-continued $$C = \left(\frac{Vd \times Va}{(Vd + Va)\text{Area} \times \text{time}}\right)$$

Membrane Localization.

Membrane was set up as described above. Donor and acceptor wells had peptides at 0.2 mM. Peptide concentration in the donor well was quantitated by absorbance at 280 nM at times 0 and 15 min. Care was taken not to disrupt the membrane when samples were removed.

Insulin Biotinylation and Characterization.

0.25 mmoles of human insulin was reconstituted in 1 mL 50 mM sodium phosphate buffer (pH=8.0). To this was added 0.5 mmoles of sulfo-NHS biotin (pierce). The reaction was allowed to proceed for 1 hr at room temp before HPLC purification on a on a Vydac C-18 reverse phase column using gradient elution (0% B for 5 min, 10-50% B in 40 min. Solvent A: $H_2O$ with 0.1% TFA, Solvent B: $CH_3CN$ with 0.035% TFA. Peaks were analyzed by MALDI-TOF. Two peaks corresponded with single biotinylations and were tested for efficacy in vivo. The second peak was determined to be more efficacious and used for further characterization. To determine the site of biotinylation, purified singly biotinylated insulin was digested with 0.1 mg of immobilized chymotrypsin agarose (sigma) for 1 min at room temp. Reaction was stopped by filtration. MALDI-TOF analysis was used to determine that biotinylation occurred on the N-terminus of the B-chain.

In Vivo Effect of Peptides In Vivo.

Experimental procedure followed previously published protocols with slight modification, see e.g., (McKern, N. M., et al. (2006) Nature 443:218; Schïffer, L., et al (2003) PNAS 100:4435). Briefly, C57BL6 mice (4 in each group) fasted overnight and were anesthetized using isoflurane prior to taking blood samples by orbital bleeding. Mice were dosed with insulin or biotinylated insulin at a concentration of 3.5 nmol/kg by IV injection into the tail vein. For oral bioavailability, insulin was dosed at 1.75 and 7 nmol/kg and administered by oral gavage. In all cases, insulin was in 150 µL of 50 mM sodium phosphate buffer (pH=8.0). Blood was analyzed on a standard Clarity Plus blood glucose meter (VWR). Readings were normalized to a T=0 blood sugar measurement, and analyzed on Graphpad 5.0.

A number of limited predictive models also exist that are more closely applicable to the development of peptide ligands. First analysis by Veber et al., (Veber, D. F. et al. (2002) Journal of Medicinal Chemistry 45:2615) indicates that oral availability correlates with having 10 or fewer rotatable bonds and argues that large cyclic molecules may be quite cell-permeable. Second, experimental work by Lokey and coworkers indicates that cyclizing peptides can dramatically improve their passive membrane permeability by 10- to 100-fold, generating molecules with similar membrane crossing ability as cyclosporine. Rezai, T. et al. (2006) Am. Chem. Soc. 128:2510. However the generality of these results has yet to be determined, and there are a number of examples where cyclization does not seem to help permeability. Kwon, Y.-U. and Kodadek, T. (2007) Chemistry & Biology 14:671.

Work from both the Kuliopulos and Smrcka labs indicates that attaching a long chain fatty acid (palmitic C16, or myristic C14) enables peptide-fatty acid conjugates added to cells to gain access to the cytosol. (Veber, D. F. et al. (2002) Journal of Medicinal Chemistry 45:2615; Kwon, Y.-U.; Kodadek, T. (2007) Chemistry & Biology 14:671). The mechanism of this has not been studied in detail, but it appears the fatty acids incorporate into the outer leaflet, followed by transfer to the inner leaflet. Further studies showed that these compounds cross the blood brain barrier. (Zhuang, Z. P. et al. (2001) Journal of Medicinal Chemistry 44:1905). Finally, Meade and coworkers have shown that a stilbene derivative, (ADMS), could ferry a gadolinium chelate across cellular membranes for the purpose of serving as an intracellular contrast agent. Baumann, K. et al. (1994) Protein Sci 3:750). In all cases, the transfer mechanism seems to be passive and implies that attaching hydrophobic or amphiphilic molecules to peptides provide a facile route for them to cross cellular membranes. It also seems likely that the more hydrophobic moieties (palmitic and myristic acid) keep their attached peptides associated with the membrane, similar to proteins modified in this fashion (Wadia, J. S. et al. (2004) Nat Med. 10:310) resulting in lower efficiencies of passive transfer across membranes.

There are only a few other oral insulin formulation in clinical trials. Most of these formulations focus on encapsulation of insulin to allow its transport through the stomach and release in the intestines. These technologies are difficult to perfect, require higher dosing of insulin, and require higher dosing in preclinical studies with suggests that they will be significantly more costly than Applicants product. Furtado, S., et al. (2008) International Journal of Pharmaceutics 347:149; Sonaje, K., et al. (2009) Biomaterials 30:2329; Yin, L., et al. (2009) Biomaterials 30:5691. Additionally, since none are yet FDA approved, Applicants have yet to see if this new technology will be free of toxicity issues.

A GLP-1 analog appended to a fatty acid is also being developed by Novo Nordisk for oral delivery. GLP-1 simulates the release of insulin in the pancreas of those with elevated blood sugar. Therefore this treatment will only be ineffective for type I diabetics who can still secret insulin or who are not extremely sensitive to insulin (advanced type II patients). Additionally, the use of fatty acids for oral uptake has been associated with irritation of the intestines. Iyer, H., et al. (2010) Obesity and Metabolism 12:179 and Runge, S. (2008) 283:11340.

The biotinylated insulin of this disclosure has significant advantages over all existing technologies. It is useful for both type I and type II diabetics, simple to synthesize, and cheap to manufacture. Since biotin is a vitamin (vitamin B7), and has undetectable toxicity, Applicants compounds should be free of toxicity issues. Additionally, Applicants data shows that biotin is more efficient at delivering cargo across a lipid bilayer as is necessary to target intracellular drug targets.

Applicants employed a parallel artificial membrane permeability assay (PAMPA) that will allow for the rapid screening of peptide passive diffusion across a phospholipid bilayer. (Schmidt, et al. (2003) J. Millipore Corporation Application Note AN1729EN00.). In this assay, two chambers are separated by a phospholipid bilayer supported on an inert membrane. Applicants chose to initially focus Applicants examination on peptide ligands developed to bind with high affinity to the heterotrimeric G-proteins G$\alpha$i1*GDP and G$\alpha$12*GDP. Jo, W. W., et al. (2004) Biochemistry 43:9265; Millward, S. W., et al. (2007) ACS Chem. Biol. 2:625; Fiacco, S. et al. (2008) Chem Bio Chem 9:2200. These ligands included variations in sequence, size, overall charge, and polarity as well as comparing linear and cyclic peptides, end and biotinylation. Many of the unmodified peptides were poor at crossing the phospholipid bilayer (Table 2). Two notable exceptions were peptide 1 and 3, which exhibited permeability similar to that of cyclosporine. According to classical methods of increasing permeability. Pinski, C. A., et al. (2001) Advanced Drug Delivery Reviews 46:3. Applicants postulated that the removal of hydrogen bond donors by N-methylation should further increase the permeability of this peptide. Peptides 2 and 9 experienced a significant increase in permeability. This may be due to the removal of a positive charge at their terminus. This data suggests that modification at the termini of a peptide may be generally beneficial.

Recently there has been some controversy as to the effect of cyclization on membrane permeability. Cyclic peptides are thought to benefit by an enhanced ability to shield their amide protons from the hydrophobic region of a bilayer by more easily forming intramolecular hydrogen bonds. Rezai, T., et al. (2006) Am. Chem. Soc. 128:2510. However peptide cyclization has not always led to enhanced membrane permeability. Kwon, Y.-U. and Kodadek, T. (2007) Chemistry & Biology 14:671. In the experiment, compound 7 was cyclized from the N-terminus to the side chain of Lys. This cyclization route also removes two positive charges, which would be predicted to further benefit permeability. In these findings, cyclization did not enhance passive diffusion, and was in fact slightly detrimental to the process.

Previous work has demonstrated that tethering peptide to fatty acids, or stilbene derivatives will allow peptides to access the cystolic side of a cellular membrane. Covic, L., et al. (2002) Nat Med. 8:1161; Endres, P. J., et al. (2006) Molecular Imaging 4:485; and Goubaeva, F., et al. J. Biol. Chem. 278:19634. The mechanism has not been studied in detail, but the modification is thought to function by localizing the peptide to the outer portion of the bilayer, followed by a transfer to the inner surface of the membrane. Applicants' aim was to find a nontoxic molecule that could be conjugated to a peptide that would be hydrophobic enough to enhance the localization of Applicants peptide to the phospholipid bilayer, without being so hydrophobic that it would not dissociate from the membrane. To that end, Applicants conjugated peptides to biotin, and examined their permeability. A dramatic increase of up to 2 orders of magnitude in the Log Pe of peptides N- or C-terminally labeled with biotin was observed. This provided five peptides with Log Pe values similar to cyclosporine. It may also be noted, that this conjugation seemed to act as a general enhancer for peptide delivery. Enhancements occurred in spite of peptide sequence variation, overall charge, backbone modification, or length. Biotinylation of the side chain of Lys of peptide 9 did not enhance membrane permeability, suggesting that the enhanced permeability was not simply a result of increased hydrophobicity or removal of a charge from the peptide. Taken in combination with the N-methyl data, this suggests that N- or C-terminal positions may be optimal for modification.

TABLE 3

| | Peptide Sequence | Log Pe of peptide | Log Pe of peptide (biotinylated) |
|---|---|---|---|
| 1 | DKLYWWEFL* (SEQ ID NO: 39) | -7.1 +/- 0.2 | -6.4 +/- 0.2 |
| 2 | Ac(N-MeD)KLYWWEFL* (SEQ ID NO: 40) | -6.1 +/- 0.1 | ND |
| 3 | NNNNNDKLYWWEFL* (SEQ ID NO: 41) | -6.6 +/- 0.2 | ND |
| 4 | NNNNNDK(N-MeL)YWWEFL* (SEQ ID NO: 42) | >-9.0 | ND |
| 5 | NNNNNDKL(N-MeY)WWEFL* (SEQ ID NO: 43) | >-9.0 >-9.0 | -7.4 +/- 0.1 -6.6 +/- 0.1 |
| 6 | NNNNNDKLY(N-MeW)WEFL* (SEQ ID NO: 44) | | |
| 7 | MITWYEFVAGTK† (SEQ ID NO: 45) | -7.8 +/- 0.1 | -6.6 +/- 0.1 |
| 8 | Cyclo-MITWYEFVAGTK† (SEQ ID NO: 46) | -8.2 +/- 0.2 | -6.5 +/- 0.0 |
| 9 | (N-MeNva)ITWYEFVAGTK‡ (SEQ ID NO: 47) | -7.0 +/- 0.1 | -7.4 +/- 0.1 |
| 10 | MSQTKRLDDQLYWWEYL* (SEQ ID NO: 48) | -8.4 +/- 0.1 | -6.2 +/- 0.0 |
| 11 | MRLVWIVRSRHFGPRLRMAK† (SEQ ID NO: 49) | ND | -6.0 +/- 0.1 |
| | Cyclosporin | -6.2 +/- 0.2 | NA |
| | DNA | >-9.0 | >-9.0 |

Membrane permeability is enhance by biotin conjugation. Values calculated using PAMPA as outlined in Morris, M. C. et al. (2001) Nat. Biotech, 19:1173.
Biotin-labeled peptides are designated by a B following their number. Peptides 7, 8, 9, and 11 are amidated.
*N-terminally biotin-labeled.
†C-terminally biotin-labeled.
‡biotin-labeled on the side chain of Lys.

In order to study the mechanism of this enhanced permeation in more detail, Applicants quantitated the biotinpeptide conjugate's membrane localization. Peptides 1B, 6B, 7B, 8B and 10B exhibited membrane localization of 8.4 to 14% respectively. Their nonbiotinylated counterparts, peptides 1, 6, 7, 8, and 10, localized 0 to 4.2% respectively. This suggests that the enhancement of membrane localization facilitated peptide delivery.

There seemed to be a maximum permeability coefficient of about −6.0, irrespective of the peptides initial permeability. Applicants' hypothesis was that a slow step in this process was now the dislocation from the inner membrane to the acceptor well. Additionally, Applicants' permeation process was reversible. A biotin-labeled peptide could localize to the membrane from the acceptor well, flip, and release into the donor well. Applicants addressed this by creating a biotin conjugate with a disulfide that would be labile intracellularly, but not extracellularly. This would expedite dislocation from the inner membrane, and create an irreversible delivery mechanism, trapping the peptide inside the acceptor well.

In pursuit of this aim, Applicants conjugated peptides 1, 8 and 10 to biotin containing a reducible disulfide. The PAMPA assay was set up so that conditions in the donor well were oxidizing, and the acceptor were reducing. Log Pe significantly increased in all three cases. In comparison to their nonlabile reducible counterparts peptide 1B exhibited an increase in Log Pe from −6.4 to −4.9, peptide 8 increased from −6.5 to −5.9, and peptide 10 increased from −6.2 to −4.8. This is a 16-fold increase in peptide delivery for peptide 10. Applicants also sought to determine if replacing biotin with a more hydrophobic molecule would further enhance delivery. Initial attempts employed cholesterol;

however peptide-cholesterol conjugates would aggregate under conditions required for PAMPA. Lauric acid, a 12 carbon saturated fatty acid, was also employed and exhibited enhanced membrane association as compared to biotin (27% vs. 14%). However these conjugates were not able to deliver peptide cargo as efficiently, resulting in a Log Pe of −6.8 in comparison to biotin's log Pe of −4.8.

Next Applicants sought out to determine whether this was a viable method of delivering peptide cargo in cell culture. If this were possible, it would allow us to develop ligands to target intracellular proteins. Peptide 1 was labeled with a fluorescein at the N-terminus, and a reducible biotin at the C-terminus as depicted in FIG. 17. Uptake studies were performed by incubating peptide overnight in human cervical cancer cells (HeLa), and mouse fibroblasts (3T3). Confocal analysis shows efficient delivery of peptide into both cell lines for peptide containing the biotin modification as can be noted in FIG. 17. However, cells incubated with protein without biotinylation did not show fluorescence. It also may be noted that the peptide has gained access to the nucleus, suggesting that it may be cytoplasmic.

Figures 18A, 18B, 18C, 18D:
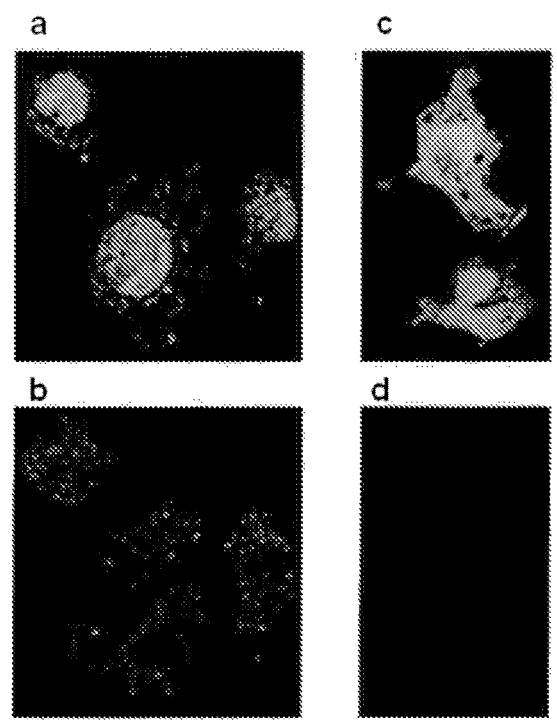
FIGS. 18A to 18D show that biotin shuttling not dependent on endocytosis. 3T3 cells are incubated with peptide 1 and examined by confocal using the fluorescein channel (FIG. 18A) or the rhotamine channel (FIG. 18B). 3T3 cells have been treated with the endocytotic inhibitor dynasore prior to peptide administration and are examined under the fluorescein channel (FIG. 18C) or the rhotamine channel (FIG. 18D).

Applicants wanted to determine whether active transport played a role in biotin mediated peptide uptake. 3T3 cells were incubated with a detran-rhotamine compound to label endocytotic vesicles. Significant colocalization was noticed between Applicants' peptide and the dextran rhotamine as can be noted in FIG. 18. The experiment was repeated in the presence of the dynamin dependent endocytotic inhibitor, dynasore. Uptake of Applicants' peptide still occurred, even in the absence of internalized dextran-rhotamine. Although active transport may be beneficial for internalization of biotin shuttling, it seems not to be necessary.

Figure 19:
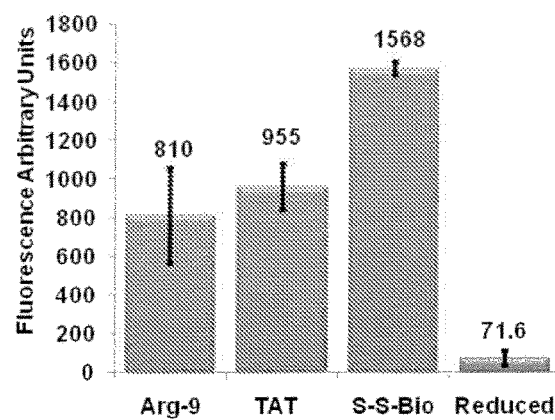
FIG. 19 shows the quantification of peptide uptake via flow cytometry. Shown is a comparison of the uptake efficiency of peptide 1 via biotin shuttling vs. TAT and polyarginine delivery. As a control, peptide 1 was used that had been reduced and desalted prior to administration. "Arg-9" is disclosed as SEQ ID NO: 70.

Flow cytometry experiments were subsequently employed to compare biotin mediated delivery to those of cationic peptides. Truncations of HIV TAT protein has been shown to be capable of delivering cargo to cells. Wadia, J. S., (2004) Nat. Med. 10:310. Additionally polyarginine sequences are thought to delivery cargo via a similar mechanism. To compare their efficiencies to biotin shuttling, two additional variants of peptide 1 were synthesized. One contained an N-terminal TAT$_{(47-57)}$ sequence, and the other had 9 N-terminal Arg residues. All peptides had a fluorescein at the N-terminus Flow cytometry was employed to quantitate uptake efficiency. FIG. 19 show that biotin mediated deliver and disulfide release was 1.6 fold as efficient as TAT under standard conditions.

Figures 20A, 20B:
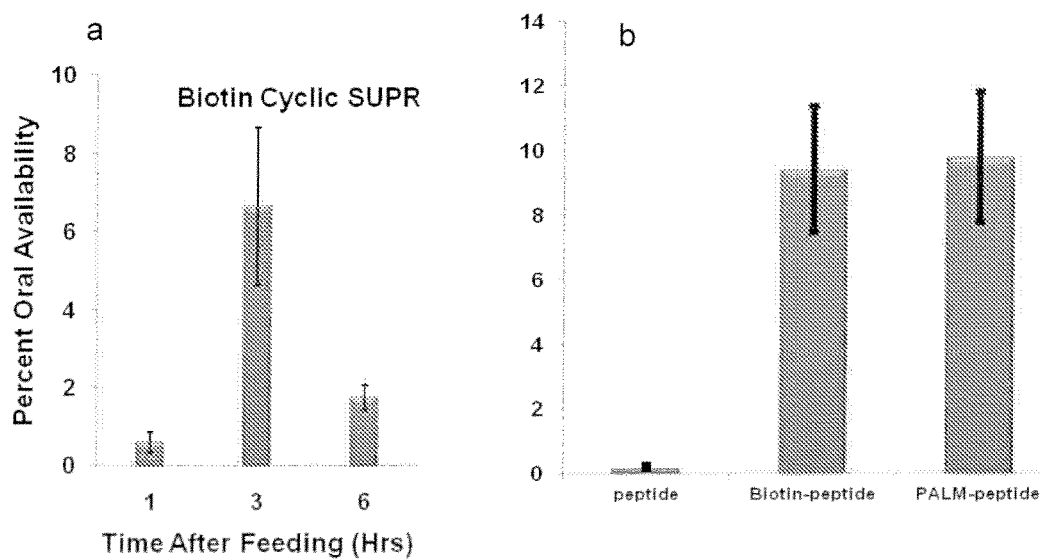
FIGS. 20A and 20B show biotinylation and palmitoleic acid conjugation enhances oral bioavailability.

In addition to accessing intracellular targets in cell culture, deriving a simple modification that would facilitate oral bioavailability of peptidic ligands would be greatly beneficial for therapeutic development. Intestinal absorption of both fatty acids and biotin is nearly 100% efficient. Zempleni, J. and Mock, D. M. (1999) The American Journal of Clinical Nutrition 69:504. Therefore, Applicants theorized that stable peptides with either a biotin or fatty acid conjugation would exhibit some oral bioavailability. Applicants synthesized a protease resistant peptide with the sequence MFYAYEYAQWSKK-mod (designated SUPR peptide) (SEQ ID NO: 50), where A is N-methyl alanine, the peptide is cyclized from lysine to the N-terminus, and K(mod) is lysine with a modified sidechain including either biotin or palmitoleic acid. Palmitoleic acid is a monounsaturated fatty acid chosen for its ability to bind human serum albumin, and its low melting point allowing for more favorable solubility of conjugated peptides as compared to unsaturated fatty acid conjugates. This peptide was administered to mice at a dose of 10 mg/kg by oral gavage. At various time points, blood was taken from the mice by orbital bleeding. After processing, fluorescence was quantified and compared to the maximum signal obtained by IV injection of peptide at the same dose. 3 hours after administration, there was a maximum peptide signal corresponding to 9.4% bioavailability for biotinylated peptide and 9.8% bioavailability for peptide conjugated to fatty acid as can be seen in FIG. 20.

Figures 21A, 21B, 21C:
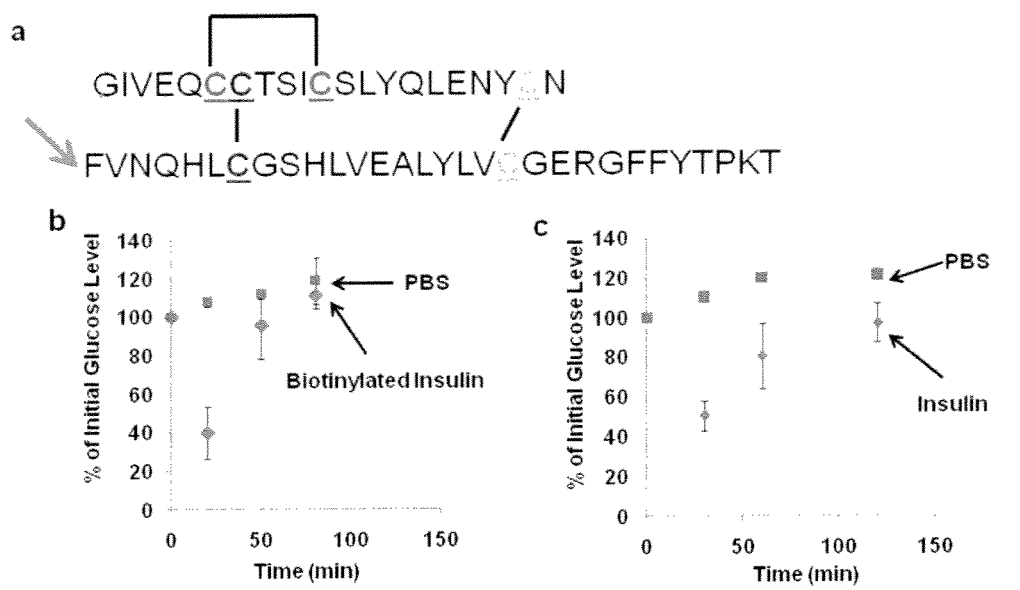
FIGS. 21A to 21C show biotinylated insulin regulates blood sugar levels in vivo.
Figure 22:
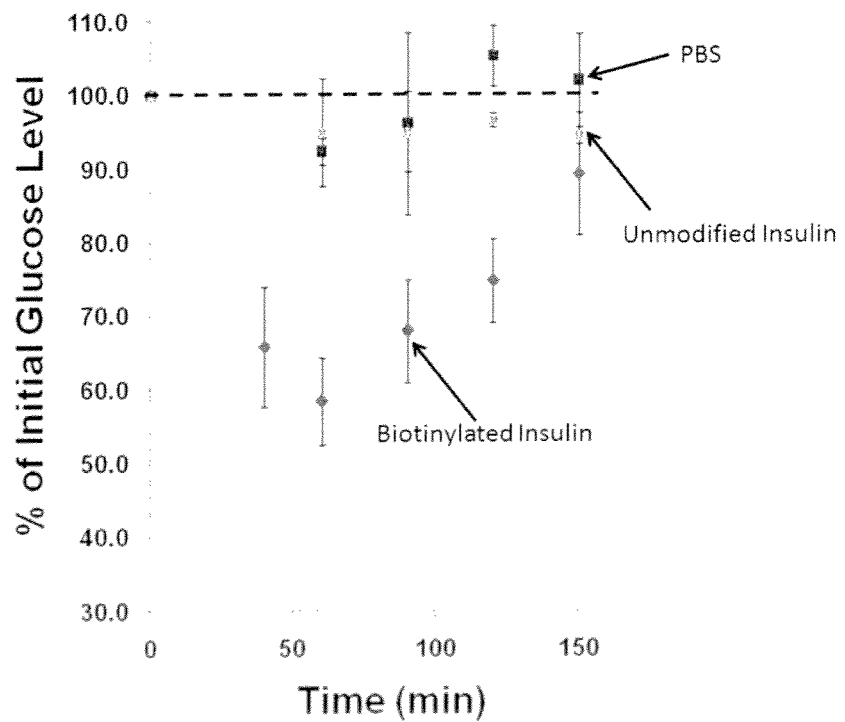
FIG. 22 shows oral bioavailability of biotinylated insulin.

Reacting human insulin with biotin-NHS produced three distinct products that can be separated by HPLC. Two peaks showed single modifications and the third a double modification as determined by MALDI-TOF. Both single modifications were examined for in vivo function, but peak 2 was found to be more efficacious. Chymotrypsin digest and subsequent MALDI analysis showed that the site of biotinylation was on the N-terminus of the B-chain. This agrees with the literature president that modification at this position does not alter efficacy. Calceti, P. et al. (2004) European Journal of Pharmaceutical Sciences 22:315; and Tuesca, A., et al. (2009) Pharmaceutical Research 26:727. Intravenous injection of this compound at a dose of 3.5 nmol/kg showed a similar effect on blood sugar as unmodified insulin both in terms of total intensity of response, and duration of that response (FIG. 21).

Biotinylated insulin and insulin were fed to mice by oral gavage. At a dose of 7 nmol/kg, insulin had no effect on blood sugar. However biotinylated insulin administered orally produced a typical insulin response. The longer duration of response is likely due to the kinetics of absorption by the intestinal mucosa.

In addition to biotin, Applicants' data suggests that any highly bioavailable small molecule could deliver similar results. These include other vitamins, saturated or unsaturated fatty acids, hydrophobic small molecules, and saturated and unsaturated hydrocarbons and could be at the N-terminus of the B-chain or the side chain of Lys. Additionally, other insulin derivatives and analogs such as insulin lispro and insulinotropic compounds such as GLP-1 analogs could be modified by the inclusion of a biotin for the purpose of blood sugar regulation.

Applicants were also investigating if the significant stability of cycSUPR would better translate into in vivo stability than the natural peptides sequences tested. Previous work showed that sarcosine polymers (N-methyl glycine) showed significant in vivo half-life enhancements with respect to glycine polymers. It was suspected that this was due to a resistance to renal clearance that the sarcosine conferred on the peptides. To that end mice were administered peptide conjugated to fluorescein by IV injection into the tail vein. Blood samples were taken by orbital bleeding. Blood peptide concentration was determined by comparing fluorescence to a 15 minute time point. A dramatic enhancement in the stability of SUPR in vivo was found. CycGIBP showed a half-life of 3.1 minutes while cycSUPR peptide had a half-life of 110 minutes, or a roughly 35 fold increase in half-life. The discrepancy in half-life between the serum data and the in vivo data is likely due to renal clearance. Previous work has shown that conjugating a peptide to a small molecule that has affinity for serum albumin can significantly lower the clearance rate of a peptide. Albumin, which has a concentration ranging from 500-800 μM in blood, has a nanomolar affinity for C-14 to C-18 fatty acids. However, initial attempts to synthesize peptide with fatty acid conjugates resulted in molecules with poor solubilities in conditions necessary for in vivo work. A single cis-unsaturation in the C-16 fatty acid palmitoleic acid results in a reduction of melting point from 63° C. to 0° C. Fatty acids with single unsaturations also retain nanomolar binding affinity towards albumin. Applicants found that peptides conjugation to palmitoleic acid retained sufficient solubility in these experiments. Additionally, there was a significant increase in the in vivo half-life. CycSUPR peptide containing this modification at the C-terminus exhibited an order of magnitude increase in half-life, 1100 minutes, 354 fold higher than cycGIBP as may be noted in FIG. 20.

There are examples of NRPs that are orally bioavailable. Cyclosporin is one such example showing 25% oral bioavailability. However, designed peptides rarely show any significant oral uptake. One of the most efficient examples is a stapled helix designed by Walensky et al. (2004), supra. Even in this case, oral availability was limited, less than 0.2% uptake. Applicants wanted to determine the efficiency of oral uptake of our peptide in comparison to what has been noted in the field. Applicants examined SUPR peptide with and without the addition of the palmitoleic acid residue. Applicants also examined SUPR peptide containing a C-terminal biotinylation. SUPR peptide without modification did not show any detectable oral uptake, as Applicants anticipated. However, both biotin and palmitoleic acid have nearly 100% oral bioavailabilities. The peptides made by the method of this disclosure can be further modified by conjugation with biotin or a biotin analog, as described in Example 3. Therefore, Applicants postulated that peptides conjugated to these molecules would exhibit some oral availability. In fact, this is precisely what Applicants found as outlined in FIG. 21. After a single oral administration, there seemed to be a maximal uptake of biotinylated peptide at 3 hrs. The C-terminal biotinylation and palmitoleic acid conjugation showed an oral uptake efficiency of 6.4% and 9.4% respectively, which is well within the acceptable range of therapeutics. Further optimization could likely be achieved by using standard formulation techniques such as the microencapsulation techniques employed for enhancing cyclosporine delivery.

Experiment No. 4

Figure 23:
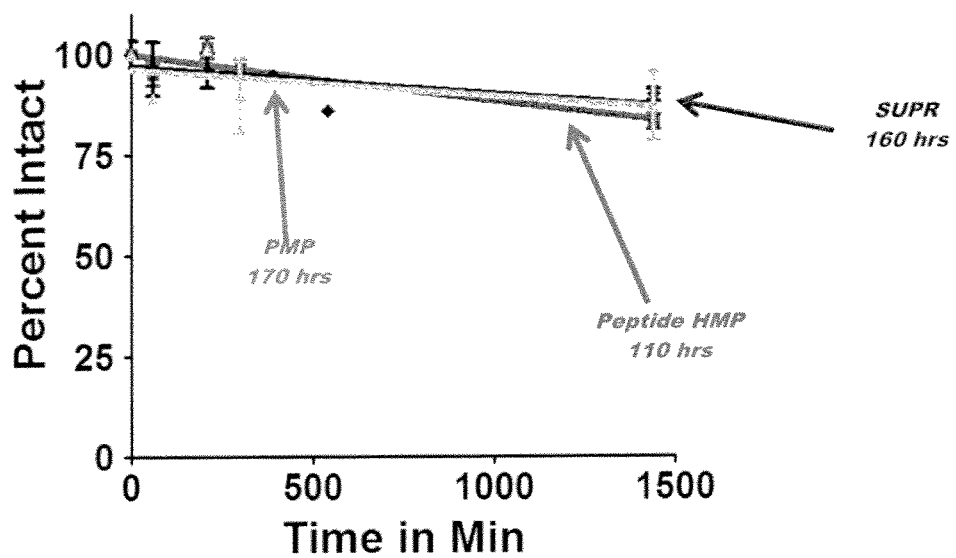
FIG. 23 shows half-life of peptides digested in human serum. Peptide (n=3) were digested in 95% human serum at 37° C. PMP (■), HMP(■), and SUPR(♦) peptides are shown.

The human serum and human microsome stability of the Gαi1 binding SUPR peptide (MFY$\underline{A}$YEY$\underline{A}$QWSK (SEQ ID NO: 7)) were compared to the peptides ability to bind to Her-2. Beginning with the human serum analysis, peptides were digested with 95% human serum at 37° C. Analysis was performed by HPLC. Any modification to the peptide resulted in a change in retention time, and was subtracted from the sample. Therefore, intact peptide is only completely unmodified peptide. Digestions of SUPR, HMP, and PMP are show have lives very similar to SUPR. Digestion of PMP2 is in progress. Data is shown in FIG. 23. Without being bound by theory, Applicants theorize that the fitting for HMP may have produced an artificially low half-life. However, all peptides exhibited half-lives of over 100 hrs under stringent digestion conditions.

Figure 24:
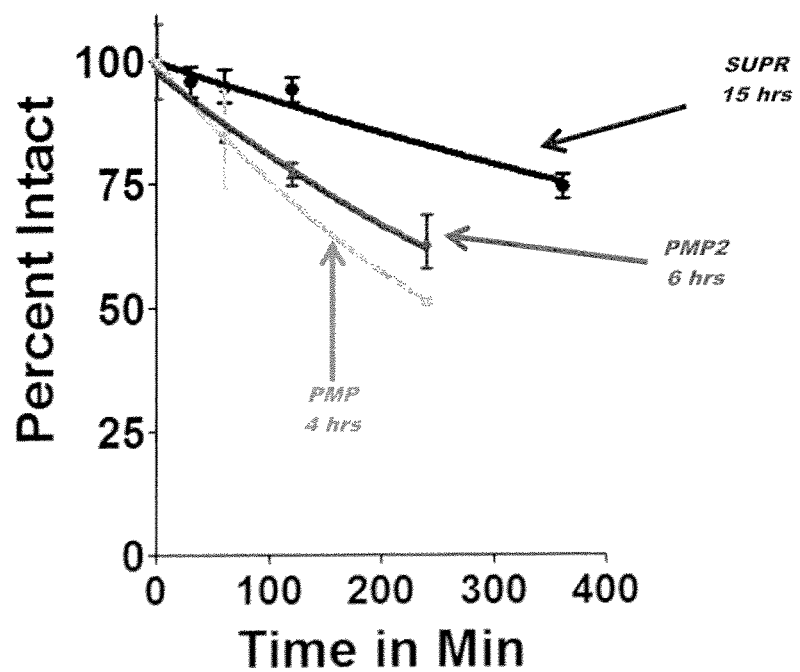
FIG. 24 shows the half-life of peptides processed by human liver microsomes. Peptide (n=3) were digested in 95% human serum at 37° C. PMP (■), HMP(▲), and SUPR(●) peptides are shown.

A similar experiment was performed analyzing protease resistance to cytochrome P450 degradation. Peptide was incubated with human liver microsomes at 37° C. All peptides were highly protease resistant. However, SUPR was more preotease resistant than the Her-2 binding peptides. The selection for SUPR peptide was performed with a more stringent proteolytic pressure. This seems to indicate that cytochrome P450 degradation can be further enhanced during the selection process by dialing up the protease selective pressure step. Data for these peptides are illustrated in FIG. 24.

Structural Analysis by Circular Dichroism

Figures 25A, 25B, 25C, 25D:
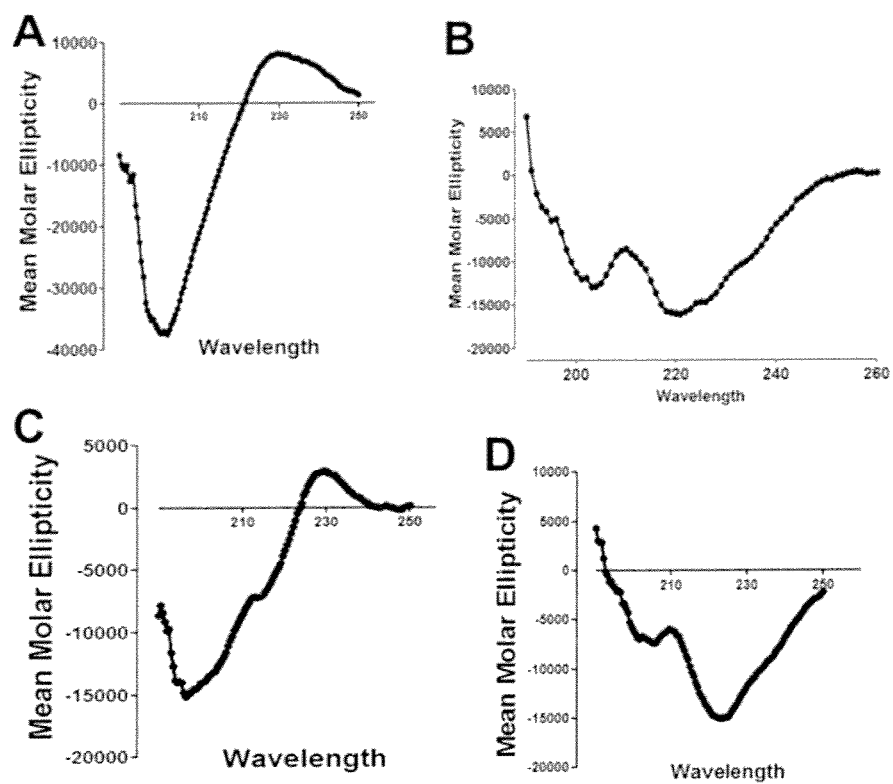
FIGS. 25A through 25D show a method to produce structured peptides as explained in Experiment No. 4.
Figures 26A, 26B, 26C, 26D, 26E:
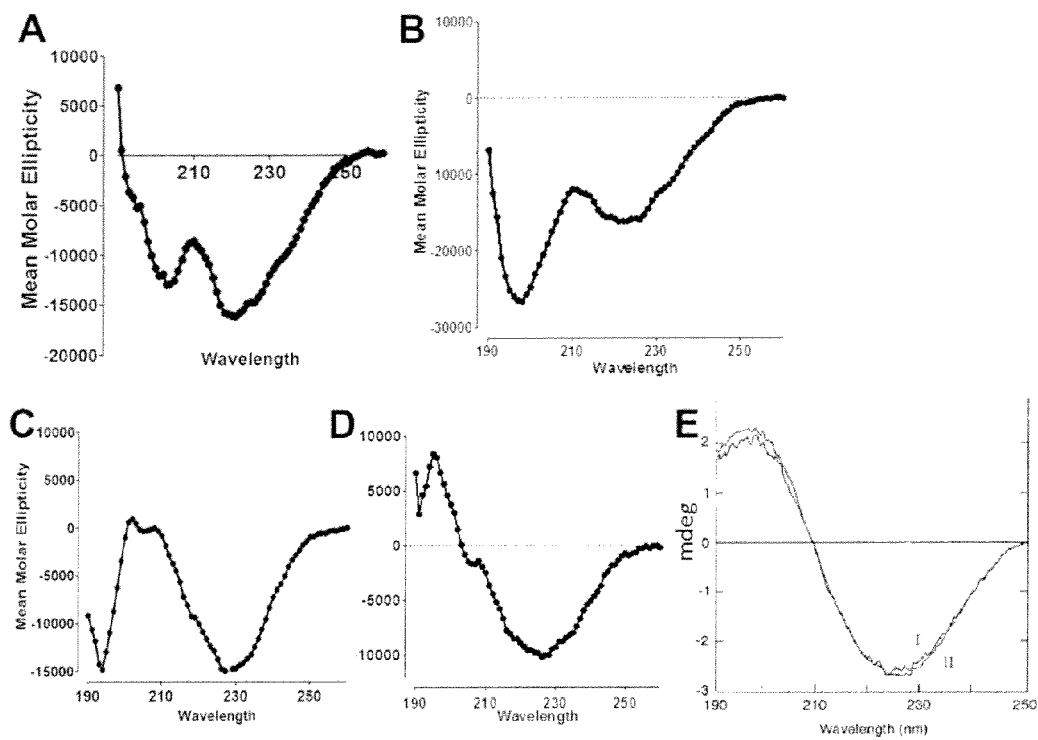
FIGS. 26A through 26E show that SUPR peptides are structured.

To show that the structure of the SUPR peptides might contribute to stability, Applicants conducted circular dichroism ("CD") experiments. Peptide at 50 µM concentration was dissolved in 50 mM potassium phosphate buffer. CD experiments followed standard protocols, and were conducted at 20° C. cycGIBP, a cyclic peptide that binds Gαi1 with 2 nM affinity, seemed to be entirely unstructured (FIG. 25A). All stabilized peptides were structured. In the case of SUPR peptide, the compound seems helical (FIG. 25B). Peptides binding to Gαi1 have sequence similarity, and have been shown to be helical in crystal structure data. Therefore this structural motif would be expected in SUPR peptide Another interesting finding is that SUPR peptide is structured both as a linear and a cyclic peptide (FIGS. 25B and 25D). However, removal of one or both N-methylations results in a nearly complete loss of structure (FIG. 25D). The Her-2 binding peptide have a CD signal characteristic of a β-turn. In fact, PMP's spectra extremely similar to that of cyclosporine. The data is shown in FIG. 26.

Analyzing the Toxicity of the Stabilized Peptides

An mtt assay was performed to examine the effect of our peptides on cell that do not overexpress Her-2. Standard protocols were followed. Briefly, 100,000 HEK293T cells were seeded per well in a 96 well plate, and cultured with D10 media. Peptide at various concentrations was administered for 36 hr. mtt analysis followed manufacturer's instructions The experiment was performed in triplicate. Plotted is the average and standard deviation.

Figure 27:
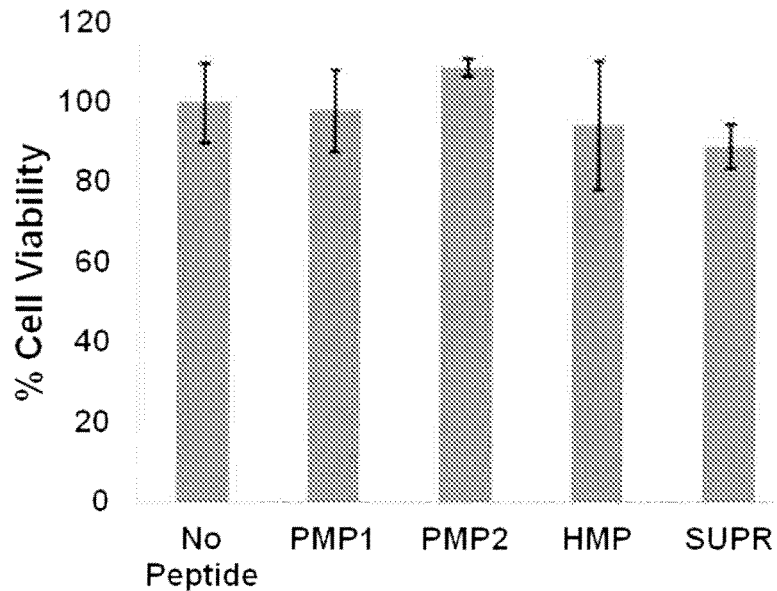
FIG. 27 shows the results of analysis of toxicity of peptides as analyzed by mtt. Peptide (n=3) was administered at 100 μM for 36 hours. DMSO concentration was 1% by volume. Cells were analyzed using a Abnova mtt assay kit. Plotted are the average values, and error in standard deviation.

There was no apparent toxicity when peptide was administered up to 100 µM (FIG. 27). The DMSO concentration of all samples was 1% by volume. Toxicity as measure against liver cells is planned.

Analyzing the Immunogenicity of Stabilized Peptides

Immune response was tested to the repeated administration of our peptide samples. Two peptides were initially tested: SUPR and cycGIBP. Both of these peptides bind to Gαi1 with high affinity. However, only SUPR peptide has been stabilized.

3 mice per group (C57BL) were tested. 100 µgs of peptide was administered with Freund's adjuvant to help elicit an immune response. Peptide was administered every other week for 8 weeks. At week 10, blood samples were taken for analysis.

Analysis followed published protocols. Serum from mice is stored at −80° C. until needed. An ELISA assay was performed using streptavidin coated plates. Plates were incubated with biotinylated peptide followed by serial dilutions of serum stock (from 1× to 1/2000). After incubation and washing, anti-mouse antibody conjugated with HRP was added. After washing again, substrate solution was added for 15 followed by developing (stop) solution. Absorbance was measured at 450 nM.

Figure 28:
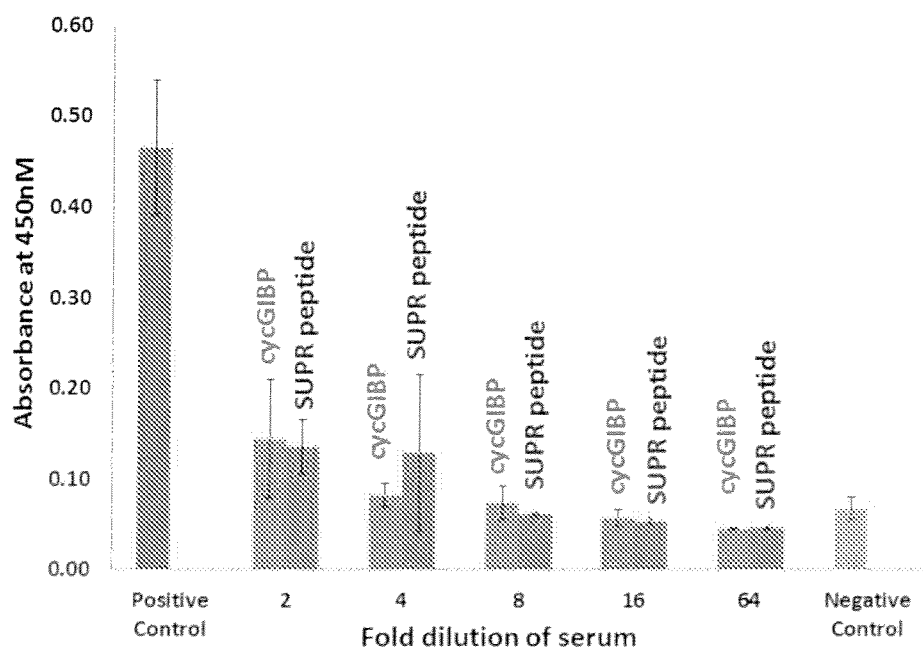
FIG. 28 shows immunogenicity of cycGIBP and SUPR with Freund's partial adjuvant (n=3). Positive control is biotinylated mouse antibody. Negative control is biotin. cycGIBP in blue, and SUPR peptide in red. Plotted are the average values and standard deviation.

As a positive control, the above protocol was followed substituting biotinylated mouse antibody for biotinylated peptide. The negative control used no biotinylated product (peptide or antibody). There seems to be a very low signal for immunogenicity (FIG. 28).

Amino acids are identified by single letter codes or three letter codes. For the sake of clarity, the abbreviations and codes identify the following amino acids.

| 1-Letter | 3-Letter | Amino Acid |
| --- | --- | --- |
| Y | Tyr | tyrosine |
| G | Gly | glycine |
| F | Phe | phenylalanine |

| 1-Letter | 3-Letter | Amino Acid |
|---|---|---|
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A non-naturally occurring peptide comprising:
MAXYXHYHK, (SEQ. ID NO: 81) wherein the X at positions 3 and 5 is N-methyl norvaline; or
MVCXXLYDDK, (SEQ ID NO: 82) wherein the X at positions 4 and 5 is N-methyl norvaline.

2. A non-naturally occurring peptide of claim 1, wherein the peptide is biotinylated at the N-terminal or C-terminal end.

3. A peptide conjugate comprising a non-naturally occurring peptide of claim 1, wherein the peptide is conjugated to polyethylene glycol or a lipid molecule.

4. A composition comprising a non-naturally occurring peptide of claim 1 and a carrier.

5. The composition of claim 4, wherein the carrier is a pharmaceutically acceptable carrier.

6. A method for inhibiting the growth of a breast cancer cell, comprising contacting the cell with an effective amount of a non-naturally occurring peptide of claim 1, wherein the breast cancer cell is HER2+.

7. A method for treating breast cancer in subject in need thereof, comprising administering to the subject an effective amount of a non-naturally occurring peptide of claim 1, wherein the breast cancer cell is HER2+.

8. A method for detecting HER2+ a breast cancer cell in a subject comprising administering to the subject a non-naturally occurring peptide of claim 1 and screening for the presence of any of the peptide bound to a HER2+ breast cancer cell in the subject.

9. The method of claim 8, wherein the non-naturally occurring peptide is detectably labeled.

10. The method of claim 9, wherein the label is a fluorescent dye or a PET label.

11. A vector comprising an isolated nucleic acid encoding the peptide of claim 1, wherein N-methyl norvaline is encoded by a stop codon.

12. A method for producing a non-naturally occurring peptide of claim 1 comprising translating an isolated nucleic acid encoding said peptide in rabbit reticulocyte lysate, wherein said lysate is supplemented with a suppressor tRNA charged with N-methyl norvaline, and wherein N-methyl norvaline is encoded by a stop codon complimentary to said suppressor tRNA.

13. The method of claim 12, further comprising isolating the non-naturally occurring peptide from the lysate.

14. A method for determining if a candidate agent is a potential therapeutic to inhibit the growth of a HER2+ breast cancer cell, comprising: contacting the candidate agent with a breast cancer cell and assaying for growth inhibitory activity, and comparing the inhibitory activity of the candidate agent with the inhibitory activity of: the non-naturally occurring peptide of claim 1.

15. A kit for one or more of: inhibiting the growth of a breast cancer cell or for treating breast cancer, or for determining if a candidate agent is a potential therapeutic to inhibit the growth of a cancer cell, comprising the non-naturally occurring peptide of claim 1 and instructions for use.

* * * * *

UNITED STATES PATENT AND TRADEMARK OFFICE
CERTIFICATE OF CORRECTION

PATENT NO. : 9,944,675 B2
APPLICATION NO. : 14/342347
DATED : April 17, 2018
INVENTOR(S) : Fiacco et al.

Page 1 of 1

It is certified that error appears in the above-identified patent and that said Letters Patent is hereby corrected as shown below:

In the Specification

In Column 1, Lines 18-21, please delete "This invention was made with government support under National Institutes of Health grant number R01 GM 60416. Accordingly, the U.S. Government has certain rights to this invention." and insert -- This invention was made with government support under GM 060416 awarded by the National Institutes of Health (NIH). The government has certain rights in the invention. --

Signed and Sealed this
First Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 82

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Norvaline, Ala or Norleucine
<220> FEATURE:
<221> NAME/KEY: MOD_RES
<222> LOCATION: (2)..(2)
<223> OTHER INFORMATION: Ala, any N-methyl amino acid, any modified
      amino acid that confers stabilization to the peptide, Met, Ser,
      Thr, His, Lys, Arg, Gln, Asn, Leu, Val or Ile
<220> FEATURE:
<221> NAME/KEY: MOD_RES
<222> LOCATION: (3)..(3)
<223> OTHER INFORMATION: N-methyl Norvaline, any N-methyl amino acid,
      any modified amino acid that confers stabilization to the peptide,
      Ser, Thr, Gln, Asn, His, Ile, Val, Leu, Tyr, Phe or Pro
<220> FEATURE:
<221> NAME/KEY: MOD_RES
<222> LOCATION: (4)..(4)
<223> OTHER INFORMATION: Tyr, any N-methyl amino acid, any modified
      amino acid that confers stabilization to the peptide, Phe, Gln,
      Asn, Ser, Thr or His
<220> FEATURE:
<221> NAME/KEY: MOD_RES
<222> LOCATION: (5)..(5)
<223> OTHER INFORMATION: N-methyl Norvaline, any N-methyl amino acid,
      any modified amino acid that confers stabilization to the peptide,
      Tyr, Phe, Ser, Thr, Glu, Asp, Met, Ala or Pro
```

```
<220> FEATURE:
<221> NAME/KEY: MOD_RES
<222> LOCATION: (6)..(6)
<223> OTHER INFORMATION: His, any N-methyl amino acid, any modified
      amino acid that confers stabilization to the peptide, Tyr, Phe,
      Gln or Asn
<220> FEATURE:
<221> NAME/KEY: MOD_RES
<222> LOCATION: (7)..(7)
<223> OTHER INFORMATION: His, any N-methyl amino acid, any modified
      amino acid that confers stabilization to the peptide, Phe, Tyr,
      Val, Ile or Leu
<220> FEATURE:
<221> NAME/KEY: MOD_RES
<222> LOCATION: (8)..(8)
<223> OTHER INFORMATION: His or any amino acid
<220> FEATURE:
<221> NAME/KEY: MOD_RES
<222> LOCATION: (9)..(9)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Norvaline, Norleucine or Ala
<220> FEATURE:
<221> NAME/KEY: MOD_RES
<222> LOCATION: (2)..(2)
<223> OTHER INFORMATION: Phe or any amino acid
<220> FEATURE:
<221> NAME/KEY: MOD_RES
<222> LOCATION: (3)..(3)
<223> OTHER INFORMATION: N-methyl Norvaline, Gln, Asn, Ser, Thr, His,
      Tyr, Phe, Pro, any N-methyl amino acid or any modified amino acid
      that confers stabilization to the peptide
<220> FEATURE:
<221> NAME/KEY: MOD_RES
<222> LOCATION: (4)..(4)
<223> OTHER INFORMATION: Gln, Tyr, Phe, any N-methyl amino acid, any
      modified amino acid that confers stabilization to the peptide,
      Pro, Ser or Thr
<220> FEATURE:
<221> NAME/KEY: MOD_RES
<222> LOCATION: (5)..(5)
<223> OTHER INFORMATION: N-methyl Norvaline, Tyr, Phe, Ser, Thr, Asp,
      Glu, Ala, Met, any N-methyl amino acid or any modified amino acid
      that confers stabilization to the peptide
<220> FEATURE:
<221> NAME/KEY: MOD_RES
<222> LOCATION: (6)..(6)
<223> OTHER INFORMATION: Tyr, Phe or His
<220> FEATURE:
<221> NAME/KEY: MOD_RES
<222> LOCATION: (7)..(7)
<223> OTHER INFORMATION: Tyr, Phe, Leu, Ile, Val, Ser, Thr, any N-methyl
      amino acid, or any modified amino acid that confers stabilization
      to the peptide
<220> FEATURE:
<221> NAME/KEY: MOD_RES
<222> LOCATION: (8)..(8)
<223> OTHER INFORMATION: His, Thr or Ser
<220> FEATURE:
<221> NAME/KEY: MOD_RES
```

```
<222> LOCATION: (9)..(9)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Norvaline, Norleucine or Ala
<220> FEATURE:
<221> NAME/KEY: MOD_RES
<222> LOCATION: (2)..(2)
<223> OTHER INFORMATION: Leu, Ile or Val
<220> FEATURE:
<221> NAME/KEY: MOD_RES
<222> LOCATION: (3)..(3)
<223> OTHER INFORMATION: His, Tyr or Phe
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: N-methyl Norvaline, Ser, Thr, Asp, Glu, Ala,
      Met, Pro, any N-methyl amino acid or any modified amino acid that
      confers stabilization to the peptide
<220> FEATURE:
<221> NAME/KEY: MOD_RES
<222> LOCATION: (6)..(6)
<223> OTHER INFORMATION: Tyr, His, Gln, Asn, Leu, Ile, Val, any N-methyl
      amino acid or any modified amino acid that confers stabilization
      to the peptide
<220> FEATURE:
<221> NAME/KEY: MOD_RES
<222> LOCATION: (7)..(7)
<223> OTHER INFORMATION: N-methyl Norvaline, Phe, Tyr, Leu, Ile, Val,
      His, Pro, any N-methyl amino acid or any modified amino acid that
      confers stabilization to the peptide
<220> FEATURE:
<221> NAME/KEY: MOD_RES
<222> LOCATION: (8)..(8)
<223> OTHER INFORMATION: Arg or any amino acid
<220> FEATURE:
<221> NAME/KEY: MOD_RES
<222> LOCATION: (9)..(9)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 3

Xaa Xaa Xaa Xaa Xaa Xaa Xaa Xaa Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Met, Norvaline, Norleucine or Ala
<220> FEATURE:
<221> NAME/KEY: MOD_RES
<222> LOCATION: (2)..(2)
<223> OTHER INFORMATION: Val, Ile or Leu
<220> FEATURE:
<221> NAME/KEY: MOD_RES
<222> LOCATION: (4)..(4)
<223> OTHER INFORMATION: N-methyl Norvaline, Tyr, Phe, Pro, Asp, Glu,
      Met, any N-methyl amino acid or any modified amino acid that
      confers stabilization to the peptide
<220> FEATURE:
<221> NAME/KEY: MOD_RES
<222> LOCATION: (5)..(5)
<223> OTHER INFORMATION: N-methyl Norvaline, Tyr, Phe, Asp, Glu, Trp,
      Cys, Gly, Pro, any N-methyl amino acid or any modified amino acid
      that confers stabilization to the peptide
<220> FEATURE:
<221> NAME/KEY: MOD_RES
<222> LOCATION: (6)..(6)
<223> OTHER INFORMATION: Leu, Tyr, Phe, any N-methyl amino acid, any
      modified amino acid that confers stabilization to the peptide,
      Val, Ile, Pro or Cys
<220> FEATURE:
<221> NAME/KEY: MOD_RES
<222> LOCATION: (7)..(7)
<223> OTHER INFORMATION: Tyr, any N-methyl amino acid, any modified
      amino acid that confers stabilization to the peptide, Glu or Asp
<220> FEATURE:
<221> NAME/KEY: MOD_RES
<222> LOCATION: (8)..(8)
<223> OTHER INFORMATION: Asp, Ser, Thr, Glu, Tyr, Phe, Ala, Pro, any
      N-methyl amino acid or any modified amino acid that confers
      stabilization to the peptide
<220> FEATURE:
<221> NAME/KEY: MOD_RES
<222> LOCATION: (9)..(9)
<223> OTHER INFORMATION: Asp, Glu, Gly, Leu, Ile or Val
<220> FEATURE:
<221> NAME/KEY: MOD_RES
<222> LOCATION: (10)..(10)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 4

Xaa Xaa Cys Xaa Xaa Xaa Xaa Xaa Xaa Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Norvaline, Norleucine or Ala
<220> FEATURE:
<221> NAME/KEY: MOD_RES
<222> LOCATION: (2)..(2)
<223> OTHER INFORMATION: Glu or any amino acid
<220> FEATURE:
<221> NAME/KEY: MOD_RES
<222> LOCATION: (3)..(3)
<223> OTHER INFORMATION: N-methyl Norvaline, Pro, Asp, Glu, Phe, Tyr,
      Ser, Thr, Gln, Asn, any N-methyl amino acid or any modified amino
      acid that confers stabilization to the peptide
<220> FEATURE:
<221> NAME/KEY: MOD_RES
<222> LOCATION: (4)..(4)
<223> OTHER INFORMATION: Tyr, Asp, Glu, Phe, any N-methyl amino acid,
```

```
        any modified amino acid that confers stabilization to the peptide
        or Pro
<220> FEATURE:
<221> NAME/KEY: MOD_RES
<222> LOCATION: (5)..(5)
<223> OTHER INFORMATION: Glu, Asp, Tyr, Phe, Pro, any N-methyl amino
      acid or any modified amino acid that confers stabilization to the
      peptide
<220> FEATURE:
<221> NAME/KEY: MOD_RES
<222> LOCATION: (6)..(6)
<223> OTHER INFORMATION: Tyr, Phe, Leu, Val, Ile, Pro, any N-methyl
      amino acid or any modified amino acid that confers stabilization
      to the peptide
<220> FEATURE:
<221> NAME/KEY: MOD_RES
<222> LOCATION: (7)..(7)
<223> OTHER INFORMATION: N-methyl Norvaline, Phe, Leu, Val, Ile, Pro,
      any N-methyl amino acid or any modified amino acid that confers
      stabilization to the peptide
<220> FEATURE:
<221> NAME/KEY: MOD_RES
<222> LOCATION: (8)..(8)
<223> OTHER INFORMATION: Ser or any amino acid
<220> FEATURE:
<221> NAME/KEY: MOD_RES
<222> LOCATION: (9)..(9)
<223> OTHER INFORMATION: Leu or any amino acid
<220> FEATURE:
<221> NAME/KEY: MOD_RES
<222> LOCATION: (10)..(10)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 5

Xaa Xaa Xaa Xaa Xaa Xaa Xaa Xaa Xaa Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Norvaline, Norleucine or Ala
<220> FEATURE:
<221> NAME/KEY: MOD_RES
<222> LOCATION: (2)..(2)
<223> OTHER INFORMATION: Asn or any amino acid
<220> FEATURE:
<221> NAME/KEY: MOD_RES
<222> LOCATION: (3)..(3)
<223> OTHER INFORMATION: Glu, Asp, Ile, Val, Leu, Phe, Tyr, Pro, any
      N-methyl amino acid or any modified amino acid that confers
      stabilization to the peptide
<220> FEATURE:
<221> NAME/KEY: MOD_RES
<222> LOCATION: (4)..(4)
<223> OTHER INFORMATION: Tyr, Asp, Glu, Pro, any N-methyl amino acid or
      any modified amino acid that confers stabilization to the peptide
<220> FEATURE:
<221> NAME/KEY: MOD_RES
<222> LOCATION: (5)..(5)
<223> OTHER INFORMATION: N-methyl Norvaline, Asp, Glu, Phe, Tyr, Gly,
      Cys, Pro, any N-methyl amino acid or any modified amino acid that
      confers stabilization to the peptide
<220> FEATURE:
<221> NAME/KEY: MOD_RES
<222> LOCATION: (6)..(6)
<223> OTHER INFORMATION: Leu, Tyr, Phe, Pro, any N-methyl amino acid or
      any modified amino acid that confers stabilization to the peptide
```

```
<220> FEATURE:
<221> NAME/KEY: MOD_RES
<222> LOCATION: (7)..(7)
<223> OTHER INFORMATION: Tyr, Phe, Val, Ile or Leu
<220> FEATURE:
<221> NAME/KEY: MOD_RES
<222> LOCATION: (8)..(8)
<223> OTHER INFORMATION: N-methyl Norvaline, Ser, Thr, Tyr, Phe, Glu,
      Asp, Ala, Pro, any N-methyl amino acid or any modified amino acid
      that confers stabilization to the peptide
<220> FEATURE:
<221> NAME/KEY: MOD_RES
<222> LOCATION: (9)..(9)
<223> OTHER INFORMATION: Leu, Lys, Arg, Ile, Val, Asp, Glu, Gly, Ser or
      Thr
<220> FEATURE:
<221> NAME/KEY: MOD_RES
<222> LOCATION: (10)..(10)
<223> OTHER INFORMATION: Lys or any Lys derivatives
<220> FEATURE:
<223> OTHER INFORMATION: See specification as filed for detailed
      description of substitutions and preferred embodiments

<400> SEQUENCE: 6

Xaa Xaa Xaa Xaa Xaa Xaa Xaa Xaa Xaa Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Ala
<220> FEATURE:
<221> NAME/KEY: MOD_RES
<222> LOCATION: (8)..(8)
<223> OTHER INFORMATION: N-methyl Ala

<400> SEQUENCE: 7

Met Phe Tyr Ala Tyr Glu Tyr Ala Gln Trp Ser Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Ala
<220> FEATURE:
<221> NAME/KEY: MOD_RES
<222> LOCATION: (8)..(8)
<223> OTHER INFORMATION: N-methyl Ala
<220> FEATURE:
<221> NAME/KEY: MOD_RES
<222> LOCATION: (13)..(13)
<223> OTHER INFORMATION: Lys with a modified side chain including
      biotin, a biotin analog or palmitoleic acid

<400> SEQUENCE: 8

Met Phe Tyr Ala Tyr Glu Tyr Ala Gln Trp Ser Lys Lys
1               5                   10

<210> SEQ ID NO 9
```

<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
attatgctga gtgatatcca agatatcata tcgccaatca tgaccccctga gatttaggga     60 actggaccca agcttagggt catcctggag                                       90

<210> SEQ ID NO 10
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10
gggacaatta ctatttacaa ttacaatgww kwmstrgtak kartwkkwgk mgkrswmsaa       60
atctggaagt ggaagtgga                                                   79

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
taatacgact cactataggg acaattacta tttacaatta ca                         42

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ccacttccac ttccagattt                                                  20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tttttttttt tttccacttc cact                                             24

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (13)..(13)
<223> OTHER INFORMATION: Lys(FAM)

```
<220> FEATURE:
<223> OTHER INFORMATION: See specification as filed for detailed
      description of substitutions and preferred embodiments

<400> SEQUENCE: 14

Met Phe Tyr Val Tyr Glu Tyr Val Gln Trp Ser Lys Lys
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys(FAM)
<220> FEATURE:
<221> NAME/KEY: MOD_RES
<222> LOCATION: (15)..(15)
<223> OTHER INFORMATION: Lys(Palmitoleic acid)
<220> FEATURE:
<223> OTHER INFORMATION: See specification as filed for detailed
      description of substitutions and preferred embodiments

<400> SEQUENCE: 15

Met Phe Tyr Val Tyr Glu Tyr Val Gln Trp Ser Lys Lys Asp Lys
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys(FAM)
<220> FEATURE:
<223> OTHER INFORMATION: See specification as filed for detailed
      description of substitutions and preferred embodiments

<400> SEQUENCE: 16

Met Ile Thr Trp Tyr Glu Phe Val Ala Gly Thr Lys Lys
1               5                   10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 5' biotin

<400> SEQUENCE: 17
tttggaccac tgctaatact catactagta aaacat                               36

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 18

Phe Tyr Val Tyr Glu Tyr Val Gln Trp Ser
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ile Thr Trp Tyr Glu Phe Val Ala Gly Thr Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: N-methyl Ala

<400> SEQUENCE: 20

Met Phe Tyr Ala Tyr Glu Tyr Ala Gln Trp Ser Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Ala

<400> SEQUENCE: 21

Met Phe Tyr Ala Tyr Glu Tyr Ala Gln Trp Ser Lys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Phe Tyr Ala Tyr Glu Tyr Ala Gln Trp Ser Lys
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (3)..(3)
<223> OTHER INFORMATION: Any N-methyl amino acid

<400> SEQUENCE: 23

Met Phe Xaa Phe Phe
1               5

<210> SEQ ID NO 24
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (50)..(51)
<223> OTHER INFORMATION: a, c, t, g, unknown or other

<400> SEQUENCE: 24
gggacaatta ctatttacaa ttacaatgnn skrskakkrk twstakkmsn nsaaaagtag     60
tggtagcagc gattaca                                                   77

<210> SEQ ID NO 25
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other

<400> SEQUENCE: 25
gggacaaata ctatttacaa ttacaatgnn symkyakkmk yastwknnsa aaagtagtgg     60
tagcagcgat taca                                                      74

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgtaatcgct gctaccacta ctttt                                          25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
```
tttttttttt ttttgtaatc gctgc                                          25

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline

<400> SEQUENCE: 28

Met Ala Val Tyr Val His Tyr His Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: N-methyl Norvaline

<400> SEQUENCE: 29

Met Ser Tyr His Tyr Val Val Pro Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-methyl Norvaline

<400> SEQUENCE: 30

Met Leu Ser Tyr Ser His Val Gln Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Norvaline
<220> FEATURE:
<221> NAME/KEY: MOD_RES
<222> LOCATION: (7)..(7)
<223> OTHER INFORMATION: N-methyl Norvaline

<400> SEQUENCE: 31

```
Met Glu Tyr Val Ser Tyr Val Ala Lys
1               5
```

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-methyl Norvaline

<400> SEQUENCE: 32

```
Met Arg His Gln Glu Val Leu Leu Lys
1               5
```

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-methyl Norvaline

<400> SEQUENCE: 33

```
Met Gln Tyr Asp Glu Tyr Val Asp Ser Lys
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-methyl Norvaline

<400> SEQUENCE: 34

```
Met Leu Trp Asp Glu Tyr Val Ala Cys Lys
1               5                   10
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Norvaline

<400> SEQUENCE: 35

```
Met Met Trp Val Glu Phe Tyr Ser Leu Lys
1               5                   10
```

<210> SEQ ID NO 36
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: N-methyl Norvaline

<400> SEQUENCE: 36

Met Val Cys Val Val Leu Tyr Asp Asp Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-methyl Norvaline

<400> SEQUENCE: 37

Met Val Cys Glu Tyr Tyr Val Tyr Ser Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys(FAM)
<220> FEATURE:
<221> NAME/KEY: MOD_RES
<222> LOCATION: (15)..(15)
<223> OTHER INFORMATION: Lys(Biotin)
<220> FEATURE:
<223> OTHER INFORMATION: See specification as filed for detailed
      description of substitutions and preferred embodiments

<400> SEQUENCE: 38

Met Phe Tyr Val Tyr Glu Tyr Val Gln Trp Ser Lys Lys Asp Lys
1               5                   10                  15

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin

<400> SEQUENCE: 39

Asp Lys Leu Tyr Trp Trp Glu Phe Leu
1               5

<210> SEQ ID NO 40
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin
<220> FEATURE:
<221> NAME/KEY: MOD_RES
<222> LOCATION: (1)..(1)
<223> OTHER INFORMATION: Ac(N-Methyl Asp)

<400> SEQUENCE: 40

Asp Lys Leu Tyr Trp Trp Glu Phe Leu
1               5

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin

<400> SEQUENCE: 41

Asn Asn Asn Asn Asn Asp Lys Leu Tyr Trp Trp Glu Phe Leu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin
<220> FEATURE:
<221> NAME/KEY: MOD_RES
<222> LOCATION: (8)..(8)
<223> OTHER INFORMATION: N-Methyl Leu

<400> SEQUENCE: 42

Asn Asn Asn Asn Asn Asp Lys Leu Tyr Trp Trp Glu Phe Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin
<220> FEATURE:
<221> NAME/KEY: MOD_RES
<222> LOCATION: (9)..(9)
<223> OTHER INFORMATION: N-methyl Tyr

<400> SEQUENCE: 43

Asn Asn Asn Asn Asn Asp Lys Leu Tyr Trp Trp Glu Phe Leu
```

```
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin
<220> FEATURE:
<221> NAME/KEY: MOD_RES
<222> LOCATION: (10)..(10)
<223> OTHER INFORMATION: N-methyl Trp

<400> SEQUENCE: 44

```
Asn Asn Asn Asn Asn Asp Lys Leu Tyr Trp Trp Glu Phe Leu
1               5                   10
```

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Amidated peptide
<220> FEATURE:
<221> NAME/KEY: misc_feature
<222> LOCATION: (12)..(12)
<223> OTHER INFORMATION: C-term biotin

<400> SEQUENCE: 45

```
Met Ile Thr Trp Tyr Glu Phe Val Ala Gly Thr Lys
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Amidated peptide; Cyclized peptide
<220> FEATURE:
<221> NAME/KEY: misc_feature
<222> LOCATION: (12)..(12)
<223> OTHER INFORMATION: C-term biotin

<400> SEQUENCE: 46

```
Met Ile Thr Trp Tyr Glu Phe Val Ala Gly Thr Lys
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)

```
<223> OTHER INFORMATION: Amidated peptide
<220> FEATURE:
<221> NAME/KEY: MOD_RES
<222> LOCATION: (1)..(1)
<223> OTHER INFORMATION: N-methyl Norvaline
<220> FEATURE:
<221> NAME/KEY: MOD_RES
<222> LOCATION: (12)..(12)
<223> OTHER INFORMATION: Lys(biotin)

<400> SEQUENCE: 47

Val Ile Thr Trp Tyr Glu Phe Val Ala Gly Thr Lys
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term biotin

<400> SEQUENCE: 48

Met Ser Gln Thr Lys Arg Leu Asp Asp Gln Leu Tyr Trp Trp Glu Tyr
1               5                   10                  15

Leu

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: Amidated peptide
<220> FEATURE:
<221> NAME/KEY: MOD_RES
<222> LOCATION: (20)..(20)
<223> OTHER INFORMATION: Lys(biotin)

<400> SEQUENCE: 49

Met Arg Leu Val Trp Ile Val Arg Ser Arg His Phe Gly Pro Arg Leu
1               5                   10                  15

Arg Met Ala Lys
            20

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Cyclized peptide
<220> FEATURE:
<221> NAME/KEY: MOD_RES
<222> LOCATION: (4)..(4)
<223> OTHER INFORMATION: N-methyl Ala
<220> FEATURE:
<221> NAME/KEY: MOD_RES
<222> LOCATION: (8)..(8)
```

```
<223> OTHER INFORMATION: N-methyl Ala
<220> FEATURE:
<221> NAME/KEY: MOD_RES
<222> LOCATION: (13)..(13)
<223> OTHER INFORMATION: Lys with a modified side chain including either
      biotin or palmitoleic acid

<400> SEQUENCE: 50

Met Phe Tyr Ala Tyr Glu Tyr Ala Gln Trp Ser Lys Lys
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, N-methyl Ala, Met, Asn, Lys, Tyr, Phe or
      Leu
<220> FEATURE:
<221> NAME/KEY: MOD_RES
<222> LOCATION: (3)..(3)
<223> OTHER INFORMATION: Thr, N-methyl Ala, Lys, Asn, Ser or Tyr
<220> FEATURE:
<221> NAME/KEY: MOD_RES
<222> LOCATION: (4)..(4)
<223> OTHER INFORMATION: Trp or N-methyl Ala
<220> FEATURE:
<221> NAME/KEY: MOD_RES
<222> LOCATION: (5)..(5)
<223> OTHER INFORMATION: Tyr or N-methyl Ala
<220> FEATURE:
<221> NAME/KEY: MOD_RES
<222> LOCATION: (6)..(6)
<223> OTHER INFORMATION: Glu, N-methyl Ala or any amino acid
<220> FEATURE:
<221> NAME/KEY: MOD_RES
<222> LOCATION: (7)..(7)
<223> OTHER INFORMATION: Phe, N-methyl Ala, Ser or Tyr
<220> FEATURE:
<221> NAME/KEY: MOD_RES
<222> LOCATION: (8)..(8)
<223> OTHER INFORMATION: Val, N-methyl Ala, Glu or Leu
<220> FEATURE:
<221> NAME/KEY: MOD_RES
<222> LOCATION: (9)..(9)
<223> OTHER INFORMATION: Ala, N-methyl Ala, Ser, Glu or Gln
<220> FEATURE:
<221> NAME/KEY: MOD_RES
<222> LOCATION: (10)..(10)
<223> OTHER INFORMATION: Gly, N-methyl Ala, Glu, Asp, Tyr, Cys or Trp
<220> FEATURE:
<221> NAME/KEY: MOD_RES
<222> LOCATION: (11)..(11)
<223> OTHER INFORMATION: Thr, N-methyl Ala, Lys, Asn or Ser
<220> FEATURE:
<223> OTHER INFORMATION: See specification as filed for detailed
      description of substitutions and preferred embodiments

<400> SEQUENCE: 51

Met Xaa Xaa Xaa Xaa Xaa Xaa Xaa Xaa Xaa Xaa Lys
1               5                   10

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: See specification as filed for detailed
      description of substitutions and preferred embodiments

<400> SEQUENCE: 52
atgwwkwmst rgtakkartw kkwgbmgkrs wmsaaa                              36

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclized peptide
<220> FEATURE:
<221> NAME/KEY: MOD_RES
<222> LOCATION: (4)..(4)
<223> OTHER INFORMATION: N-methyl Ala
<220> FEATURE:
<221> NAME/KEY: MOD_RES
<222> LOCATION: (8)..(8)
<223> OTHER INFORMATION: N-methyl Ala

<400> SEQUENCE: 53

Met Phe Tyr Ala Tyr Glu Tyr Ala Gln Trp Ser Lys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclized peptide
<220> FEATURE:
<221> NAME/KEY: MOD_RES
<222> LOCATION: (4)..(4)
<223> OTHER INFORMATION: N-methyl Ala
<220> FEATURE:
<221> NAME/KEY: MOD_RES
<222> LOCATION: (8)..(8)
<223> OTHER INFORMATION: N-methyl Ala
<220> FEATURE:
<221> NAME/KEY: MOD_RES
<222> LOCATION: (13)..(13)
<223> OTHER INFORMATION: Lys(FAM)

<400> SEQUENCE: 54

Met Phe Tyr Ala Tyr Glu Tyr Ala Gln Trp Ser Lys Lys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Cyclized peptide
<220> FEATURE:
<221> NAME/KEY: MOD_RES
<222> LOCATION: (4)..(4)
<223> OTHER INFORMATION: N-methyl Ala
```

```
<220> FEATURE:
<221> NAME/KEY: MOD_RES
<222> LOCATION: (8)..(8)
<223> OTHER INFORMATION: N-methyl Ala
<220> FEATURE:
<221> NAME/KEY: MOD_RES
<222> LOCATION: (13)..(13)
<223> OTHER INFORMATION: Lys(FAM)
<220> FEATURE:
<221> NAME/KEY: MOD_RES
<222> LOCATION: (14)..(14)
<223> OTHER INFORMATION: Lys(Palmitoleic acid)

<400> SEQUENCE: 55

Met Phe Tyr Ala Tyr Glu Tyr Ala Gln Trp Ser Lys Lys Lys
1               5                   10

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term acetylated
<220> FEATURE:
<221> NAME/KEY: misc_feature
<222> LOCATION: (5)..(5)
<223> OTHER INFORMATION: C-term amidated

<400> SEQUENCE: 56

Pro His Ala His Phe
1               5

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Cys Gly Asp Gly Phe Tyr Ala Cys Tyr Met Asp Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or any amino acid
<220> FEATURE:
<221> NAME/KEY: MOD_RES
<222> LOCATION: (3)..(3)
<223> OTHER INFORMATION: Gly, N-methyl Norvaline, Tyr, Asp, Cys, Glu or
      Trp
<220> FEATURE:
<221> NAME/KEY: MOD_RES
<222> LOCATION: (4)..(4)
<223> OTHER INFORMATION: Asp, N-methyl Norvaline, Tyr or Glu
<220> FEATURE:
<221> NAME/KEY: MOD_RES
<222> LOCATION: (5)..(5)
<223> OTHER INFORMATION: Gly, N-methyl Norvaline, Tyr, Asp, Cys, Glu or
```

```
            Trp
<220> FEATURE:
<221> NAME/KEY: MOD_RES
<222> LOCATION: (6)..(6)
<223> OTHER INFORMATION: Phe, N-methyl Norvaline, Tyr or Leu
<220> FEATURE:
<221> NAME/KEY: MOD_RES
<222> LOCATION: (7)..(7)
<223> OTHER INFORMATION: Tyr or N-methyl Norvaline
<220> FEATURE:
<221> NAME/KEY: MOD_RES
<222> LOCATION: (8)..(8)
<223> OTHER INFORMATION: Ala, N-methyl Norvaline, Glu, Asp, Ala, Ser or
      Tyr
<220> FEATURE:
<221> NAME/KEY: MOD_RES
<222> LOCATION: (9)..(9)
<223> OTHER INFORMATION: Asp or any amino acid
<220> FEATURE:
<223> OTHER INFORMATION: See specification as filed for detailed
      description of substitutions and preferred embodiments

<400> SEQUENCE: 58

Met Xaa Xaa Xaa Xaa Xaa Xaa Xaa Xaa Lys
1               5                   10

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 59
atgnnskrsk akkrktwsta kkmsnnsaaa                                      30

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or any amino acid
<220> FEATURE:
<221> NAME/KEY: MOD_RES
<222> LOCATION: (3)..(3)
<223> OTHER INFORMATION: Pro, N-methyl Norvaline, Tyr, Ser, His or Gln
<220> FEATURE:
<221> NAME/KEY: MOD_RES
<222> LOCATION: (4)..(4)
<223> OTHER INFORMATION: His, N-methyl Norvaline or Tyr
<220> FEATURE:
<221> NAME/KEY: MOD_RES
<222> LOCATION: (5)..(5)
<223> OTHER INFORMATION: Ala, N-methyl Norvaline, Asp, Tyr, Ser or Glu
<220> FEATURE:
<221> NAME/KEY: MOD_RES
<222> LOCATION: (6)..(6)
<223> OTHER INFORMATION: His, N-methyl Norvaline, Tyr or Gln
```

```
<220> FEATURE:
<221> NAME/KEY: MOD_RES
<222> LOCATION: (7)..(7)
<223> OTHER INFORMATION: Phe, N-methyl Norvaline, Leu or Tyr
<220> FEATURE:
<221> NAME/KEY: MOD_RES
<222> LOCATION: (8)..(8)
<223> OTHER INFORMATION: His or any amino acid
<220> FEATURE:
<223> OTHER INFORMATION: See specification as filed for detailed
      description of substitutions and preferred embodiments

<400> SEQUENCE: 60

Met Xaa Xaa Xaa Xaa Xaa Xaa Xaa Lys
1               5

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 61
atgnnsymky akkmkyastw knnsaaa                                      27

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: Cyclized peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 62

Met Xaa Gly Asp Gly Phe Tyr Ala Xaa Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: Cyclized peptide
```

```
<220> FEATURE:
<221> NAME/KEY: MOD_RES
<222> LOCATION: (4)..(5)
<223> OTHER INFORMATION: N-Methyl Norvaline

<400> SEQUENCE: 63

Met Val Cys Val Val Leu Tyr Asp Asp Lys
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclized peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 64

Met Xaa Pro His Ala His Phe Xaa Lys
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: Cyclized peptide
<220> FEATURE:
<221> NAME/KEY: MOD_RES
<222> LOCATION: (3)..(3)
<223> OTHER INFORMATION: N-Methyl Norvaline
<220> FEATURE:
<221> NAME/KEY: MOD_RES
<222> LOCATION: (5)..(5)
<223> OTHER INFORMATION: N-Methyl Norvaline

<400> SEQUENCE: 65

Met Ala Val Tyr Val His Tyr His Lys
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FAM-Asp
<220> FEATURE:
<221> NAME/KEY: misc_feature
<222> LOCATION: (9)..(9)
<223> OTHER INFORMATION: C-term modified
<220> FEATURE:
```

```
<223> OTHER INFORMATION: See specification as filed for detailed
      description of substitutions and preferred embodiments

<400> SEQUENCE: 66

Asp Gln Leu Tyr Trp Trp Glu Tyr Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FAM-Asp
<220> FEATURE:
<221> NAME/KEY: misc_feature
<222> LOCATION: (9)..(9)
<223> OTHER INFORMATION: C-term modified
<220> FEATURE:
<223> OTHER INFORMATION: See specification as filed for detailed
      description of substitutions and preferred embodiments

<400> SEQUENCE: 67

Asp Gln Leu Tyr Trp Trp Glu Tyr Leu
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term modified
<220> FEATURE:
<221> NAME/KEY: MOD_RES
<222> LOCATION: (1)..(1)
<223> OTHER INFORMATION: Lys(FAM)
<220> FEATURE:
<223> OTHER INFORMATION: See specification as filed for detailed
      description of substitutions and preferred embodiments

<400> SEQUENCE: 68

Lys Lys Leu Ser Ser Ile Glu Ser Asp Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: N-term modified
<220> FEATURE:
<221> NAME/KEY: MOD_RES
<222> LOCATION: (1)..(1)
<223> OTHER INFORMATION: Lys(FAM)
<220> FEATURE:
<223> OTHER INFORMATION: See specification as filed for detailed
      description of substitutions and preferred embodiments

<400> SEQUENCE: 69
```

```
Lys Lys Leu Ser Ser Ile Glu Ser Asp Val
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Arg Arg Arg Arg Arg Arg Arg Arg
1               5

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(11)
<223> OTHER INFORMATION: Cyclized peptide
<220> FEATURE:
<223> OTHER INFORMATION: See specification as filed for detailed
      description of substitutions and preferred embodiments

<400> SEQUENCE: 71

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 72

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any N-methyl amino acid

<400> SEQUENCE: 73

Met Phe Phe Xaa Phe Phe
1               5
```

```
<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (21)..(22)
<223> OTHER INFORMATION: tri-(ethylene glycol) phosphate linkage
<220> FEATURE:
<221> NAME/KEY: misc_feature
<222> LOCATION: (24)..(24)
<223> OTHER INFORMATION: 3' puromycin

<400> SEQUENCE: 74
aaaaaaaaaa aaaaaaaaaa aacc                                           24

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline
<220> FEATURE:
<221> NAME/KEY: MOD_RES
<222> LOCATION: (9)..(9)
<223> OTHER INFORMATION: Lys or any Lys derivative

<400> SEQUENCE: 75

Met Ala Val Tyr Val His Tyr His Xaa
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline
<220> FEATURE:
<221> NAME/KEY: MOD_RES
<222> LOCATION: (9)..(9)
<223> OTHER INFORMATION: Lys or any Lys derivative

<400> SEQUENCE: 76

Met Phe Val Gln Val Tyr Tyr His Xaa
1               5

<210> SEQ ID NO 77
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: N-methyl Norvaline
<220> FEATURE:
<221> NAME/KEY: MOD_RES
<222> LOCATION: (7)..(7)
<223> OTHER INFORMATION: N-methyl Norvaline
<220> FEATURE:
<221> NAME/KEY: MOD_RES
<222> LOCATION: (9)..(9)
<223> OTHER INFORMATION: Lys or any Lys derivative

<400> SEQUENCE: 77

Met Leu His Tyr Val Tyr Val Arg Xaa
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline
<220> FEATURE:
<221> NAME/KEY: MOD_RES
<222> LOCATION: (10)..(10)
<223> OTHER INFORMATION: Lys or any Lys derivative

<400> SEQUENCE: 78

Met Val Cys Val Val Leu Tyr Asp Asp Xaa
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl Norvaline
<220> FEATURE:
<221> NAME/KEY: MOD_RES
<222> LOCATION: (7)..(7)
<223> OTHER INFORMATION: N-methyl Norvaline
<220> FEATURE:
<221> NAME/KEY: MOD_RES
<222> LOCATION: (10)..(10)
<223> OTHER INFORMATION: Lys or any Lys derivative

<400> SEQUENCE: 79

Met Glu Val Tyr Glu Tyr Val Ser Leu Xaa
1               5                   10

<210> SEQ ID NO 80
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: N-methyl Norvaline
<220> FEATURE:
<221> NAME/KEY: MOD_RES
<222> LOCATION: (8)..(8)
<223> OTHER INFORMATION: N-methyl Norvaline
<220> FEATURE:
<221> NAME/KEY: MOD_RES
<222> LOCATION: (10)..(10)
<223> OTHER INFORMATION: Lys or any Lys derivative

<400> SEQUENCE: 80

Met Asn Glu Tyr Val Leu Tyr Val Leu Xaa
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline

<400> SEQUENCE: 81

Met Ala Xaa Tyr Xaa His Tyr His Lys
1               5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: N-methyl Norvaline
<220> FEATURE:
<221> NAME/KEY: MOD_RES
<222> LOCATION: (5)..(5)
<223> OTHER INFORMATION: N-methyl Norvaline

<400> SEQUENCE: 82

Met Val Cys Xaa Xaa Leu Tyr Asp Asp Lys
1               5                   10
```